(12) United States Patent
Scheib et al.

(10) Patent No.: US 12,740,809 B2
(45) Date of Patent: Sep. 22, 2026

(54) ROBOTICALLY CONTROLLED UTERINE MANIPULATOR

(71) Applicant: Cilag GmbH International, Zug (CH)

(72) Inventors: Charles J. Scheib, Loveland, OH (US); Matthew Vargas, San Francisco, CA (US); Clinton Denlinger, Cincinnati, OH (US)

(73) Assignee: CILAG GMBH INTERNATIONAL, Zug (CH)

( * ) Notice: Subject to any disclaimer, the term of this patent is extended or adjusted under 35 U.S.C. 154(b) by 547 days.

(21) Appl. No.: 17/468,754

(22) Filed: Sep. 8, 2021

(65) Prior Publication Data

US 2023/0077141 A1 Mar. 9, 2023

(51) Int. Cl.

| | |
|---|---|
| ***A61B 34/30*** | (2016.01) |
| ***A61B 17/42*** | (2006.01) |
| ***A61B 34/00*** | (2016.01) |
| ***A61B 34/35*** | (2016.01) |
| ***A61G 13/10*** | (2006.01) |
| *A61B 17/00* | (2006.01) |

(52) U.S. Cl.

CPC .......... *A61B 17/4241* (2013.01); *A61B 34/35* (2016.02); *A61B 34/76* (2016.02); *A61G 13/101* (2013.01); *A61B 2017/00199* (2013.01); *A61B 2017/4216* (2013.01); *A61B 2034/301* (2016.02); *A61B 2034/302* (2016.02)

(58) Field of Classification Search

CPC ...... A61B 17/4241; A61B 2017/00199; A61B 2017/4216; A61B 34/35; A61B 2034/301; A61B 2034/302; A61B 2018/00559

See application file for complete search history.

(56) References Cited

U.S. PATENT DOCUMENTS 4,728,020 A * 3/1988 Green .................. A61B 17/072 227/19
9,743,955 B2 8/2017 Hill et al.
9,763,741 B2 9/2017 Alvarez et al.
9,788,859 B2 10/2017 Parys (Continued)

FOREIGN PATENT DOCUMENTS

EP 3981347 A2 4/2022
WO WO-2020206297 A1 * 10/2020 ......... A61B 17/4241

OTHER PUBLICATIONS

International Search Report and Written Opinion, received for PCT Application No. PCT/IB2022/058317, mailed on Feb. 8, 2023, 25 pages.

(Continued)

*Primary Examiner* — Katherine H Schwiker
*Assistant Examiner* — Zehra Jaffri
(74) *Attorney, Agent, or Firm* — Joshua D. Young

(57) ABSTRACT

A system includes a robotic platform and a uterine manipulator. The robotic platform includes a base, a plurality of robotic arms, and a grounding structure configured to couple one or more of the robotic arms to the base. The uterine manipulator includes an interface configured to couple with a first robotic arm of the robotic platform. The uterine manipulator further includes a shaft assembly extending from the interface and a colpotomy cup slidably attached along a length of the shaft assembly. The first robotic arm is configured to move the uterine manipulator relative to a patient.

18 Claims, 43 Drawing Sheets

(56) References Cited

U.S. PATENT DOCUMENTS

| | | | |
|---|---|---|---|
| 10,464,209 B2 | 11/2019 | Ho et al. | |
| 10,639,072 B2 | 5/2020 | Ahluwalia | |
| 10,667,875 B2 | 6/2020 | DeFonzo et al. | |
| 10,765,303 B2 | 9/2020 | Graetzel et al. | |
| 10,827,913 B2 | 11/2020 | Ummalaneni et al. | |
| 10,881,280 B2 | 1/2021 | Baez, Jr. | |
| 10,898,277 B2 | 1/2021 | Srinivasan et al. | |
| 10,905,505 B1 | 2/2021 | Barakat et al. | |
| 11,058,493 B2 | 7/2021 | Rafii-tari et al. | |
| 2008/0058836 A1* | 3/2008 | Moll | A61B 17/12172 606/130 |
| 2010/0106163 A1* | 4/2010 | Blair | A61B 17/4241 606/119 |
| 2013/0206147 A1 | 8/2013 | Skalyni | |
| 2013/0345521 A1 | 12/2013 | Williams et al. | |
| 2014/0330133 A1 | 11/2014 | Stern | |
| 2015/0148812 A1 | 5/2015 | Ahluwalia | |
| 2018/0078439 A1* | 3/2018 | Cagle | A61B 34/30 |
| 2018/0325552 A1 | 11/2018 | Weihe et al. | |
| 2019/0076100 A1 | 3/2019 | Narkiss et al. | |
| 2019/0150983 A1 | 5/2019 | Prior et al. | |
| 2019/0216555 A1 | 7/2019 | Dimaio et al. | |
| 2019/0321079 A1* | 10/2019 | DaSilva | A61B 17/12136 |
| 2020/0078109 A1* | 3/2020 | Steger | A61B 34/37 |
| 2020/0188044 A1 | 6/2020 | Penny et al. | |
| 2020/0253676 A1* | 8/2020 | Traina | A61B 34/30 |
| 2020/0337729 A1 | 10/2020 | Begg et al. | |
| 2021/0100584 A1 | 4/2021 | Einarsson | |
| 2021/0161606 A1* | 6/2021 | Hares | A61B 17/0469 |
| 2021/0229279 A1 | 7/2021 | Colbrunn et al. | |
| 2021/0267830 A1 | 9/2021 | Ruiz | |
| 2021/0275257 A1 | 9/2021 | Prior et al. | |
| 2021/0307850 A1 | 10/2021 | Barakat et al. | |
| 2021/0330405 A1 | 10/2021 | Gonenc et al. | |
| 2021/0338474 A1 | 11/2021 | Mamo et al. | |
| 2021/0353331 A1 | 11/2021 | Prior et al. | |
| 2022/0110701 A1 | 4/2022 | Crawford et al. | |
| 2022/0160448 A1 | 5/2022 | Gomez et al. | |

OTHER PUBLICATIONS

Invitation to Pay Additional Fees, received for PCT Application No. PCT/IB2022/058317, mailed on Dec. 21, 2022, 13 pages.

* cited by examiner

ROBOTICALLY CONTROLLED UTERINE MANIPULATOR

BACKGROUND

A variety of medical instruments may be used in procedures conducted by a medical professional operator, as well as applications in robotically assisted surgeries. In the case of robotically assisted surgery, the clinician may operate a master controller to remotely control the motion of such medical instruments at a surgical site. The controller may be separated from the patient by a significant distance (e.g., across the operating room, in a different room, or in a completely different building than the patient). Alternatively, a controller may be positioned quite near the patient in the operating room. Regardless, the controller may include one or more hand input devices (such as joysticks, exoskeletol gloves, master manipulators, or the like), which are coupled by a servo mechanism to the medical instrument. In some scenarios, a servo motor moves a manipulator supporting the medical instrument based on the clinician's manipulation of the hand input devices. During the medical procedure, the clinician may employ, via a robotic system, a variety of medical instruments including an ultrasonic blade, a surgical stapler, a tissue grasper, a needle driver, an electrosurgical cautery probes, etc. Each of these structures performs functions for the clinician, for example, cutting tissue, coagulating tissue, holding or driving a needle, grasping a blood vessel, dissecting tissue, or cauterizing tissue.

Examples of robotic systems are described in U.S. Pat. No. 9,763,741, entitled "System for Robotic-Assisted Endolumenal Surgery and Related Methods," issued Sep. 19, 2017, the disclosure of which is incorporated by reference herein, in its entirety; U.S. Pat. No. 10,464,209, entitled "Robotic System with Indication of Boundary for Robotic Arm," issued Nov. 5, 2019, the disclosure of which is incorporated by reference herein, in its entirety; U.S. Pat. No. 10,667,875, entitled "Systems and Techniques for Providing Multiple Perspectives During Medical Procedures," issued Jun. 2, 2020, the disclosure of which is incorporated by reference herein, in its entirety; U.S. Pat. No. 10,765,303, entitled "System and Method for Driving Medical Instrument," issued Sep. 8, 2020, the disclosure of which is incorporated by reference herein, in its entirety; U.S. Pat. No. 10,827,913, entitled "Systems and Methods for Displaying Estimated Location of Instrument," issued Nov. 10, 2020, the disclosure of which is incorporated by reference herein, in its entirety; U.S. Pat. No. 10,881,280, entitled "Manually and Robotically Controllable Medical Instruments," issued Jan. 5, 2021, the disclosure of which is incorporated by reference herein, in its entirety; U.S. Pat. No. 10,898,277, entitled "Systems and Methods for Registration of Location Sensors," issued Jan. 26, 2012, the disclosure of which is incorporated by reference herein, in its entirety; and U.S. Pat. No. 11,058,493, entitled "Robotic System Configured for Navigation Path Tracing," issued Jul. 13, 2021, the disclosure of which is incorporated by reference herein, in its entirety.

During a hysterectomy procedure, a colpotomy may be performed at the cervicovaginal junction. Such procedures may include the use of a uterine manipulator that includes a colpotomy cup or similar structure. Examples of instruments that may be used during a hysterectomy procedure are described in U.S. Pat. No. 9,743,955, entitled "Intracorporeal Transilluminator of Tissue Using LED Array," issued Aug. 29, 2017; U.S. Pat. No. 9,788,859, entitled "Uterine Manipulators and Related Components and Methods," issued Oct. 17, 2017; U.S. Pat. No. 10,639,072, entitled "Uterine Manipulator," issued May 5, 2020; U.S. Pub. No. 2021/0100584, entitled "Uterine Manipulator," published Apr. 8, 2021; U.S. Pub. No. 2018/0325552, entitled "Colpotomy Systems, Devices, and Methods with Rotational Cutting," published Nov. 15, 2018.

While several medical instruments, systems, and methods have been made and used, it is believed that no one prior to the inventors has made or used the invention described in the appended claims.

BRIEF DESCRIPTION OF THE DRAWINGS

The disclosed aspects will hereinafter be described in conjunction with the appended drawings, provided to illustrate and not to limit the disclosed aspects, wherein like designations denote like elements.

DETAILED DESCRIPTION

I. Overview of Example of Robotic System

Aspects of the present disclosure may be integrated into a robotically-enabled medical system capable of performing a variety of medical procedures, including both minimally invasive, such as laparoscopy, and non-invasive, such as endoscopy, procedures. Among endoscopy procedures, the system may be capable of performing bronchoscopy, ureteroscopy, gastroscopy, etc.

In addition to performing the breadth of procedures, the system may provide additional benefits, such as enhanced imaging and guidance to assist the physician. Additionally, the system may provide the physician with the ability to perform the procedure from an ergonomic position without the need for awkward arm motions and positions. Still further, the system may provide the physician with the ability to perform the procedure with improved ease of use such that one or more of the instruments of the system can be controlled by a single user.

Various embodiments will be described below in conjunction with the drawings for purposes of illustration. It should be appreciated that many other implementations of the disclosed concepts are possible, and various advantages can be achieved with the disclosed implementations. Headings are included herein for reference and to aid in locating various sections. These headings are not intended to limit the scope of the concepts described with respect thereto. Such concepts may have applicability throughout the entire specification.

A. Example of Robotic System Cart

Figure 1:
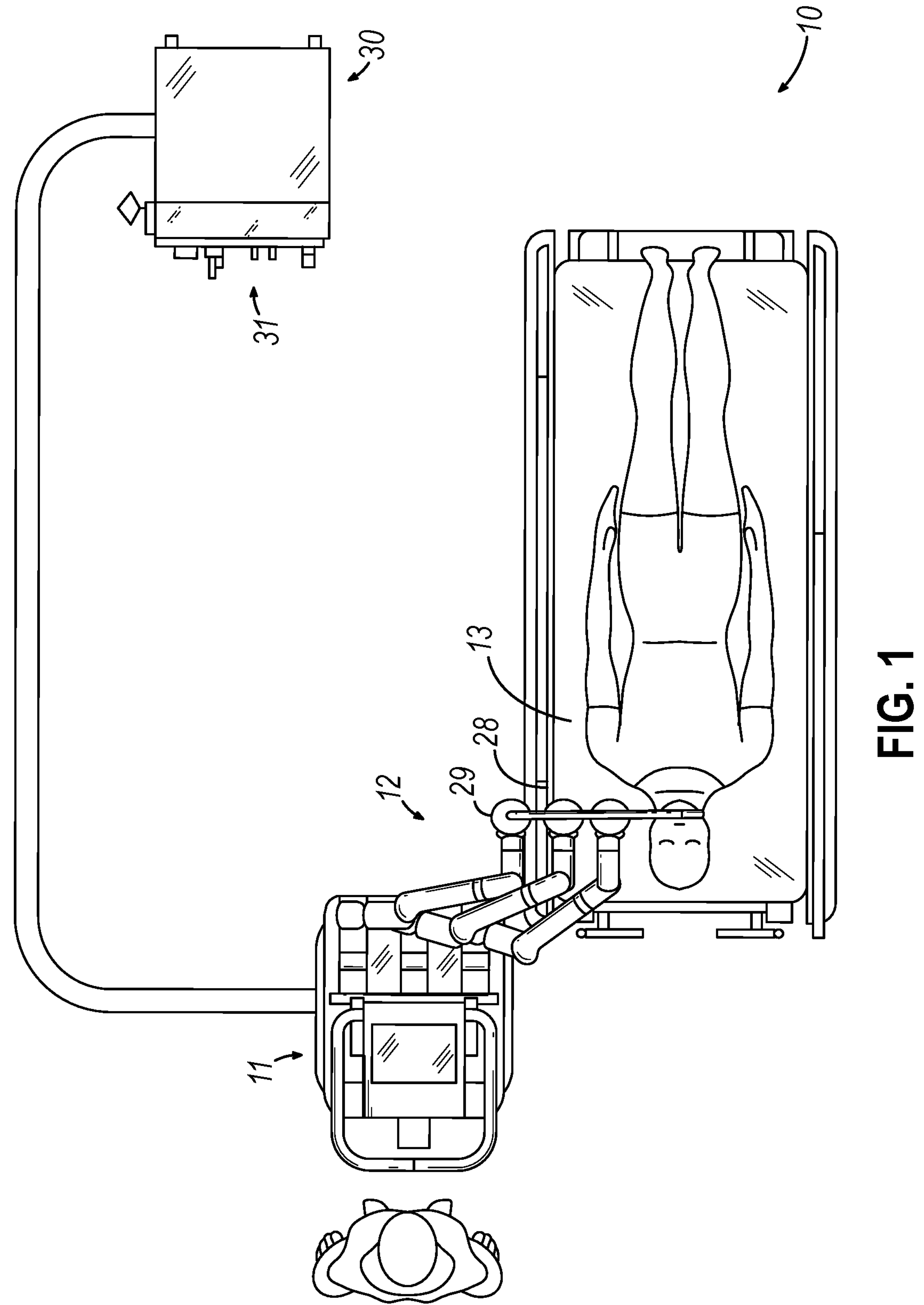
FIG. 1 depicts an embodiment of a cart-based robotic system arranged for diagnostic and/or therapeutic bronchoscopy procedure(s).
Figure 2:
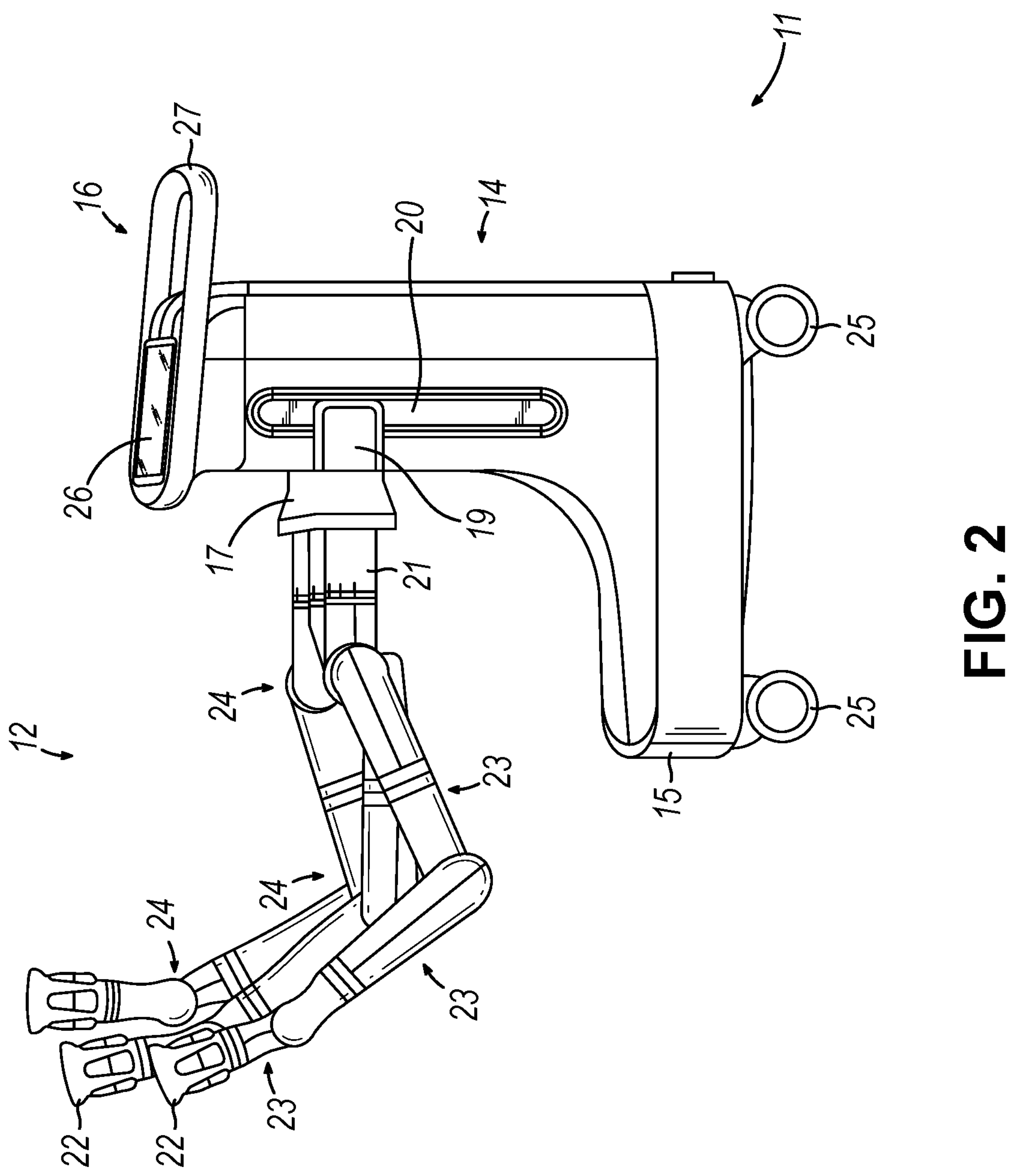
FIG. 2 depicts further aspects of the robotic system of FIG. 1.

The robotically-enabled medical system may be configured in a variety of ways depending on the particular procedure. FIG. 1 illustrates an embodiment of a cart-based robotically-enabled system (10) arranged for a diagnostic and/or therapeutic bronchoscopy procedure. During a bronchoscopy, the system (10) may comprise a cart (11) having one or more robotic arms (12) to deliver a medical instrument, such as a steerable endoscope (13), which may be a procedure-specific bronchoscope for bronchoscopy, to a natural orifice access point (i.e., the mouth of the patient positioned on a table in the present example) to deliver diagnostic and/or therapeutic tools. As shown, the cart (11) may be positioned proximate to the patient's upper torso in order to provide access to the access point. Similarly, the robotic arms (12) may be actuated to position the bronchoscope relative to the access point. The arrangement in FIG. 1 may also be utilized when performing a gastro-intestinal (GI) procedure with a gastroscope, a specialized endoscope for GI procedures. FIG. 2 depicts an example embodiment of the cart in greater detail.

With continued reference to FIG. 1, once the cart (11) is properly positioned, the robotic arms (12) may insert the steerable endoscope (13) into the patient robotically, manually, or a combination thereof. As shown, the steerable endoscope (13) may comprise at least two telescoping parts, such as an inner leader portion and an outer sheath portion, each portion coupled to a separate instrument driver from the set of instrument drivers (28), each instrument driver coupled to the distal end of an individual robotic arm. This linear arrangement of the instrument drivers (28), which facilitates coaxially aligning the leader portion with the sheath portion, creates a "virtual rail" (29) that may be repositioned in space by manipulating the one or more robotic arms (12) into different angles and/or positions. The virtual rails described herein are depicted in the Figures using dashed lines, and accordingly the dashed lines do not depict any physical structure of the system. Translation of the instrument drivers (28) along the virtual rail (29) telescopes the inner leader portion relative to the outer sheath portion or advances or retracts the endoscope (13) from the patient. The angle of the virtual rail (29) may be adjusted, translated, and pivoted based on clinical application or physician preference. For example, in bronchoscopy, the angle and position of the virtual rail (29) as shown represents a compromise between providing physician access to the endoscope (13) while minimizing friction that results from bending the endoscope (13) into the patient's mouth.

The endoscope (13) may be directed down the patient's trachea and lungs after insertion using precise commands from the robotic system until reaching the target destination or operative site. In order to enhance navigation through the patient's lung network and/or reach the desired target, the endoscope (13) may be manipulated to telescopically extend the inner leader portion from the outer sheath portion to obtain enhanced articulation and greater bend radius. The use of separate instrument drivers (28) also allows the leader portion and sheath portion to be driven independent of each other.

For example, the endoscope (13) may be directed to deliver a biopsy needle to a target, such as, for example, a lesion or nodule within the lungs of a patient. The needle may be deployed down a working channel that runs the length of the endoscope to obtain a tissue sample to be analyzed by a pathologist. Depending on the pathology results, additional tools may be deployed down the working channel of the endoscope for additional biopsies. After identifying a nodule to be malignant, the endoscope (13) may endoscopically deliver tools to resect the potentially cancerous tissue. In some instances, diagnostic and therapeutic treatments can be delivered in separate procedures. In those circumstances, the endoscope (13) may also be used to deliver a fiducial to "mark" the location of the target nodule as well. In other instances, diagnostic and therapeutic treatments may be delivered during the same procedure.

The system (10) may also include a movable tower (30), which may be connected via support cables to the cart (11) to provide support for controls, electronics, fluidics, optics, sensors, and/or power to the cart (11). Placing such functionality in the tower (30) allows for a smaller form factor cart (11) that may be more easily adjusted and/or repositioned by an operating physician and his/her staff. Additionally, the division of functionality between the cart/table and the support tower (30) reduces operating room clutter and facilitates improving clinical workflow. While the cart (11) may be positioned close to the patient, the tower (30) may be stowed in a remote location to stay out of the way during a procedure.

In support of the robotic systems described above, the tower (30) may include component(s) of a computer-based control system that stores computer program instructions, for example, within a non-transitory computer-readable storage medium such as a persistent magnetic storage drive, solid state drive, etc. The execution of those instructions, whether the execution occurs in the tower (30) or the cart (11), may control the entire system or sub-system(s) thereof. For example, when executed by a processor of the computer system, the instructions may cause the components of the robotics system to actuate the relevant carriages and arm mounts, actuate the robotics arms, and control the medical instruments. For example, in response to receiving the control signal, the motors in the joints of the robotics arms may position the arms into a certain posture.

The tower (30) may also include a pump, flow meter, valve control, and/or fluid access in order to provide controlled irrigation and aspiration capabilities to the system that may be deployed through the endoscope (13). These components may also be controlled using the computer system of tower (30). In some embodiments, irrigation and aspiration capabilities may be delivered directly to the endoscope (13) through separate cable(s).

The tower (30) may include a voltage and surge protector designed to provide filtered and protected electrical power to the cart (11), thereby avoiding placement of a power transformer and other auxiliary power components in the cart (11), resulting in a smaller, more moveable cart (11).

The tower (30) may also include support equipment for the sensors deployed throughout the robotic system (10). For example, the tower (30) may include opto-electronics equipment for detecting, receiving, and processing data received from the optical sensors or cameras throughout the robotic system (10). In combination with the control system, such opto-electronics equipment may be used to generate real-time images for display in any number of consoles deployed throughout the system, including in the tower (30). Similarly, the tower (30) may also include an electronic subsystem for receiving and processing signals received from deployed electromagnetic (EM) sensors. The tower (30) may also be used to house and position an EM field generator for detection by EM sensors in or on the medical instrument.

The tower (30) may also include a console (31) in addition to other consoles available in the rest of the system, e.g., console mounted on top of the cart. The console (31) may include a user interface and a display screen, such as a touchscreen, for the physician operator. Consoles in system (10) are generally designed to provide both robotic controls as well as pre-operative and real-time information of the procedure, such as navigational and localization information of the endoscope (13). When the console (31) is not the only console available to the physician, it may be used by a second operator, such as a nurse, to monitor the health or vitals of the patient and the operation of system, as well as provide procedure-specific data, such as navigational and localization information. In other embodiments, the console (31) is housed in a body that is separate from the tower (30).

The tower (30) may be coupled to the cart (11) and endoscope (13) through one or more cables or connections (not shown). In some embodiments, the support functionality from the tower (30) may be provided through a single cable to the cart (11), simplifying and de-cluttering the operating room. In other embodiments, specific functionality may be coupled in separate cabling and connections. For example, while power may be provided through a single power cable to the cart, the support for controls, optics, fluidics, and/or navigation may be provided through a separate cable.

FIG. 2 provides a detailed illustration of an embodiment of the cart from the cart-based robotically-enabled system shown in FIG. 1. The cart (11) generally includes an elongated support structure (14) (often referred to as a "column"), a cart base (15), and a console (16) at the top of the column (14). The column (14) may include one or more carriages, such as a carriage (17) (alternatively "arm support") for supporting the deployment of one or more robotic arms (12) (three shown in FIG. 2). The carriage (17) may include individually configurable arm mounts that rotate along a perpendicular axis to adjust the base of the robotic arms (12) for better positioning relative to the patient. The carriage (17) also includes a carriage interface (19) that allows the carriage (17) to vertically translate along the column (14).

The carriage interface (19) is connected to the column (14) through slots, such as slot (20), that are positioned on opposite sides of the column (14) to guide the vertical translation of the carriage (17). The slot (20) contains a vertical translation interface to position and hold the carriage at various vertical heights relative to the cart base (15). Vertical translation of the carriage (17) allows the cart (11) to adjust the reach of the robotic arms (12) to meet a variety of table heights, patient sizes, and physician preferences. Similarly, the individually configurable arm mounts on the carriage (17) allow the robotic arm base (21) of robotic arms (12) to be angled in a variety of configurations.

In some embodiments, the slot (20) may be supplemented with slot covers that are flush and parallel to the slot surface to prevent dirt and fluid ingress into the internal chambers of the column (14) and the vertical translation interface as the carriage (17) vertically translates. The slot covers may be deployed through pairs of spring spools positioned near the vertical top and bottom of the slot (20). The covers are coiled within the spools until deployed to extend and retract from their coiled state as the carriage (17) vertically translates up and down. The spring-loading of the spools provides force to retract the cover into a spool when carriage (17) translates towards the spool, while also maintaining a tight seal when the carriage (17) translates away from the spool. The covers may be connected to the carriage (17) using, for example, brackets in the carriage interface (19) to ensure proper extension and retraction of the cover as the carriage (17) translates.

The column (14) may internally comprise mechanisms, such as gears and motors, that are designed to use a vertically aligned lead screw to translate the carriage (17) in a mechanized fashion in response to control signals generated in response to user inputs, e.g., inputs from the console (16).

The robotic arms (12) may generally comprise robotic arm bases (21) and end effectors (22), separated by a series of linkages (23) that are connected by a series of joints (24), each joint comprising an independent actuator, each actuator comprising an independently controllable motor. Each independently controllable joint represents an independent degree of freedom available to the robotic arm. Each of the arms (12) have seven joints, and thus provide seven degrees of freedom. A multitude of joints result in a multitude of degrees of freedom, allowing for "redundant" degrees of freedom. Redundant degrees of freedom allow the robotic arms (12) to position their respective end effectors (22) at a specific position, orientation, and trajectory in space using different linkage positions and joint angles. This allows for the system to position and direct a medical instrument from a desired point in space while allowing the physician to move the arm joints into a clinically advantageous position away from the patient to create greater access, while avoiding arm collisions.

The cart base (15) balances the weight of the column (14), carriage (17), and arms (12) over the floor. Accordingly, the cart base (15) houses heavier components, such as electronics, motors, power supply, as well as components that either enable movement and/or immobilize the cart. For example, the cart base (15) includes rollable wheel-shaped casters (25) that allow for the cart to easily move around the room prior to a procedure. After reaching the appropriate position, the casters (25) may be immobilized using wheel locks to hold the cart (11) in place during the procedure.

Positioned at the vertical end of column (14), the console (16) allows for both a user interface for receiving user input and a display screen (or a dual-purpose device such as, for example, a touchscreen (26)) to provide the physician user with both pre-operative and intra-operative data. Potential pre-operative data on the touchscreen (26) may include pre-operative plans, navigation and mapping data derived from pre-operative computerized tomography (CT) scans, and/or notes from pre-operative patient interviews. Intra-operative data on display may include optical information provided from the tool, sensor and coordinate information from sensors, as well as vital patient statistics, such as respiration, heart rate, and/or pulse. The console (16) may be positioned and tilted to allow a physician to access the console from the side of the column (14) opposite carriage (17). From this position, the physician may view the console (16), robotic arms (12), and patient while operating the console (16) from behind the cart (11). As shown, the console (16) also includes a handle (27) to assist with maneuvering and stabilizing cart (11).

Figure 3:
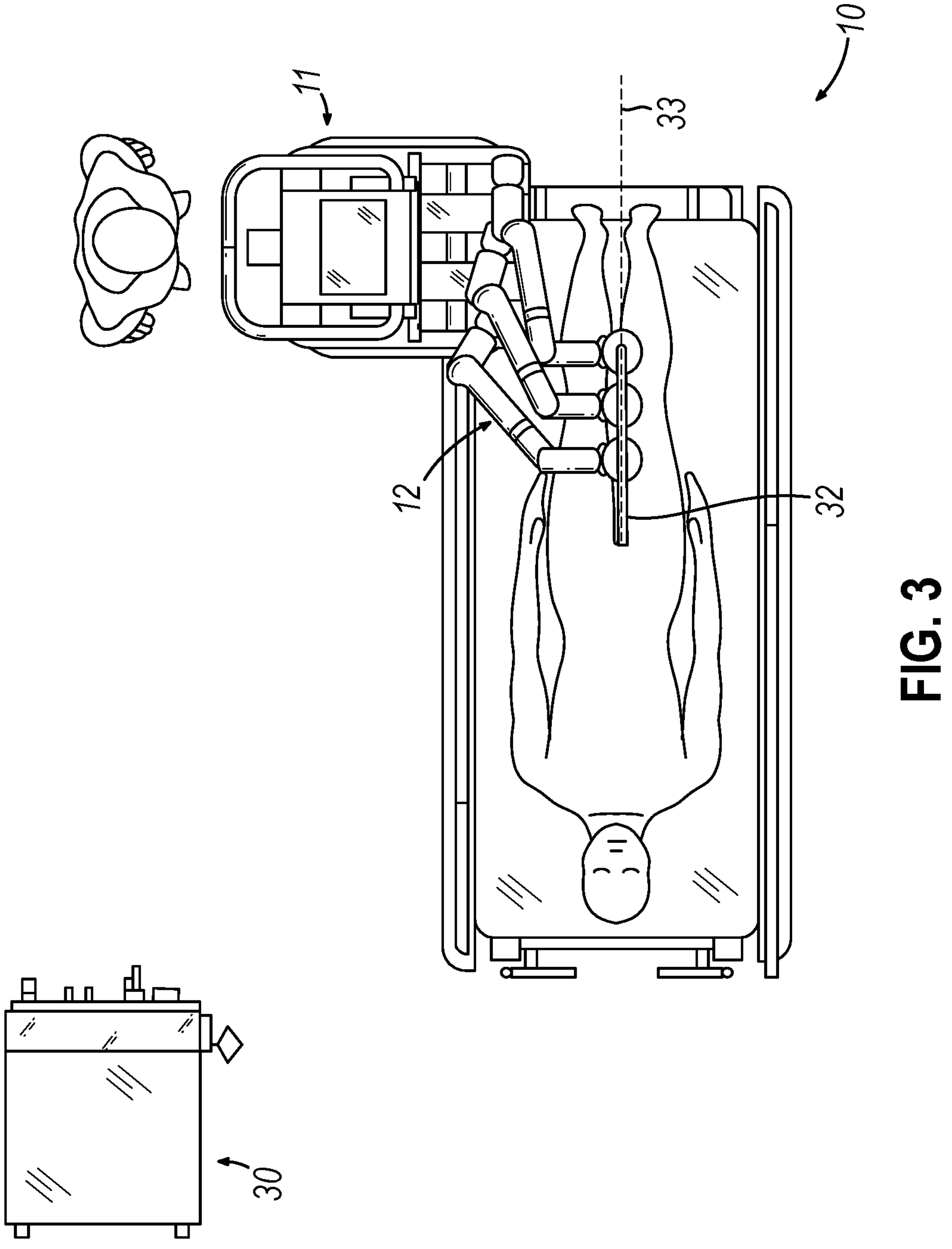
FIG. 3 depicts an embodiment of the robotic system of FIG. 1 arranged for ureteroscopy.

FIG. 3 illustrates an embodiment of a robotically-enabled system (10) arranged for ureteroscopy. In a ureteroscopic procedure, the cart (11) may be positioned to deliver a ureteroscope (32), a procedure-specific endoscope designed to traverse a patient's urethra and ureter, to the lower abdominal area of the patient. In a ureteroscopy, it may be desirable for the ureteroscope (32) to be directly aligned with the patient's urethra to reduce friction and forces on the sensitive anatomy in the area. As shown, the cart (11) may be aligned at the foot of the table to allow the robotic arms (12) to position the ureteroscope (32) for direct linear access to the patient's urethra. From the foot of the table, the robotic arms (12) may insert the ureteroscope (32) along the virtual rail (33) directly into the patient's lower abdomen through the urethra.

After insertion into the urethra, using similar control techniques as in bronchoscopy, the ureteroscope (32) may be navigated into the bladder, ureters, and/or kidneys for diagnostic and/or therapeutic applications. For example, the ureteroscope (32) may be directed into the ureter and kidneys to break up kidney stone build up using a laser or ultrasonic lithotripsy device deployed down the working channel of the ureteroscope (32). After lithotripsy is complete, the resulting stone fragments may be removed using baskets deployed down the ureteroscope (32).

Figure 4:
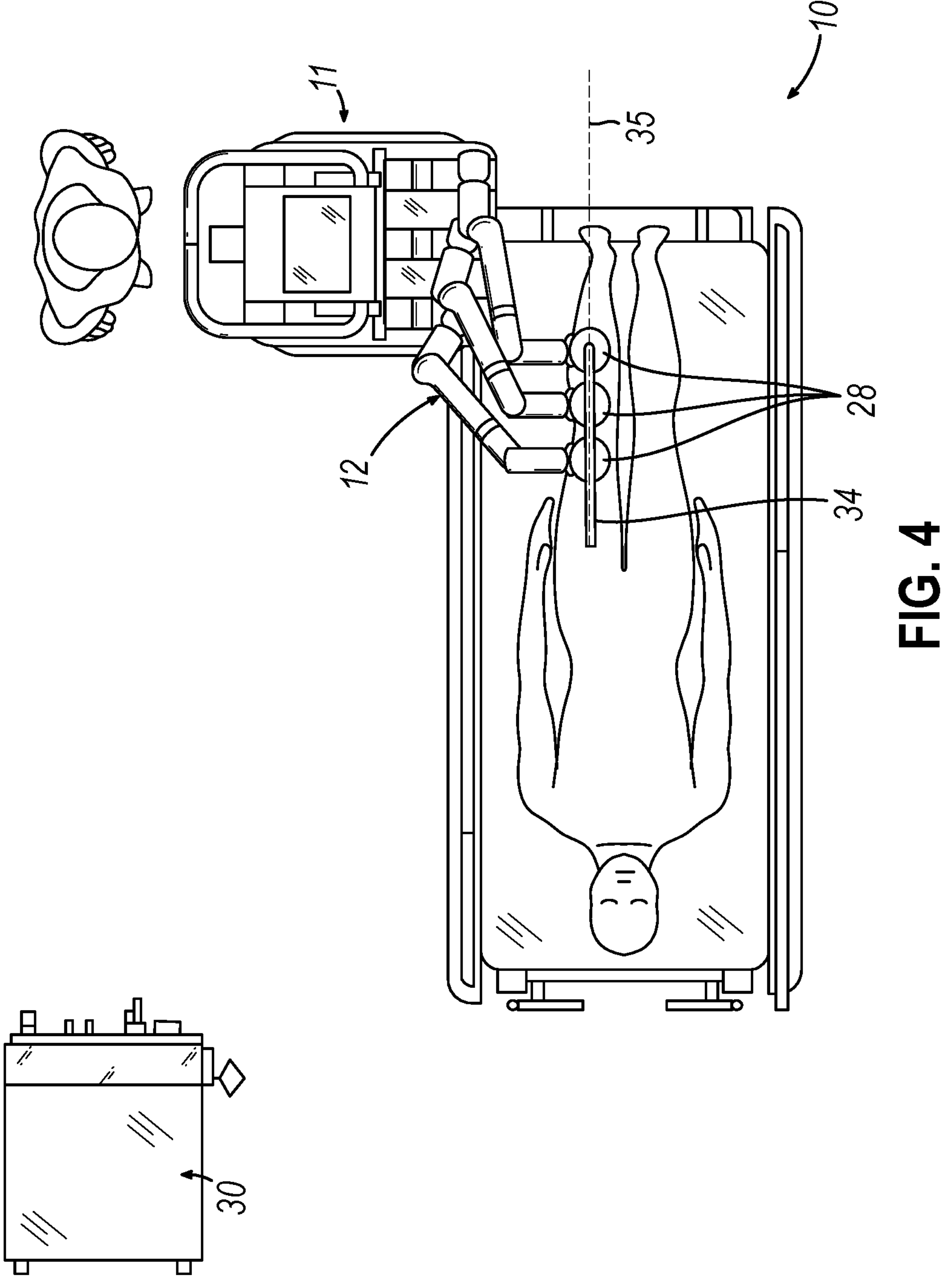
FIG. 4 depicts an embodiment of the robotic system of FIG. 1 arranged for a vascular procedure.

FIG. 4 illustrates an embodiment of a robotically-enabled system similarly arranged for a vascular procedure. In a vascular procedure, the system (10) may be configured such that the cart (11) may deliver a medical instrument (34), such as a steerable catheter, to an access point in the femoral artery in the patient's leg. The femoral artery presents both a larger diameter for navigation as well as a relatively less circuitous and tortuous path to the patient's heart, which simplifies navigation. As in a ureteroscopic procedure, the cart (11) may be positioned towards the patient's legs and lower abdomen to allow the robotic arms (12) to provide a virtual rail (35) with direct linear access to the femoral artery access point in the patient's thigh/hip region. After insertion into the artery, the medical instrument (34) may be directed and inserted by translating the instrument drivers (28). Alternatively, the cart may be positioned around the patient's upper abdomen in order to reach alternative vascular access points, such as, for example, the carotid and brachial arteries near the shoulder and wrist.

B. Example of Robotic System Table

Figure 5:
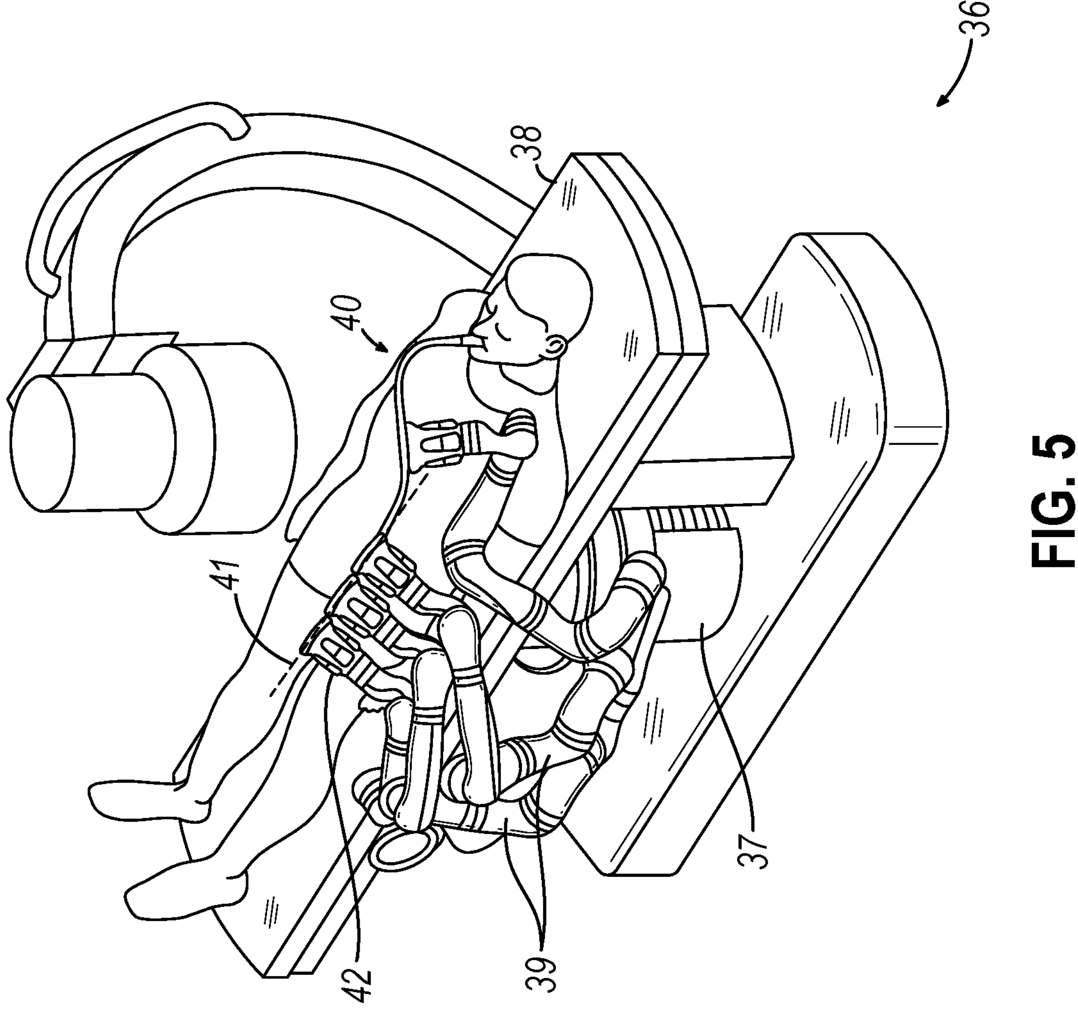
FIG. 5 depicts an embodiment of a table-based robotic system arranged for a bronchoscopy procedure.

Embodiments of the robotically-enabled medical system may also incorporate the patient's table. Incorporation of the table reduces the amount of capital equipment within the operating room by removing the cart, which allows greater access to the patient. FIG. 5 illustrates an embodiment of such a robotically-enabled system arranged for a bronchoscopy procedure. System (36) includes a support structure or column (37) for supporting platform (38) (shown as a "table" or "bed") over the floor. Much like in the cart-based systems, the end effectors of the robotic arms (39) of the system (36) comprise instrument drivers (42) that are designed to manipulate an elongated medical instrument, such as a bronchoscope (40) in FIG. 5, through or along a virtual rail (41) formed from the linear alignment of the instrument drivers (42). In practice, a C-arm for providing fluoroscopic imaging may be positioned over the patient's upper abdominal area by placing the emitter and detector around table (38).

Figure 6:
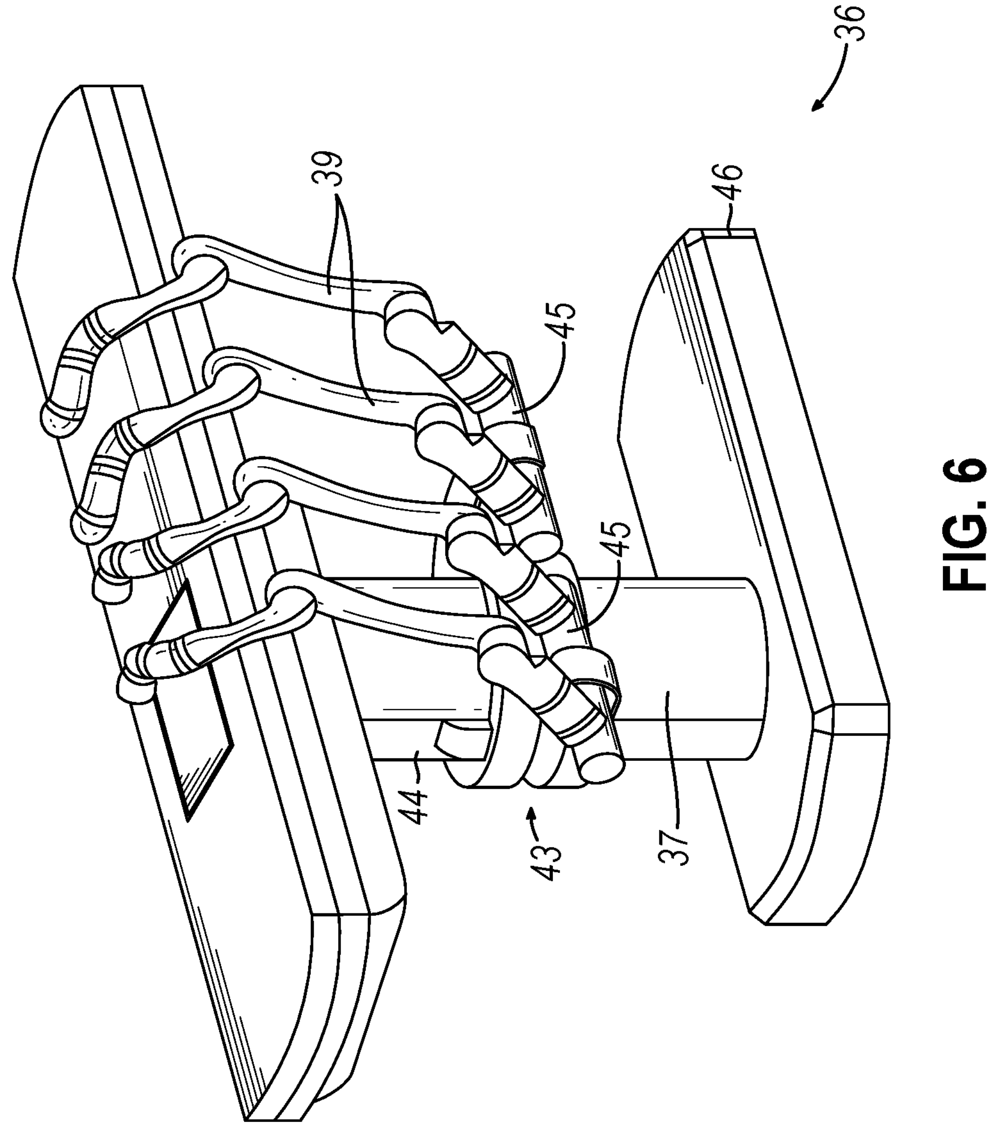
FIG. 6 provides an alternative view of the robotic system of FIG. 5.

FIG. 6 provides an alternative view of the system (36) without the patient and medical instrument for discussion purposes. As shown, the column (37) may include one or more carriages (43) shown as ring-shaped in the system (36), from which the one or more robotic arms (39) may be based. The carriages (43) may translate along a vertical column interface 44 that runs the length of the column (37) to provide different vantage points from which the robotic arms (39) may be positioned to reach the patient. The carriage(s) (43) may rotate around the column (37) using a mechanical motor positioned within the column (37) to allow the robotic arms (39) to have access to multiples sides of the table (38), such as, for example, both sides of the patient. In embodiments with multiple carriages, the carriages may be individually positioned on the column and may translate and/or rotate independent of the other carriages. While carriages (43) need not surround the column (37) or even be circular, the ring-shape as shown facilitates rotation of the carriages (43) around the column (37) while maintaining structural balance. Rotation and translation of the carriages (43) allows the system to align the medical instruments, such as endoscopes and laparoscopes, into different access points on the patient. In other embodiments (not shown), the system (36) can include a patient table or bed with adjustable arm supports in the form of bars or rails extending alongside it. One or more robotic arms (39) (e.g., via a shoulder with an elbow joint) can be attached to the adjustable arm supports, which can be vertically adjusted. By providing vertical adjustment, the robotic arms (39) are advantageously capable of being stowed compactly beneath the patient table or bed, and subsequently raised during a procedure.

Figure 9:
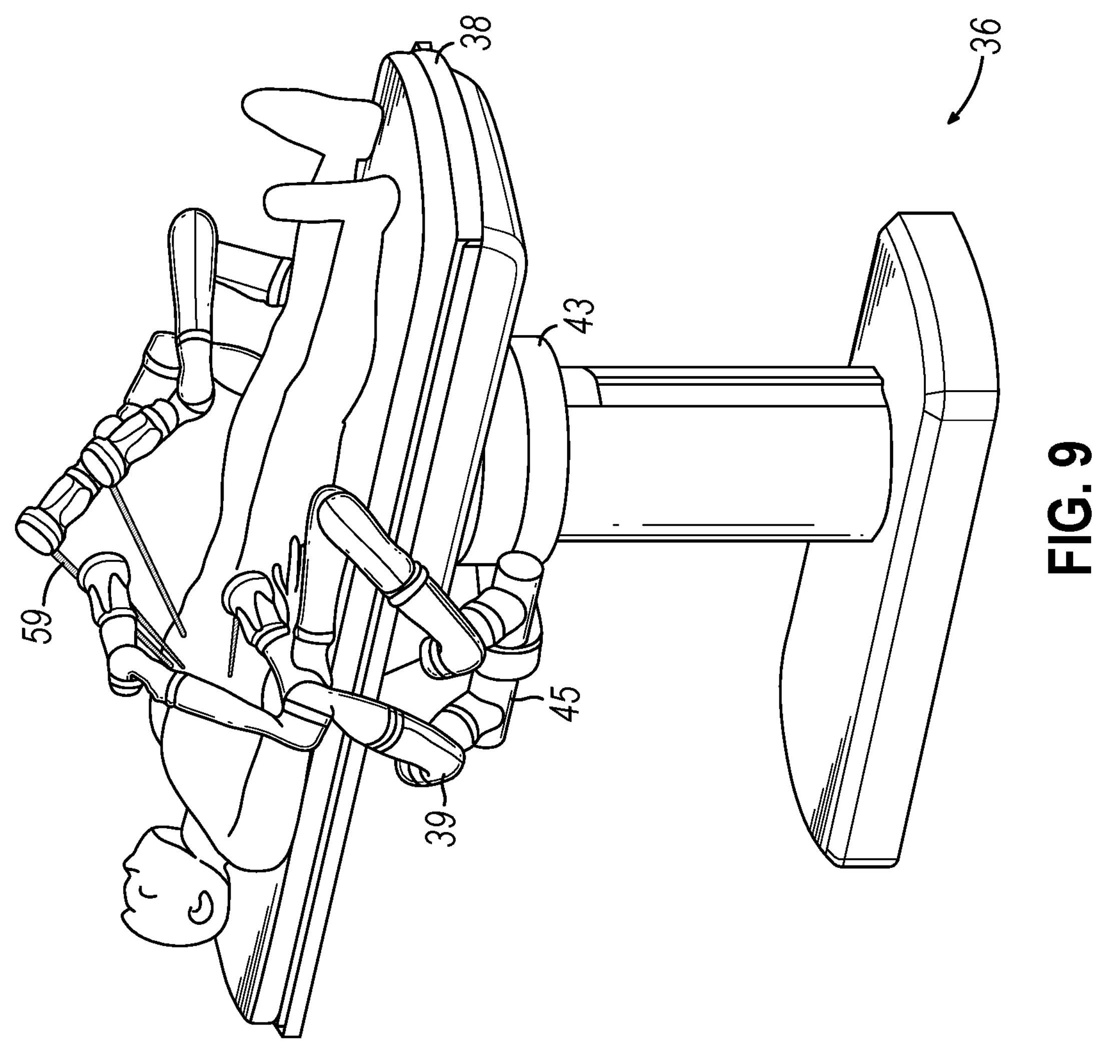
FIG. 9 depicts an embodiment of a table-based robotic system configured for a laparoscopic procedure.

The arms (39) may be mounted on the carriages through a set of arm mounts (45) comprising a series of joints that may individually rotate and/or telescopically extend to provide additional configurability to the robotic arms (39). Additionally, the arm mounts (45) may be positioned on the carriages (43) such that, when the carriages (43) are appropriately rotated, the arm mounts (45) may be positioned on either the same side of table (38) (as shown in FIG. 6), on opposite sides of table (38) (as shown in FIG. 9), or on adjacent sides of the table (38) (not shown).

The column (37) structurally provides support for the table (38), and a path for vertical translation of the carriages. Internally, the column (37) may be equipped with lead screws for guiding vertical translation of the carriages, and motors to mechanize the translation of said carriages based the lead screws. The column (37) may also convey power and control signals to the carriage (43) and robotic arms (39) mounted thereon.

The table base (46) serves a similar function as the cart base (15) in cart (11) shown in FIG. 2, housing heavier components to balance the table/bed (38), the column (37), the carriages (43), and the robotic arms (39). The table base (46) may also incorporate rigid casters to provide stability during procedures. Deployed from the bottom of the table base (46), the casters may extend in opposite directions on both sides of the base (46) and retract when the system (36) needs to be moved.

Continuing with FIG. 6, the system (36) may also include a tower (not shown) that divides the functionality of System (36) between table and tower to reduce the form factor and bulk of the table. As in earlier disclosed embodiments, the tower may provide a variety of support functionalities to table, such as processing, computing, and control capabilities, power, fluidics, and/or optical and sensor processing. The tower may also be movable to be positioned away from the patient to improve physician access and de-clutter the operating room. Additionally, placing components in the tower allows for more storage space in the table base for potential stowage of the robotic arms. The tower may also include a master controller or console that provides both a user interface for user input, such as keyboard and/or pendant, as well as a display screen (or touchscreen) for pre-operative and intra-operative information, such as real-time imaging, navigation, and tracking information. In some embodiments, the tower may also contain holders for gas tanks to be used for insufflation.

Figure 7:
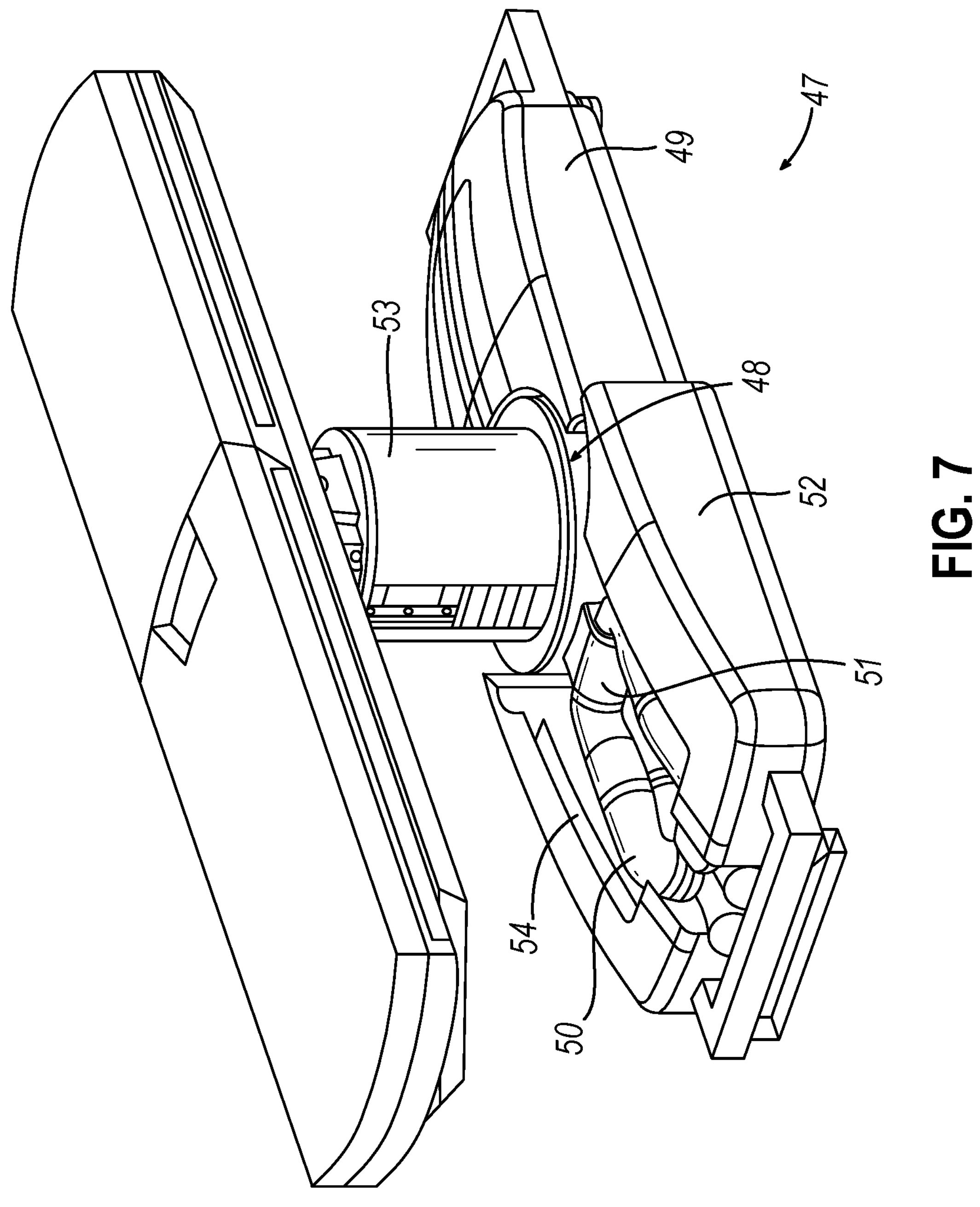
FIG. 7 depicts an example system configured to stow robotic arm(s).

In some embodiments, a table base may stow and store the robotic arms when not in use. FIG. 7 illustrates a system (47) that stows robotic arms in an embodiment of the table-based system. In system (47), carriages (48) may be vertically translated into base (49) to stow robotic arms (50), arm mounts (51), and the carriages (48) within the base (49). Base covers (52) may be translated and retracted open to deploy the carriages (48), arm mounts (51), and arms (50) around column (53), and closed to stow to protect them when not in use. The base covers (52) may be sealed with a membrane (54) along the edges of its opening to prevent dirt and fluid ingress when closed.

Figure 8:
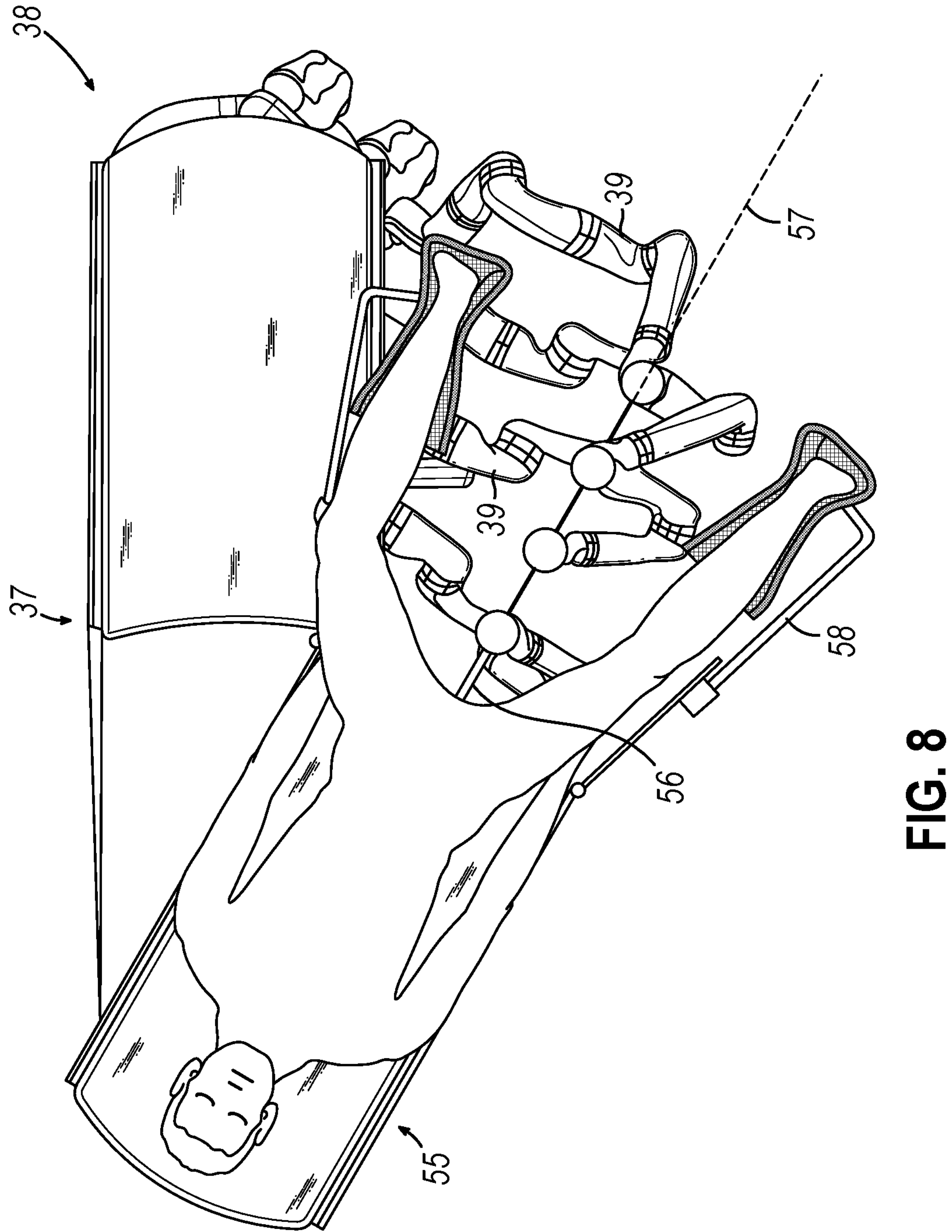
FIG. 8 depicts an embodiment of a table-based robotic system configured for a ureteroscopy procedure.

FIG. 8 illustrates an embodiment of a robotically-enabled table-based system configured for a ureteroscopy procedure. In a ureteroscopy, the table (38) may include a swivel portion (55) for positioning a patient off-angle from the column (37) and table base (46). The swivel portion (55) may rotate or pivot around a pivot point (e.g., located below the patient's head) in order to position the bottom portion of the swivel portion (55) away from the column (37). For example, the pivoting of the swivel portion (55) allows a C-arm (not shown) to be positioned over the patient's lower abdomen without competing for space with the column (not shown) below table (38). By rotating the carriage (35) (not shown) around the column (37), the robotic arms (39) may directly insert a ureteroscope (56) along a virtual rail (57) into the patient's groin area to reach the urethra. In a ureteroscopy, stirrups (58) may also be fixed to the swivel portion (55) of the table (38) to support the position of the patient's legs during the procedure and allow clear access to the patient's groin area.

In a laparoscopic procedure, through small incision(s) in the patient's abdominal wall, minimally invasive instruments may be inserted into the patient's anatomy. In some embodiments, the minimally invasive instruments comprise an elongated rigid member, such as a shaft, which is used to access anatomy within the patient. After inflation of the patient's abdominal cavity, the instruments may be directed to perform surgical or medical tasks, such as grasping, cutting, ablating, suturing, etc. In some embodiments, the instruments can comprise a scope, such as a laparoscope. FIG. 9 illustrates an embodiment of a robotically-enabled table-based system configured for a laparoscopic procedure. As shown in FIG. 9, the carriages (43) of the system (36) may be rotated and vertically adjusted to position pairs of the robotic arms (39) on opposite sides of the table (38), such that instrument (59) may be positioned using the arm mounts (45) to be passed through minimal incisions on both sides of the patient to reach his/her abdominal cavity.

Figure 10:
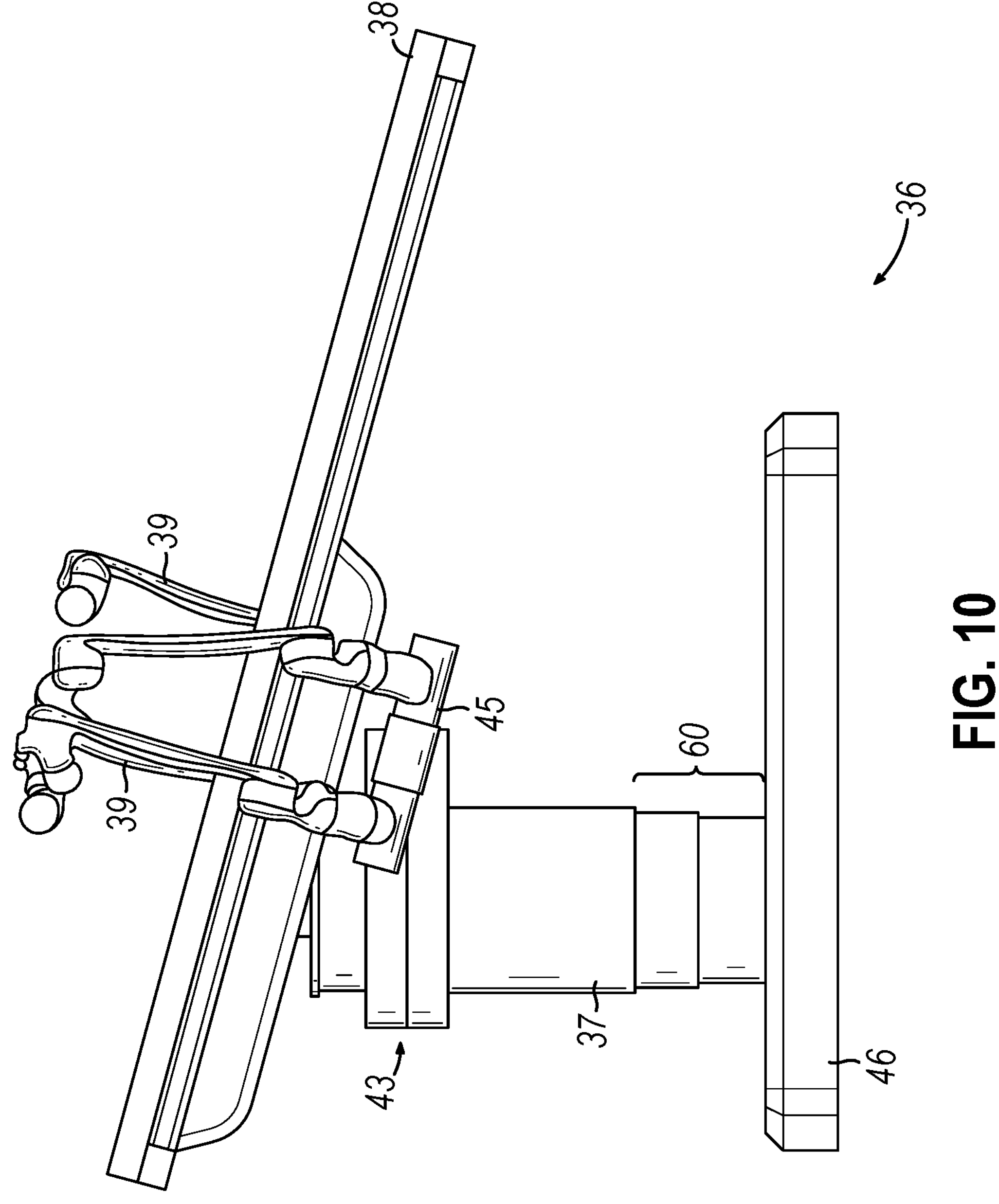
FIG. 10 depicts an embodiment of the table-based robotic system of FIGS. 5-9 with pitch or tilt adjustment.

To accommodate laparoscopic procedures, the robotically-enabled table system may also tilt the platform to a desired angle. FIG. 10 illustrates an embodiment of the robotically-enabled medical system with pitch or tilt adjustment. As shown in FIG. 10, the system (36) may accommodate tilt of the table (38) to position one portion of the table at a greater distance from the floor than the other. Additionally, the arm mounts (45) may rotate to match the tilt such that the arms (39) maintain the same planar relationship with table (38). To accommodate steeper angles, the column (37) may also include telescoping portions (60) that allow vertical extension of column (37) to keep the table (38) from touching the floor or colliding with base (46).

Figure 11:
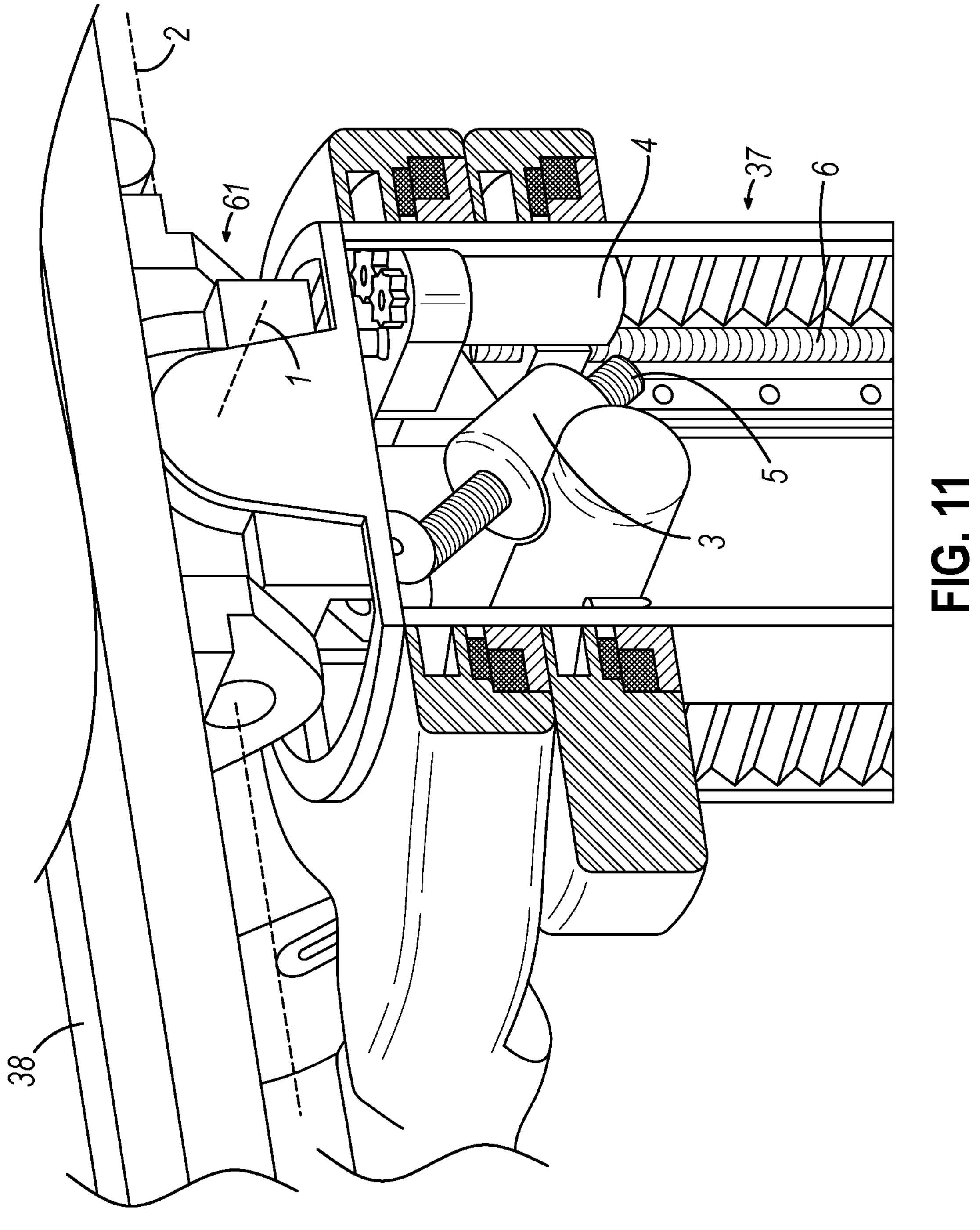
FIG. 11 provides a detailed illustration of the interface between the table and the column of the table-based robotic system of FIGS. 5-10.

FIG. 11 provides a detailed illustration of the interface between the table (38) and the column (37). Pitch rotation mechanism (61) may be configured to alter the pitch angle of the table (38) relative to the column (37) in multiple degrees of freedom. The pitch rotation mechanism (61) may be enabled by the positioning of orthogonal axes (1, 2) at the column-table interface, each axis actuated by a separate motor (3, 4) responsive to an electrical pitch angle command. Rotation along one screw (5) would enable tilt adjustments in one axis (1), while rotation along the other screw (6) would enable tilt adjustments along the other axis (2). In some embodiments, a ball joint can be used to alter the pitch angle of the table (38) relative to the column (37) in multiple degrees of freedom.

For example, pitch adjustments are particularly useful when trying to position the table in a Trendelenburg position, i.e., position the patient's lower abdomen at a higher position from the floor than the patient's lower abdomen, for lower abdominal surgery. The Trendelenburg position causes the patient's internal organs to slide towards his/her upper abdomen through the force of gravity, clearing out the abdominal cavity for minimally invasive tools to enter and perform lower abdominal surgical or medical procedures, such as laparoscopic prostatectomy.

Figure 12:
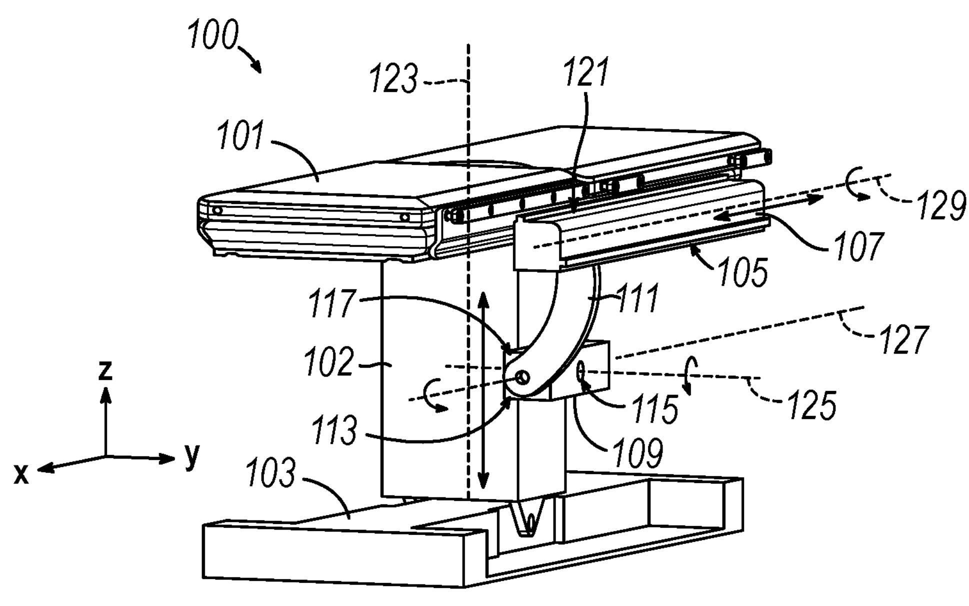
FIG. 12 depicts an alternative version of a table-based robotic system.
Figure 13:
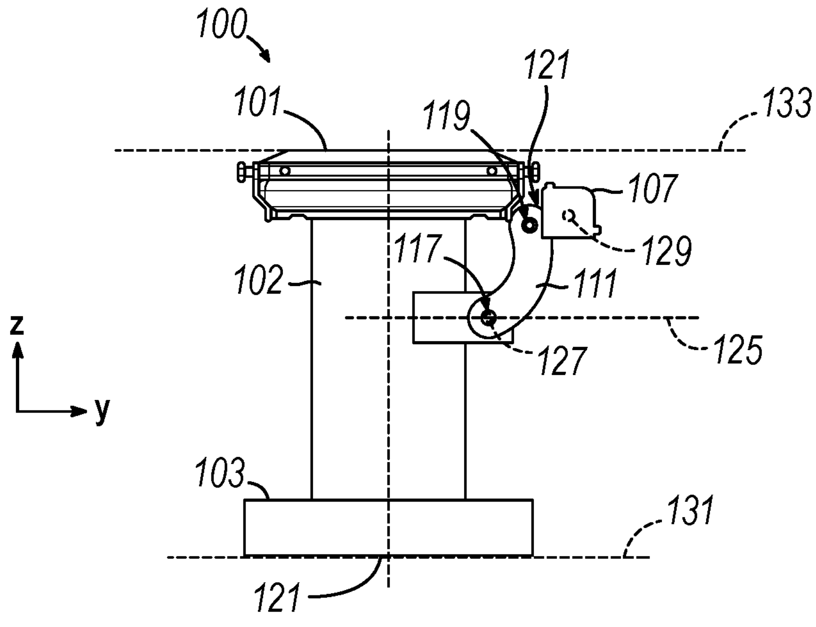
FIG. 13 depicts an end view of the table-based robotic system of FIG. 12.

FIGS. 12 and 13 illustrate isometric and end views of an alternative version of a table-based surgical robotics system (100). The surgical robotics system (100) includes one or more adjustable arm supports (105) that can be configured to support one or more robotic arms (see, for example, FIG. 14) relative to a table (101). In the illustrated embodiment, a single adjustable arm support (105) is shown, though an additional arm support can be provided on an opposite side of the table (101). The adjustable arm support (105) can be configured so that it can move relative to the table (101) to adjust and/or vary the position of the adjustable arm support (105) and/or any robotic arms mounted thereto relative to the table (101). For example, the adjustable arm support (105) may be adjusted one or more degrees of freedom relative to the table (101). The adjustable arm support (105) provides high versatility to the system (100), including the ability to easily stow the one or more adjustable arm supports (105) and any robotics arms attached thereto beneath the table (101). The adjustable arm support (105) can be elevated from the stowed position to a position below an upper surface of the table (101). In other embodiments, the adjustable arm support (105) can be elevated from the stowed position to a position above an upper surface of the table (101).

The adjustable arm support (105) can provide several degrees of freedom, including lift, lateral translation, tilt, etc. In the illustrated embodiment of FIGS. 12 and 13, the arm support (105) is configured with four degrees of freedom, which are illustrated with arrows in FIG. 12. A first degree of freedom allows for adjustment of the adjustable arm support (105) in the z-direction ("Z-lift"). For example, the adjustable arm support (105) can include a carriage (109) configured to move up or down along or relative to a column (102) supporting the table (101). A second degree of freedom can allow the adjustable arm support (105) to tilt. For example, the adjustable arm support (105) can include a rotary joint, which can allow the adjustable arm support (105) to be aligned with the bed in a Trendelenburg position. A third degree of freedom can allow the adjustable arm support (105) to "pivot up," which can be used to adjust a distance between a side of the table (101) and the adjustable arm support (105). A fourth degree of freedom can permit translation of the adjustable arm support (105) along a longitudinal length of the table.

The surgical robotics system (100) in FIGS. 12 and 13 can comprise a table supported by a column (102) that is mounted to a base (103). The base (103) and the column (102) support the table (101) relative to a support surface. A floor axis (131) and a support axis (133) are shown in FIG. 13.

The adjustable arm support (105) can be mounted to the column (102). In other embodiments, the arm support (105) can be mounted to the table (101) or base (103). The adjustable arm support (105) can include a carriage (109), a bar or rail connector (111) and a bar or rail (107). In some embodiments, one or more robotic arms mounted to the rail (107) can translate and move relative to one another.

The carriage (109) can be attached to the column (102) by a first joint (113), which allows the carriage (109) to move relative to the column (102) (e.g., such as up and down a first or vertical axis 123). The first joint (113) can provide the first degree of freedom ("Z-lift") to the adjustable arm support (105). The adjustable arm support (105) can include a second joint 115, which provides the second degree of freedom (tilt) for the adjustable arm support (105). The adjustable arm support (105) can include a third joint (117), which can provide the third degree of freedom ("pivot up") for the adjustable arm support (105). An additional joint (119) (shown in FIG. 13) can be provided that mechanically constrains the third joint (117) to maintain an orientation of the rail (107) as the rail connector (111) is rotated about a third axis (127). The adjustable arm support (105) can include a fourth joint (121), which can provide a fourth degree of freedom (translation) for the adjustable arm support (105) along a fourth axis (129).

Figure 14:
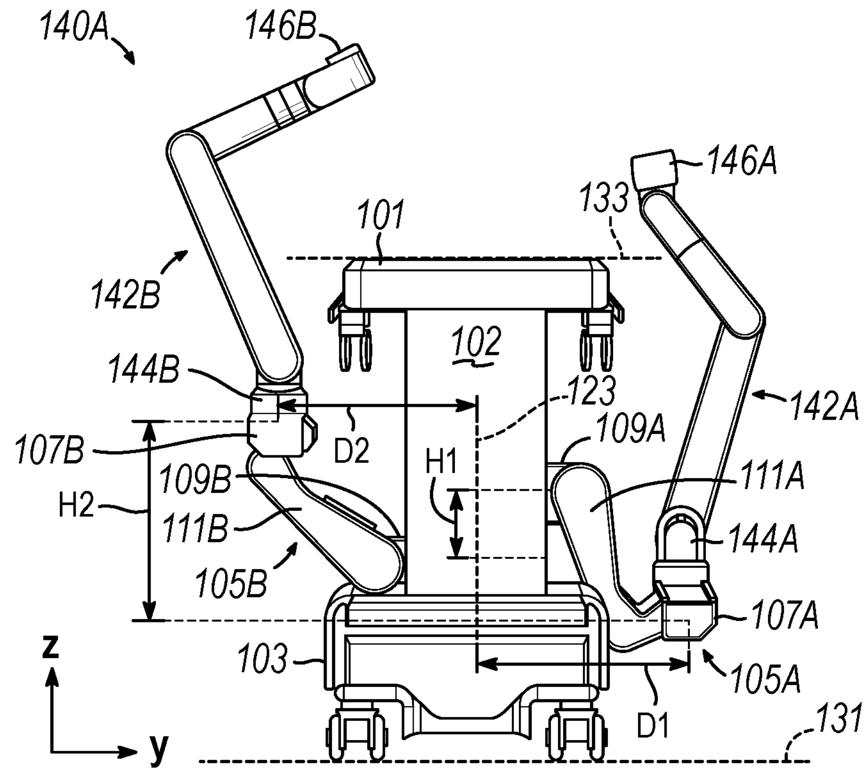
FIG. 14 depicts an end view of a table-based robotic system with robotic arms attached thereto.

FIG. 14 illustrates an end view of the surgical robotics system (140A) with two adjustable arm supports (105A, 105B) mounted on opposite sides of a table (101). A first robotic arm (142A) is attached to the bar or rail (107A) of the first adjustable arm support (105B). The first robotic arm (142A) includes a base (144A) attached to the rail (107A). The distal end of the first robotic arm (142A) includes an instrument drive mechanism (146A) that can attach to one or more robotic medical instruments or tools. Similarly, the second robotic arm (142B) includes a base (144B) attached to the rail (107B). The distal end of the second robotic arm (142B) includes an instrument drive mechanism (146B). The instrument drive mechanism (146B) can be configured to attach to one or more robotic medical instruments or tools.

In some embodiments, one or more of the robotic arms (142A, 142B) comprises an arm with seven or more degrees of freedom. In some embodiments, one or more of the robotic arms (142A, 142B) can include eight degrees of freedom, including an insertion axis (1-degree of freedom including insertion), a wrist (3-degrees of freedom including wrist pitch, yaw and roll), an elbow (1-degree of freedom including elbow pitch), a shoulder (2-degrees of freedom including shoulder pitch and yaw), and base (144A, 144B) (1-degree of freedom including translation). In some embodiments, the insertion degree of freedom can be provided by the robotic arm (142A, 142B), while in other embodiments, the instrument itself provides insertion via an instrument-based insertion architecture.

C. Example of Robotic System Instrument Driver & Interface

The end effectors of the system's robotic arms comprise (i) an instrument driver (alternatively referred to as "instrument drive mechanism" or "instrument device manipulator") that incorporate electro-mechanical means for actuating the medical instrument and (ii) a removable or detachable medical instrument, which may be devoid of any electro-mechanical components, such as motors. This dichotomy may be driven by the need to sterilize medical instruments used in medical procedures, and the inability to adequately sterilize expensive capital equipment due to their intricate mechanical assemblies and sensitive electronics. Accordingly, the medical instruments may be designed to be detached, removed, and interchanged from the instrument driver (and thus the system) for individual sterilization or disposal by the physician or the physician's staff. In contrast, the instrument drivers need not be changed or sterilized, and may be draped for protection.

Figure 15:
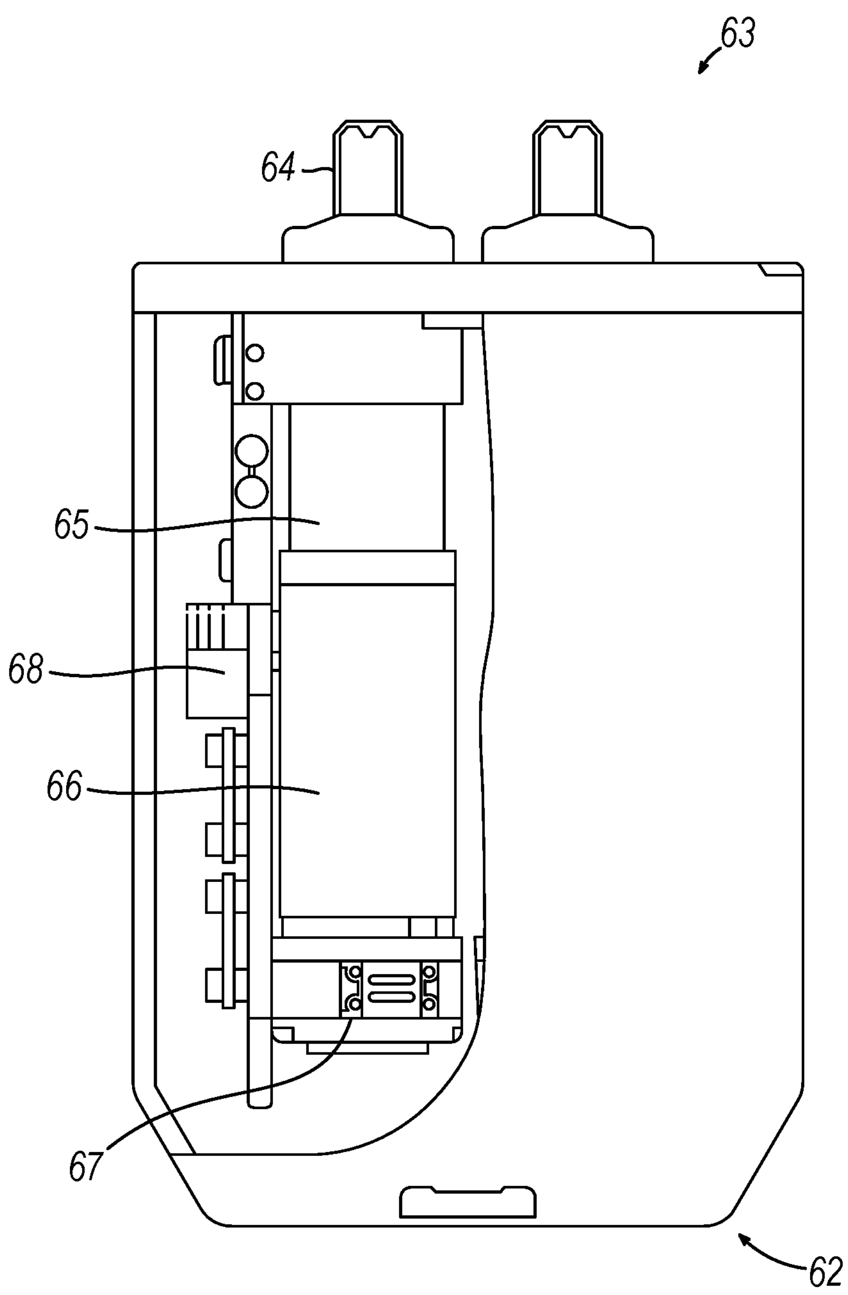
FIG. 15 depicts an exemplary instrument driver.

FIG. 15 illustrates an example instrument driver. Positioned at the distal end of a robotic arm, instrument driver (62) comprises of one or more drive units (63) arranged with parallel axes to provide controlled torque to a medical instrument via drive shafts (64). Each drive unit (63) comprises an individual drive shaft (64) for interacting with the instrument, a gear head (65) for converting the motor shaft rotation to a desired torque, a motor (66) for generating the drive torque, an encoder (67) to measure the speed of the motor shaft and provide feedback to the control circuitry, and control circuitry (68) for receiving control signals and actuating the drive unit. Each drive unit (63) being independent controlled and motorized, the instrument driver (62) may provide multiple (four as shown in FIG. 15) independent drive outputs to the medical instrument. In operation, the control circuitry (68) would receive a control signal, transmit a motor signal to the motor (66), compare the resulting motor speed as measured by the encoder (67) with the desired speed, and modulate the motor signal to generate the desired torque.

For procedures that require a sterile environment, the robotic system may incorporate a drive interface, such as a sterile adapter connected to a sterile drape, that sits between the instrument driver and the medical instrument. The chief purpose of the sterile adapter is to transfer angular motion from the drive shafts of the instrument driver to the drive inputs of the instrument while maintaining physical separation, and thus sterility, between the drive shafts and drive inputs. Accordingly, an example sterile adapter may comprise of a series of rotational inputs and outputs intended to be mated with the drive shafts of the instrument driver and drive inputs on the instrument. Connected to the sterile adapter, the sterile drape, comprised of a thin, flexible material such as transparent or translucent plastic, is designed to cover the capital equipment, such as the instrument driver, robotic arm, and cart (in a cart-based system) or table (in a table-based system). Use of the drape would allow the capital equipment to be positioned proximate to the patient while still being located in an area not requiring sterilization (i.e., non-sterile field). On the other side of the sterile drape, the medical instrument may interface with the patient in an area requiring sterilization (i.e., sterile field).

D. Example of Robotic System Medical Instrument

Figure 16:
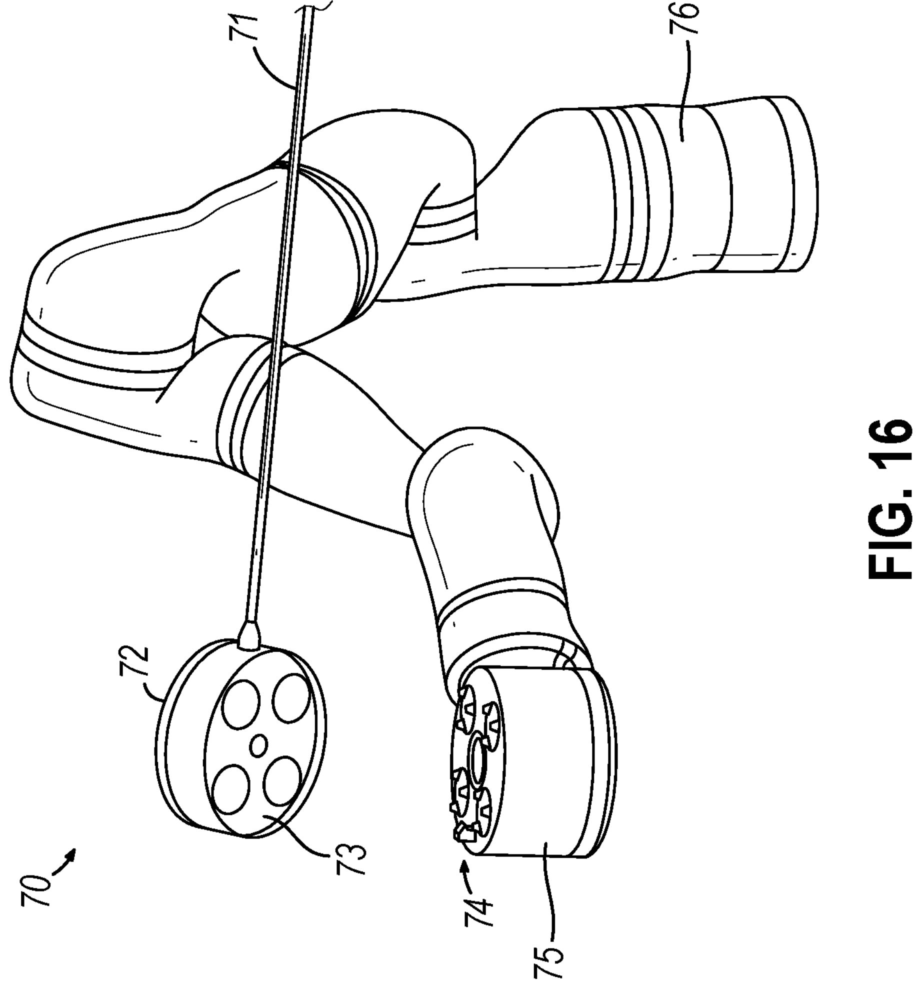
FIG. 16 depicts an exemplary medical instrument with a paired instrument driver.

FIG. 16 illustrates an example medical instrument with a paired instrument driver. Like other instruments designed for use with a robotic system, medical instrument (70) comprises an elongated shaft (71) (or elongate body) and an instrument base (72). The instrument base (72), also referred to as an "instrument handle" due to its intended design for manual interaction by the physician, may generally comprise rotatable drive inputs (73), e.g., receptacles, pulleys or spools, that are designed to be mated with drive outputs (74) that extend through a drive interface on instrument driver (75) at the distal end of robotic arm (76). When physically connected, latched, and/or coupled, the mated drive inputs (73) of instrument base (72) may share axes of rotation with the drive outputs (74) in the instrument driver (75) to allow the transfer of torque from drive outputs (74) to drive inputs (73). In some embodiments, the drive outputs (74) may comprise splines that are designed to mate with receptacles on the drive inputs (73).

The elongated shaft (71) is designed to be delivered through either an anatomical opening or lumen, e.g., as in endoscopy, or a minimally invasive incision, e.g., as in laparoscopy. The elongated shaft (71) may be either flexible (e.g., having properties similar to an endoscope) or rigid (e.g., having properties similar to a laparoscope) or contain a customized combination of both flexible and rigid portions. When designed for laparoscopy, the distal end of a rigid elongated shaft may be connected to an end effector extending from a jointed wrist formed from a clevis with at least one degree of freedom and a surgical tool or medical instrument, such as, for example, a grasper or scissors, that may be actuated based on force from the tendons as the drive inputs rotate in response to torque received from the drive outputs (74) of the instrument driver (75). When designed for endoscopy, the distal end of a flexible elongated shaft may include a steerable or controllable bending section that may be articulated and bent based on torque received from the drive outputs (74) of the instrument driver (75).

Torque from the instrument driver (75) is transmitted down the elongated shaft (71) using tendons along the shaft (71). These individual tendons, such as pull wires, may be individually anchored to individual drive inputs (73) within the instrument handle (72). From the handle (72), the tendons are directed down one or more pull lumens along the elongated shaft (71) and anchored at the distal portion of the elongated shaft (71), or in the wrist at the distal portion of the elongated shaft. During a surgical procedure, such as a laparoscopic, endoscopic or hybrid procedure, these tendons may be coupled to a distally mounted end effector, such as a wrist, grasper, or scissor. Under such an arrangement, torque exerted on drive inputs (73) would transfer tension to the tendon, thereby causing the end effector to actuate in some way. In some embodiments, during a surgical procedure, the tendon may cause a joint to rotate about an axis, thereby causing the end effector to move in one direction or another. Alternatively, the tendon may be connected to one or more jaws of a grasper at distal end of the elongated shaft (71), where tension from the tendon cause the grasper to close.

In endoscopy, the tendons may be coupled to a bending or articulating section positioned along the elongated shaft (71) (e.g., at the distal end) via adhesive, control ring, or other mechanical fixation. When fixedly attached to the distal end of a bending section, torque exerted on drive inputs (73) would be transmitted down the tendons, causing the softer, bending section (sometimes referred to as the articulable section or region) to bend or articulate. Along the non-bending sections, it may be advantageous to spiral or helix the individual pull lumens that direct the individual tendons along (or inside) the walls of the endoscope shaft to balance the radial forces that result from tension in the pull wires. The angle of the spiraling and/or spacing there between may be altered or engineered for specific purposes, wherein tighter spiraling exhibits lesser shaft compression under load forces, while lower amounts of spiraling results in greater shaft compression under load forces, but also exhibits limits bending. On the other end of the spectrum, the pull lumens may be directed parallel to the longitudinal axis of the elongated shaft (71) to allow for controlled articulation in the desired bending or articulable sections.

In endoscopy, the elongated shaft (71) houses a number of components to assist with the robotic procedure. The shaft may comprise of a working channel for deploying surgical tools (or medical instruments), irrigation, and/or aspiration to the operative region at the distal end of the shaft (71). The shaft (71) may also accommodate wires and/or optical fibers to transfer signals to/from an optical assembly at the distal tip, which may include of an optical camera. The shaft (71) may also accommodate optical fibers to carry light from proximally-located light sources, such as light emitting diodes, to the distal end of the shaft.

At the distal end of the instrument (70), the distal tip may also comprise the opening of a working channel for delivering tools for diagnostic and/or therapy, irrigation, and aspiration to an operative site. The distal tip may also include a port for a camera, such as a fiberscope or a digital camera, to capture images of an internal anatomical space. Relatedly, the distal tip may also include ports for light sources for illuminating the anatomical space when using the camera.

In the example of FIG. 16, the drive shaft axes, and thus the drive input axes, are orthogonal to the axis of the elongated shaft. This arrangement, however, complicates roll capabilities for the elongated shaft (71). Rolling the elongated shaft (71) along its axis while keeping the drive inputs (73) static results in undesirable tangling of the tendons as they extend off the drive inputs (73) and enter pull lumens within the elongated shaft (71). The resulting entanglement of such tendons may disrupt any control algorithms intended to predict movement of the flexible elongated shaft during an endoscopic procedure.

Figure 17:
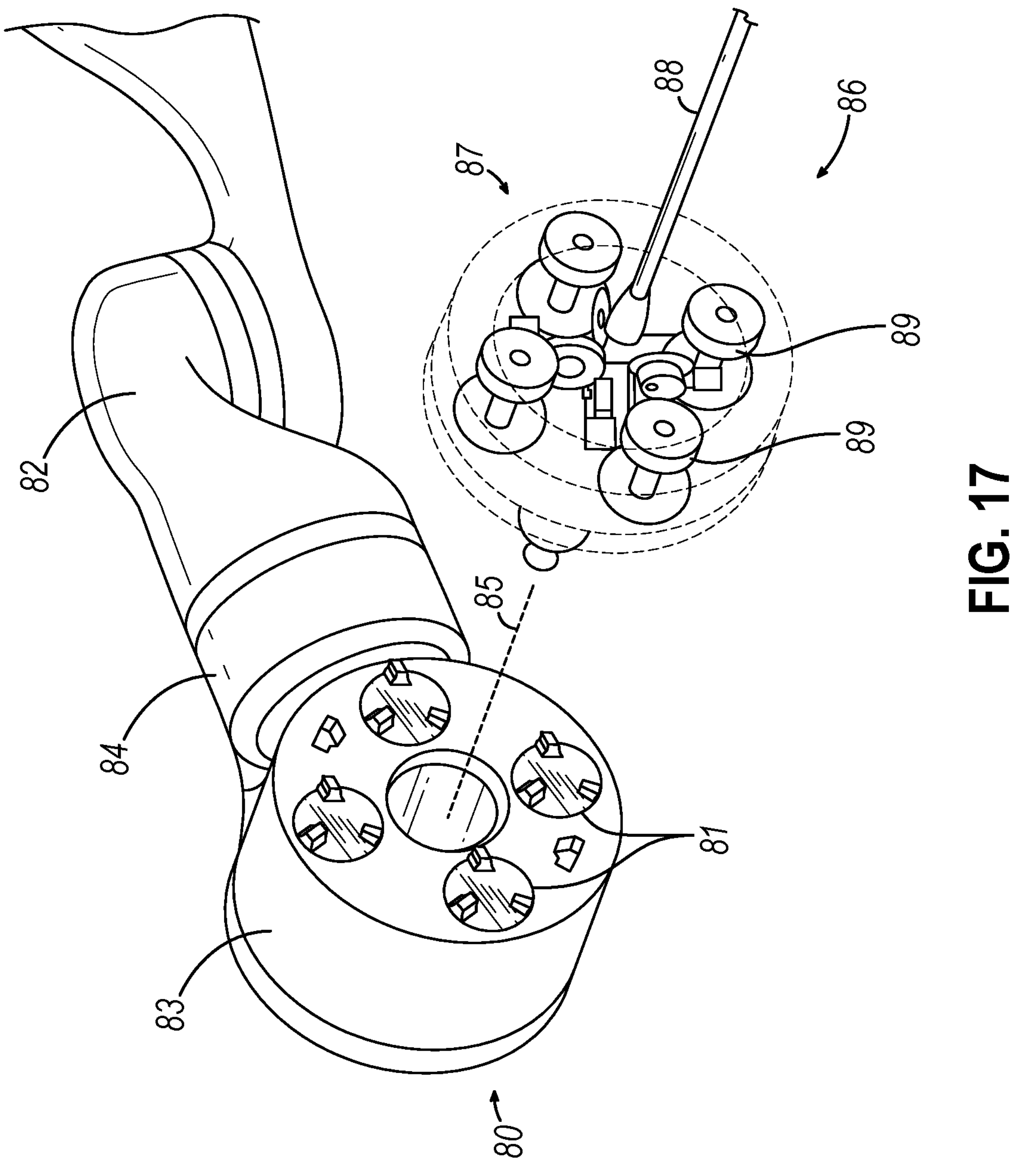
FIG. 17 depicts an alternative design for an instrument driver and instrument where the axes of the drive units are parallel to the axis of the elongated shaft of the instrument.

FIG. 17 illustrates an alternative design for an instrument driver and instrument where the axes of the drive units are parallel to the axis of the elongated shaft of the instrument. As shown, a circular instrument driver (80) comprises four drive units with their drive outputs (81) aligned in parallel at the end of a robotic arm (82). The drive units, and their respective drive outputs (81), are housed in a rotational assembly (83) of the instrument driver (80) that is driven by one of the drive units within the assembly (83). In response to torque provided by the rotational drive unit, the rotational assembly (83) rotates along a circular bearing that connects the rotational assembly (83) to the non-rotational portion (84) of the instrument driver. Power and controls signals may be communicated from the non-rotational portion (84) of the instrument driver (80) to the rotational assembly (83) through electrical contacts may be maintained through rotation by a brushed slip ring connection (not shown). In other embodiments, the rotational assembly (83) may be responsive to a separate drive unit that is integrated into the non-rotatable portion (84), and thus not in parallel to the other drive units. The rotational assembly (83) allows the instrument driver (80) to rotate the drive units, and their respective drive outputs (81), as a single unit around an instrument driver axis (85).

Like earlier disclosed embodiments, an instrument 86 may comprise an elongated shaft portion (88) and an instrument base (87) (shown with a transparent external skin for discussion purposes) comprising a plurality of drive inputs (89) (such as receptacles, pulleys, and spools) that are configured to receive the drive outputs (81) in the instrument driver (80). Unlike prior disclosed embodiments, instrument shaft (88) extends from the center of instrument base (87) with an axis substantially parallel to the axes of the drive inputs (89), rather than orthogonal as in the design of FIG. 16.

When coupled to the rotational assembly (83) of the instrument driver (80), the medical instrument 86, comprising instrument base (87) and instrument shaft (88), rotates in combination with the rotational assembly (83) about the instrument driver axis (85). Since the instrument shaft (88) is positioned at the center of instrument base (87), the instrument shaft (88) is coaxial with instrument driver axis (85) when attached. Thus, rotation of the rotational assembly (83) causes the instrument shaft (88) to rotate about its own longitudinal axis. Moreover, as the instrument base (87) rotates with the instrument shaft (88), any tendons connected to the drive inputs (89) in the instrument base (87) are not tangled during rotation. Accordingly, the parallelism of the axes of the drive outputs (81), drive inputs (89), and instrument shaft (88) allows for the shaft rotation without tangling any control tendons.

Figure 18:
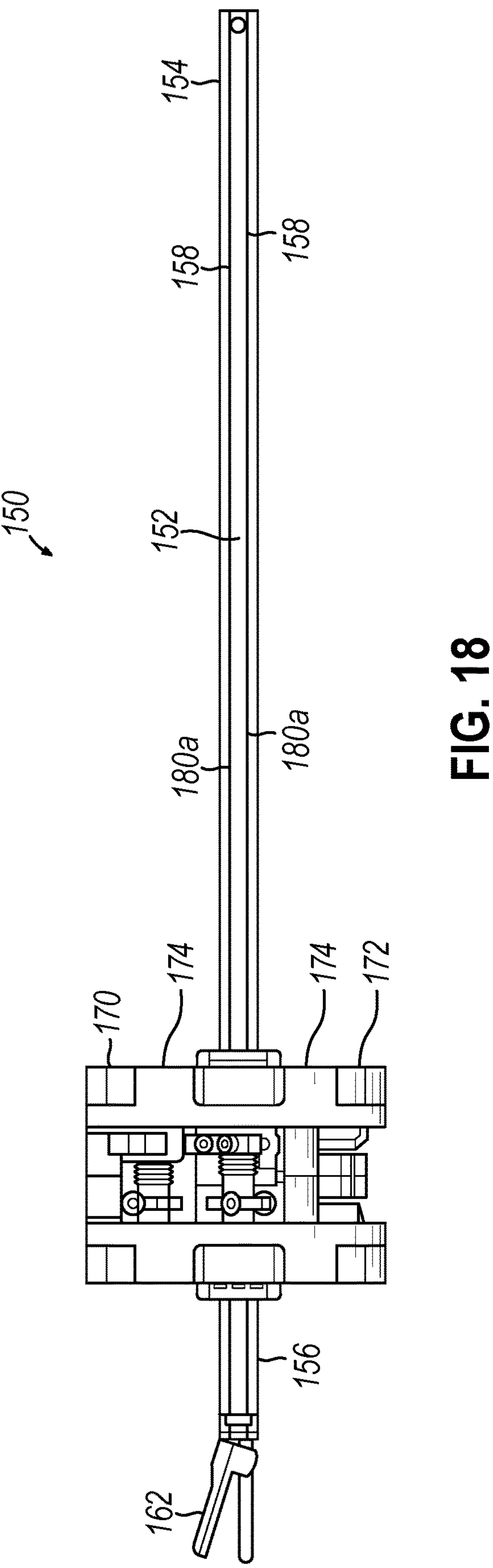
FIG. 18 depicts an instrument having an instrument-based insertion architecture.

FIG. 18 illustrates an instrument having an instrument based insertion architecture in accordance with some embodiments. The instrument (150) can be coupled to any of the instrument drivers discussed above. The instrument (150) comprises an elongated shaft (152), an end effector (162) connected to the shaft (152), and a handle (170) coupled to the shaft (152). The elongated shaft (152) comprises a tubular member having a proximal portion (154) and a distal portion (156). The elongated shaft (152) comprises one or more channels or grooves (158) along its outer surface. The grooves (158) are configured to receive one or more wires or cables (180) therethrough. One or more cables (180) thus run along an outer surface of the elongated shaft (152). In other embodiments, cables (180) can also run through the elongated shaft (152). Manipulation of the one or more cables (180) (e.g., via an instrument driver) results in actuation of the end effector (162).

The instrument handle (170), which may also be referred to as an instrument base, may generally comprise an attachment interface (172) having one or more mechanical inputs (174), e.g., receptacles, pulleys or spools, that are designed to be reciprocally mated with one or more torque couplers on an attachment surface of an instrument driver.

In some embodiments, the instrument (150) comprises a series of pulleys or cables that enable the elongated shaft (152) to translate relative to the handle (170). In other words, the instrument (150) itself comprises an instrument-based insertion architecture that accommodates insertion of the instrument, thereby minimizing the reliance on a robot arm to provide insertion of the instrument (150). In other embodiments, a robotic arm can be largely responsible for instrument insertion.

E. Example of Robotic System Controller

Any of the robotic systems described herein can include an input device or controller for manipulating an instrument attached to a robotic arm. In some embodiments, the controller can be coupled (e.g., communicatively, electronically, electrically, wirelessly and/or mechanically) with an instrument such that manipulation of the controller causes a corresponding manipulation of the instrument e.g., via master slave control.

Figure 19:
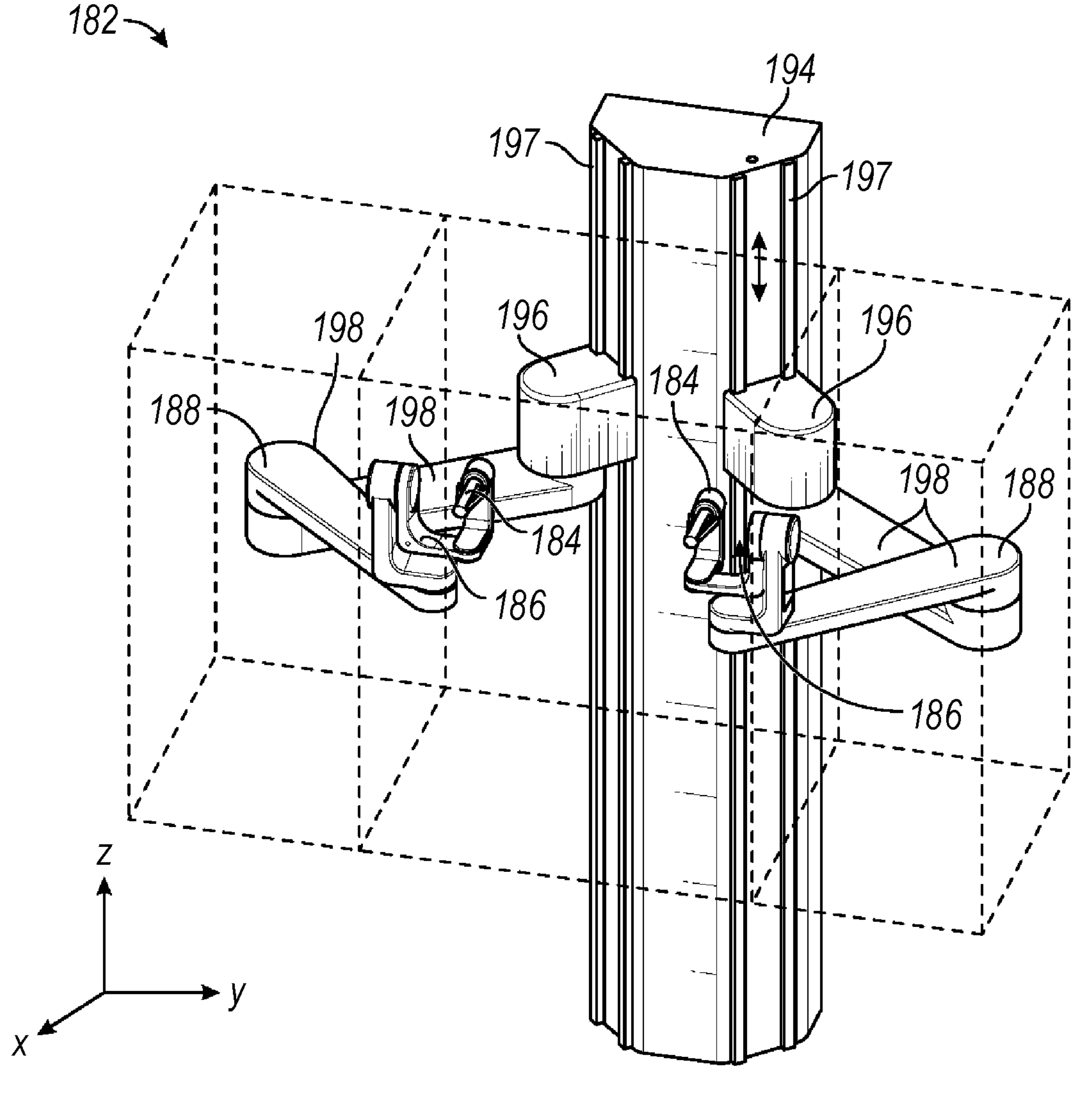
FIG. 19 depicts an exemplary controller.

FIG. 19 is a perspective view of an embodiment of a controller (182). In the present embodiment, the controller (182) comprises a hybrid controller that can have both impedance and admittance control. In other embodiments, the controller (182) can utilize just impedance or passive control. In other embodiments, the controller (182) can utilize just admittance control. By being a hybrid controller, the controller (182) advantageously can have a lower perceived inertia while in use.

In the illustrated embodiment, the controller (182) is configured to allow manipulation of two medical instruments, and includes two handles (184). Each of the handles (184) is connected to a gimbal (186). Each gimbal (186) is connected to a positioning platform (188).

As shown in FIG. 19, each positioning platform (188) includes a SCARA arm (selective compliance assembly robot arm) (198) coupled to a column (194) by a prismatic joint (196). The prismatic joints (196) are configured to translate along the column (194) (e.g., along rails (197)) to allow each of the handles (184) to be translated in the z-direction, providing a first degree of freedom. The SCARA arm (198) is configured to allow motion of the handle (184) in an x-y plane, providing two additional degrees of freedom.

In some embodiments, one or more load cells are positioned in the controller. For example, in some embodiments, a load cell (not shown) is positioned in the body of each of the gimbals (186). By providing a load cell, portions of the controller (182) are capable of operating under admittance control, thereby advantageously reducing the perceived inertia of the controller while in use. In some embodiments, the positioning platform (188) is configured for admittance control, while the gimbal (186) is configured for impedance control. In other embodiments, the gimbal (186) is configured for admittance control, while the positioning platform (188) is configured for impedance control. Accordingly, for some embodiments, the translational or positional degrees of freedom of the positioning platform (188) can rely on admittance control, while the rotational degrees of freedom of the gimbal (186) rely on impedance control.

F. Example of Robotic System Navigation and Control

Traditional endoscopy may involve the use of fluoroscopy (e.g., as may be delivered through a C-arm) and other forms of radiation-based imaging modalities to provide endoluminal guidance to an operator physician. In contrast, the robotic systems contemplated by this disclosure can provide for non-radiation-based navigational and localization means to reduce physician exposure to radiation and reduce the amount of equipment within the operating room. As used herein, the term "localization" may refer to determining and/or monitoring the position of objects in a reference coordinate system. Technologies such as pre-operative mapping, computer vision, real-time EM tracking, and robot command data may be used individually or in combination to achieve a radiation-free operating environment. In other cases, where radiation-based imaging modalities are still used, the pre-operative mapping, computer vision, real-time EM tracking, and robot command data may be used individually or in combination to improve upon the information obtained solely through radiation-based imaging modalities.

Figure 20:
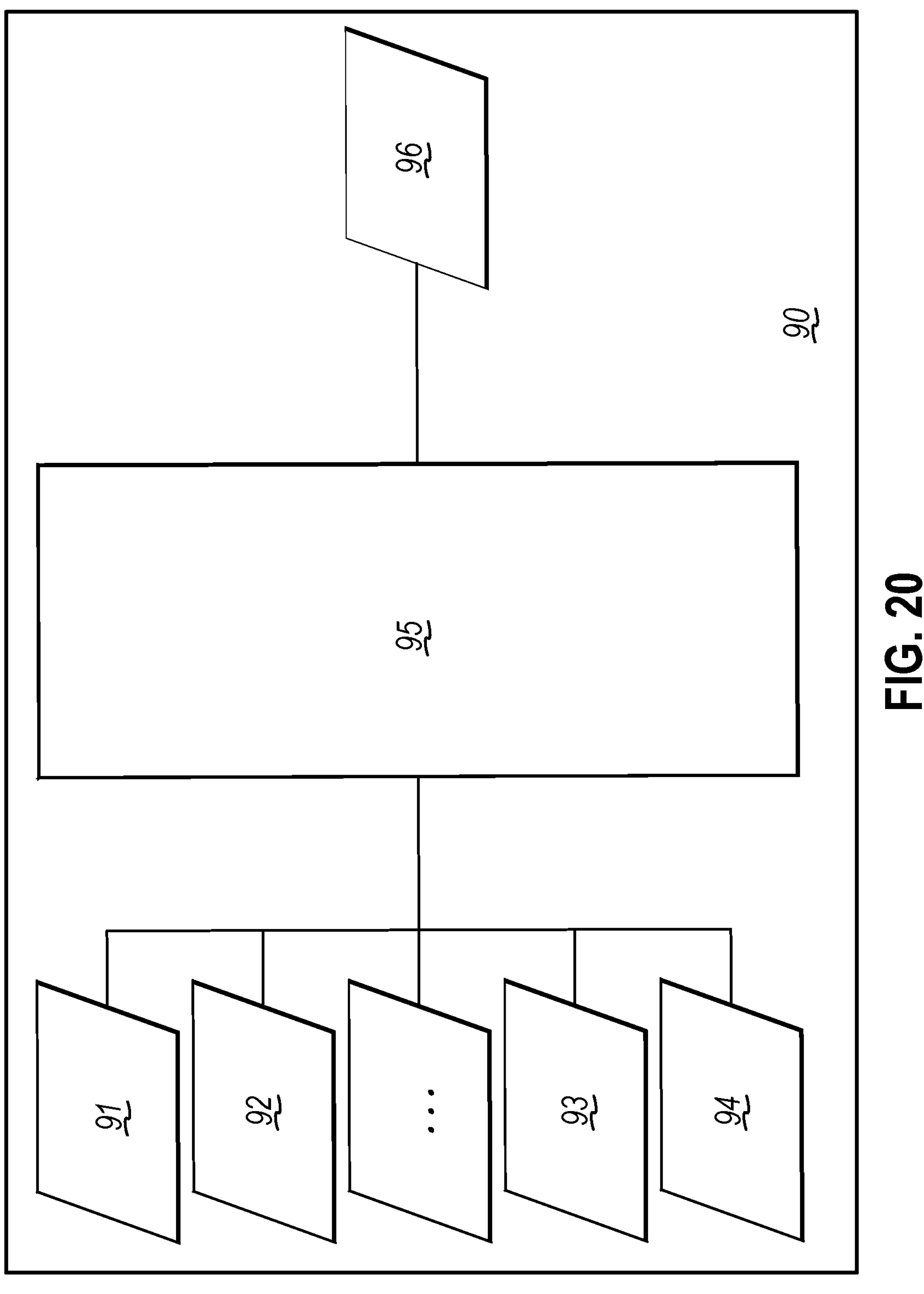
FIG. 20 depicts a block diagram illustrating a localization system that estimates a location of one or more elements of the robotic systems of FIGS. 1-10, such as the location of the instrument of FIGS. 16-18, in accordance to an example embodiment.

FIG. 20 is a block diagram illustrating a localization system (90) that estimates a location of one or more elements of the robotic system, such as the location of the instrument, in accordance to an example embodiment. The localization system (90) may be a set of one or more computer devices configured to execute one or more instructions. The computer devices may be embodied by a processor (or processors) and computer-readable memory in one or more components discussed above. By way of example and not limitation, the computer devices may be in the tower (30) shown in FIG. 1, the cart shown in FIGS. 1-4, the beds shown in FIGS. 5-14, etc.

As shown in FIG. 20, the localization system (90) may include a localization module (95) that processes input data (91-94) to generate location data (96) for the distal tip of a medical instrument. The location data (96) may be data or logic that represents a location and/or orientation of the distal end of the instrument relative to a frame of reference. The frame of reference can be a frame of reference relative to the anatomy of the patient or to a known object, such as an EM field generator (see discussion below for the EM field generator).

The various input data (91-94) are now described in greater detail. Pre-operative mapping may be accomplished through the use of the collection of low dose CT scans. Pre-operative CT scans are reconstructed into three-dimensional images, which are visualized, e.g. as "slices" of a cutaway view of the patient's internal anatomy. When analyzed in the aggregate, image-based models for anatomical cavities, spaces and structures of the patient's anatomy, such as a patient lung network, may be generated. Techniques such as center-line geometry may be determined and approximated from the CT images to develop a three-dimensional volume of the patient's anatomy, referred to as model data (91) (also referred to as "preoperative model data" when generated using only preoperative CT scans). The use of center-line geometry is discussed in U.S. Pat. No. 9,763,741, the contents of which are herein incorporated in its entirety. Network topological models may also be derived from the CT-images, and are particularly appropriate for bronchoscopy.

In some embodiments, the instrument may be equipped with a camera to provide vision data (92). The localization module (95) may process the vision data to enable one or more vision-based location tracking. For example, the pre-operative model data may be used in conjunction with the vision data (92) to enable computer vision-based tracking of the medical instrument (e.g., an endoscope or an instrument advance through a working channel of the endoscope). For example, using the preoperative model data (91), the robotic system may generate a library of expected endoscopic images from the model based on the expected path of travel of the endoscope, each image linked to a location within the model. Intra-operatively, this library may be referenced by the robotic system in order to compare real-time images captured at the camera (e.g., a camera at a distal end of the endoscope) to those in the image library to assist localization.

Other computer vision-based tracking techniques use feature tracking to determine motion of the camera, and thus the endoscope. Some features of the localization module (95) may identify circular geometries in the preoperative model data (91) that correspond to anatomical lumens and track the change of those geometries to determine which anatomical lumen was selected, as well as the relative rotational and/or translational motion of the camera. Use of a topological map may further enhance vision-based algorithms or techniques.

Optical flow, another computer vision-based technique, may analyze the displacement and translation of image pixels in a video sequence in the vision data (92) to infer camera movement. Examples of optical flow techniques may include motion detection, object segmentation calculations, luminance, motion compensated encoding, stereo disparity measurement, etc. Through the comparison of multiple frames over multiple iterations, movement and location of the camera (and thus the endoscope) may be determined.

The localization module (95) may use real-time EM tracking to generate a real-time location of the endoscope in a global coordinate system that may be registered to the patient's anatomy, represented by the preoperative model. In EM tracking, an EM sensor (or tracker) comprising of one or more sensor coils embedded in one or more locations and orientations in a medical instrument (e.g., an endoscopic tool) measures the variation in the EM field created by one or more static EM field generators positioned at a known location. The location information detected by the EM sensors is stored as EM data (93). The EM field generator (or transmitter), may be placed close to the patient to create a low intensity magnetic field that the embedded sensor may detect. The magnetic field induces small currents in the sensor coils of the EM sensor, which may be analyzed to determine the distance and angle between the EM sensor and the EM field generator. These distances and orientations may be intra-operatively "registered" to the patient anatomy (e.g., the preoperative model) in order to determine the geometric transformation that aligns a single location in the coordinate system with a position in the pre-operative model of the patient's anatomy. Once registered, an embedded EM tracker in one or more positions of the medical instrument (e.g., the distal tip of an endoscope) may provide real-time indications of the progression of the medical instrument through the patient's anatomy.

Robotic command and kinematics data (94) may also be used by the localization module (95) to provide localization data (96) for the robotic system. Device pitch and yaw resulting from articulation commands may be determined during pre-operative calibration. Intra-operatively, these calibration measurements may be used in combination with known insertion depth information to estimate the position of the instrument. Alternatively, these calculations may be analyzed in combination with EM, vision, and/or topological modeling to estimate the position of the medical instrument within the network.

As FIG. 20 shows, a number of other input data can be used by the localization module (95). For example, although not shown in FIG. 20, an instrument utilizing shape-sensing fiber can provide shape data that the localization module (95) can use to determine the location and shape of the instrument.

The localization module (95) may use the input data (91-94) in combination(s). In some cases, such a combination may use a probabilistic approach where the localization module (95) assigns a confidence weight to the location determined from each of the input data (91-94). Thus, where the EM data may not be reliable (as may be the case where there is EM interference) the confidence of the location determined by the EM data (93) can be decrease and the localization module (95) may rely more heavily on the vision data (92) and/or the robotic command and kinematics data (94).

As discussed above, the robotic systems discussed herein may be designed to incorporate a combination of one or more of the technologies above. The robotic system's computer-based control system, based in the tower, bed and/or cart, may store computer program instructions, for example, within a non-transitory computer-readable storage medium such as a persistent magnetic storage drive, solid state drive, or the like, that, upon execution, cause the system to receive and analyze sensor data and user commands, generate control signals throughout the system, and display the navigational and localization data, such as the position of the instrument within the global coordinate system, anatomical map, etc.

II. Example of Robotically Controlled Uterine Manipulator

In some conventional hysterectomy procedures, a first clinician may serve in a role of forming incisions and performing other laparoscopic operations to remove the uterus of a patient, while a second clinician may serve in a role of manipulating the position and orientation uterus of the patient to facilitate the operations being performed by the first clinician. Such team-based procedures may require clear communication between the first clinician and the second clinician, with the first clinician instructing the second clinician on desired positioning and orientation of the uterus, and with the second clinician responding in a timely and accurate fashion. In some scenarios, such communications may break down or otherwise yield undesirable results, such as the second clinician not precisely positioning or orienting the uterus when and where the first clinician wishes. It may therefore be desirable to provide a robotic system that is capable of performing at least part of the role of the second clinician, such that the robotic system may at least partially control the position and orientation of the uterus based on the desire of the first clinician. Examples of how a robotic system may provide uterine manipulation are described in greater detail below. The following examples may be readily incorporated into any of the various robotic systems (10, 36, 47, 100, 140A) described herein; or in any other suitable robotic system.

Figure 21:
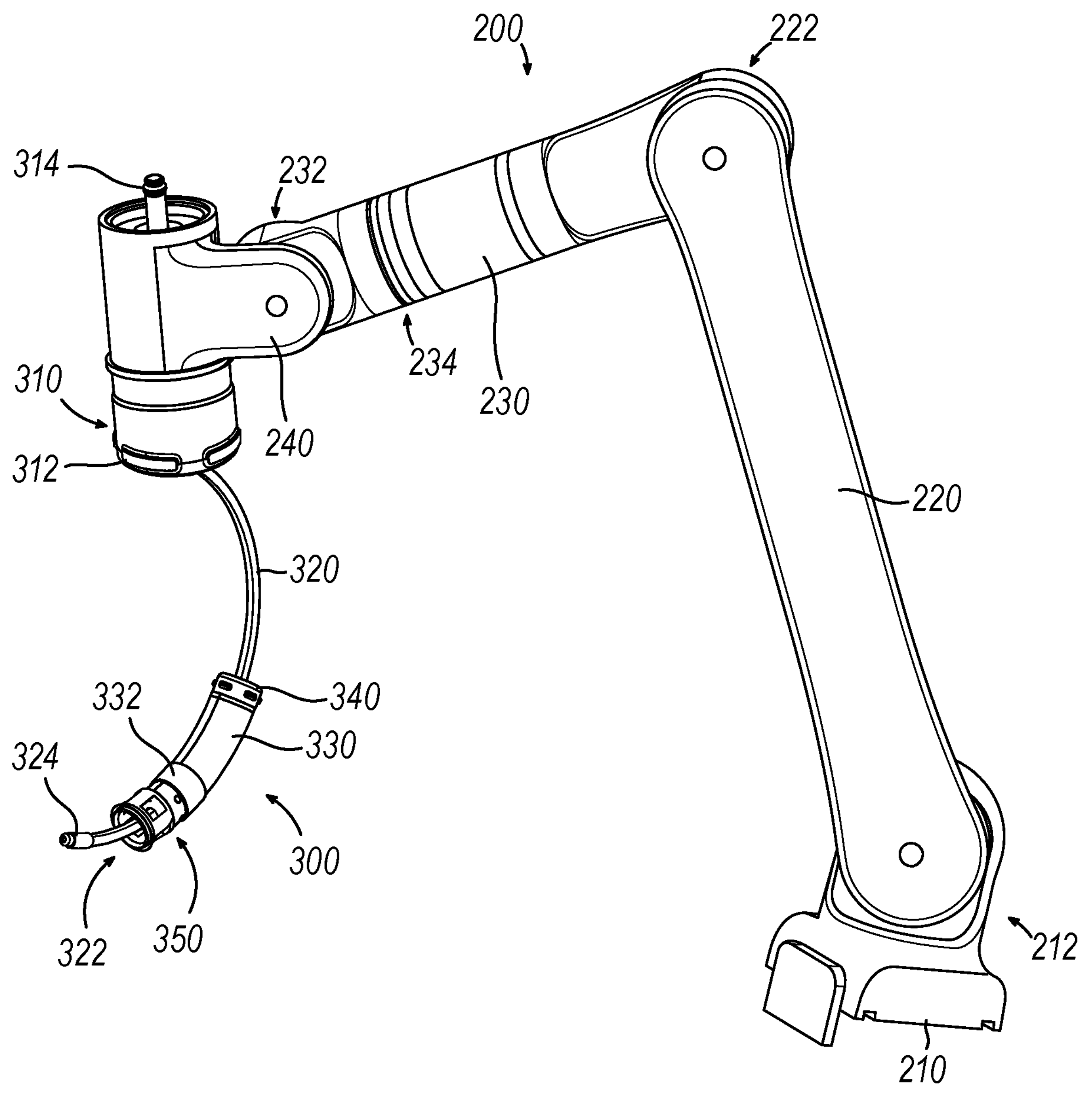
FIG. 21 depicts a perspective view of an example of a robotic arm with a uterine manipulator instrument.

FIG. 21 shows an example of a uterine manipulator (300) secured to a robotic arm (200). Robotic arm (200) of this example includes a mount (210), arm segments (220, 230), a plurality of joints (212, 222, 234, 232), and a head (240). Mount (210) is configured to couple with a component of a robotic system (10, 36, 47, 100, 140A) for support. For instance, mount (210) may be coupled with carriage interface (19), carriage (43), rail (197), or any other suitable structure. In some versions, base (210) is operable to translate along the structure to which base (210) is secured, to thereby assist in positioning robotic arm (200) in relation to a patient and/or to otherwise position robotic arm (200). One end of arm segment (220) is pivotably coupled to base (210) via joint (212), such that arm segment (220) is pivotable relative to base (210) at joint (212). The other end of arm segment (220) is pivotably coupled to an end of arm segment (230) via joint (222), such that arm segment (230) is pivotable relative to arm segment (220) at joint (222). The other end of arm segment (230) is coupled with joint (232) via joint (234). Joint (234) is configured to allow joint (232) and head (240) to rotate relative to arm segment (230) about the longitudinal axis of arm segment (230). In some variations, a similar kind of joint is provided in arm segment (220), such that arm segment (220) may be effectively broken into two segments where one of those segments is rotatable relative to the other about the longitudinal axes of those two segments. Head (240) is pivotably coupled with joint (234) via joint (232), such that head (240) is pivotable relative to joint (234) at joint (232). Motion at any of joints (212, 222, 234, 232) may be driven robotically via motors, solenoids, and/or any other suitable source(s) of motion.

Figure 22:
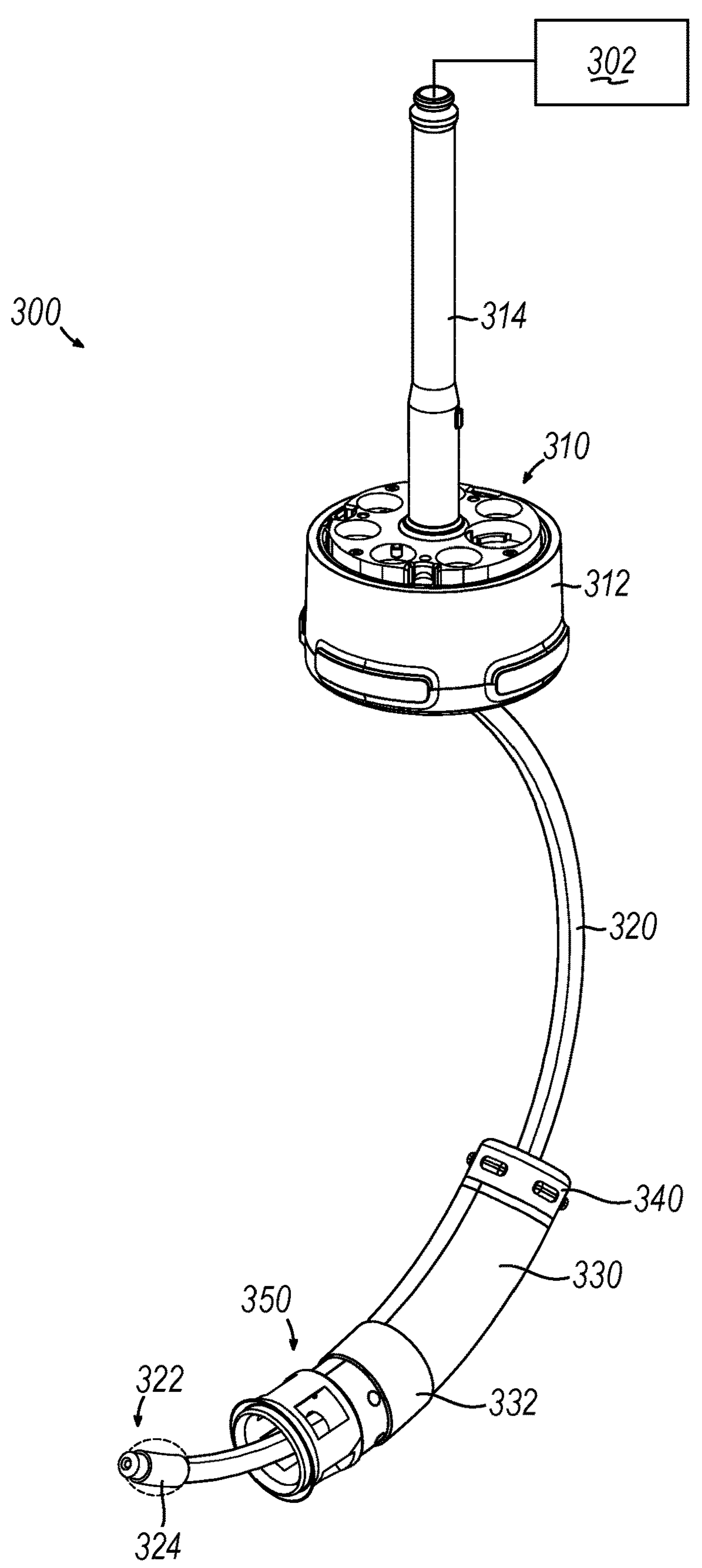
FIG. 22 depicts a perspective view of the uterine manipulator instrument of FIG. 21.

Uterine manipulator (300) is removably coupled with head (240), such that robotic arm (200) may selectively position and orient uterine manipulator in relation to a patient by driving robotic arm (200). As best seen in FIG. 22, uterine manipulator (300) of the present example includes a head interface assembly (310), a shaft (320), a sleeve (330), a sleeve locking ring (340), and a colpotomy cup (350). Head interface assembly (310) includes a base (312) and a shaft (314). Base (312) is configured to removably couple with head (240) to thereby secure uterine manipulator (300) with head (240). By way of example only, base (312) and head (240) may include complementary bayonet fitting features, complementary threading, complementary snap-fit features, and/or any other suitable kinds of structures to provide a removable coupling. Shaft (320) is configured to couple with a pressurized fluid source (302). Pressurized fluid source (302) may contain pressurized air, pressurized saline, or any other suitable kind of pressurized fluid. The pressurized fluid may be used to selectively inflate balloons (324, 332), which will be described in greater detail below.

Shaft (320) of the present example extends distally from base (312) along a curve. In some versions, shaft (320) is rigid. In some other versions, shaft (320) is flexible yet resiliently biased to assume the curved configuration shown. Any suitable biocompatible material(s) may be used to form shaft (320), including but not limited to metallic materials, plastic materials, and combinations thereof. An inflatable balloon (324) is positioned near distal end (322) of shaft (320). Balloon (324) may be formed of an extensible material or a non-extensible material. The interior of shaft (320) includes one or more lumen(s) that are configured to communicate pressurized fluid from pressurized fluid source (302) to balloon (324). While balloon (324) is positioned near distal end (322) of shaft (320) in the present example, other versions may include a different kind of expandable member. By way of example only, an alternative expandable member may include a mechanically expandable component such as an expandable mesh structure, an expanding umbrella-like structure, or any other suitable kind of expandable structure or assembly. In some versions, distal end (322) of shaft (320) may also include an illuminating element (e.g., one or more LEDs, a lens illuminated by one or more optical fibers, etc.). In such versions, one or more wires, optical fibers, and/or other components may extend along the length of shaft (320) to couple with a source of electrical power, a source of light, etc.

Sleeve (330) is slidably coupled to shaft (320), such that sleeve (330) may slide along shaft (320) from a proximal position (FIGS. 25B-25C) to any number of distal positions (FIGS. 21, 22, 25D-25E). Sleeve (330) is generally cylindraceous and rigid; and extends along a curved axis such that the curved lateral profile complements the curved lateral profile of shaft (320). Sleeve (330) may be formed of plastic, metal, and/or any other suitable biocompatible material(s), including combinations of materials. Locking ring (340) is rotatably secured to the proximal end of sleeve (330), while colpotomy cup (350) is fixedly secured to the distal end of sleeve (330). An inflatable balloon (332) is positioned along sleeve (330), between locking ring (340) and colpotomy cup (350). Balloon (332) may be formed of an extensible material or a non-extensible material. The interior of sleeve (330) includes one or more lumen(s) that are configured to communicate pressurized fluid from pressurized fluid source (302) to balloon (332). Such a lumen or lumens may be coupled with pressurized fluid source (302) via a flexible tube (not shown). In some versions, one or more lumens or tubes within shaft (320) provide at least part of the fluid pathway between balloon (332) and pressurized fluid source (302).

Locking ring (340) is operable to selectively secure the position of sleeve (330) along the length of shaft (320). For instance, locking ring (340) may be rotated to a first angular position relative to sleeve (330) to provide an unlocked state where sleeve (330) may be freely translated along shaft (320). Locking ring (340) may then be rotated to a second angular position relative to sleeve (330) to provide a locked state where the position of sleeve (330) along shaft (320) is secured until locking ring (340) is rotated back to the first angular position. By way of example only, locking ring (340) may include one or more frictional braking structures that selectively engage shaft (320) to thereby provide the locked state. Alternatively, locking ring (340) may selectively engage shaft (320) in any other suitable fashion.

Figure 23:
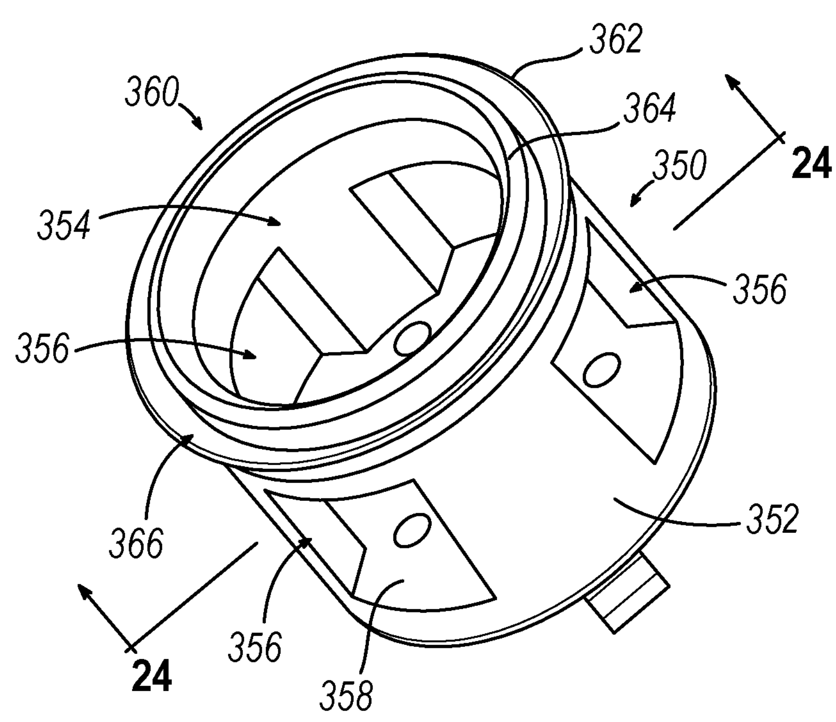
FIG. 23 depicts a perspective view of a colpotomy cup of the uterine manipulator instrument of FIG. 23.
Figure 24:
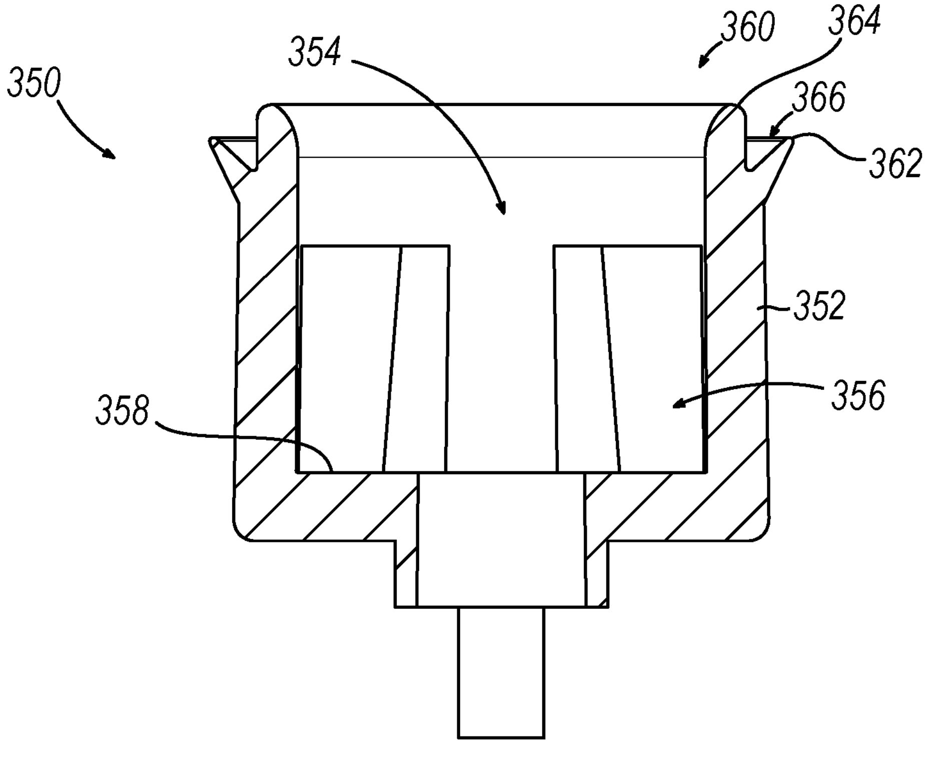
FIG. 24 depicts a cross-sectional side view of the colpotomy cup of FIG. 23.

FIGS. 23-24 show colpotomy cup (350) in greater detail. As shown, colpotomy cup (350) of the present example includes a body (352) defining an interior space (354). Body (352) further includes a floor (358) at the bottom of interior space (354) and an open distal end (360). A plurality of lateral openings (356) are in communication with interior space (354). Distal end (360) includes a distally presented annular edge (364) and an obliquely presented annular edge (362), with a space (366) being defined between edges (362, 364). Space (366) has a V-shaped cross-sectional profile, as best seen in FIG. 24. Colpotomy cup (350) may be formed of plastic, metal, and/or any other suitable biocompatible material(s), including combinations of materials.

Figure 25A:
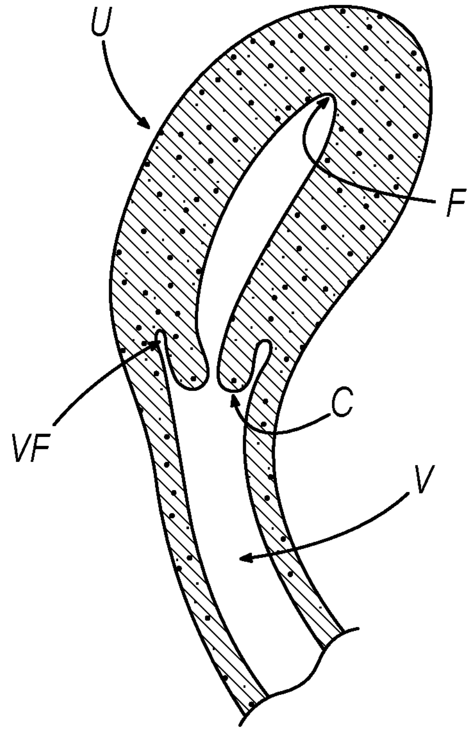
FIG. 25A depicts a mid-sagittal cross-sectional view of a vagina and uterus.
Figure 25B:
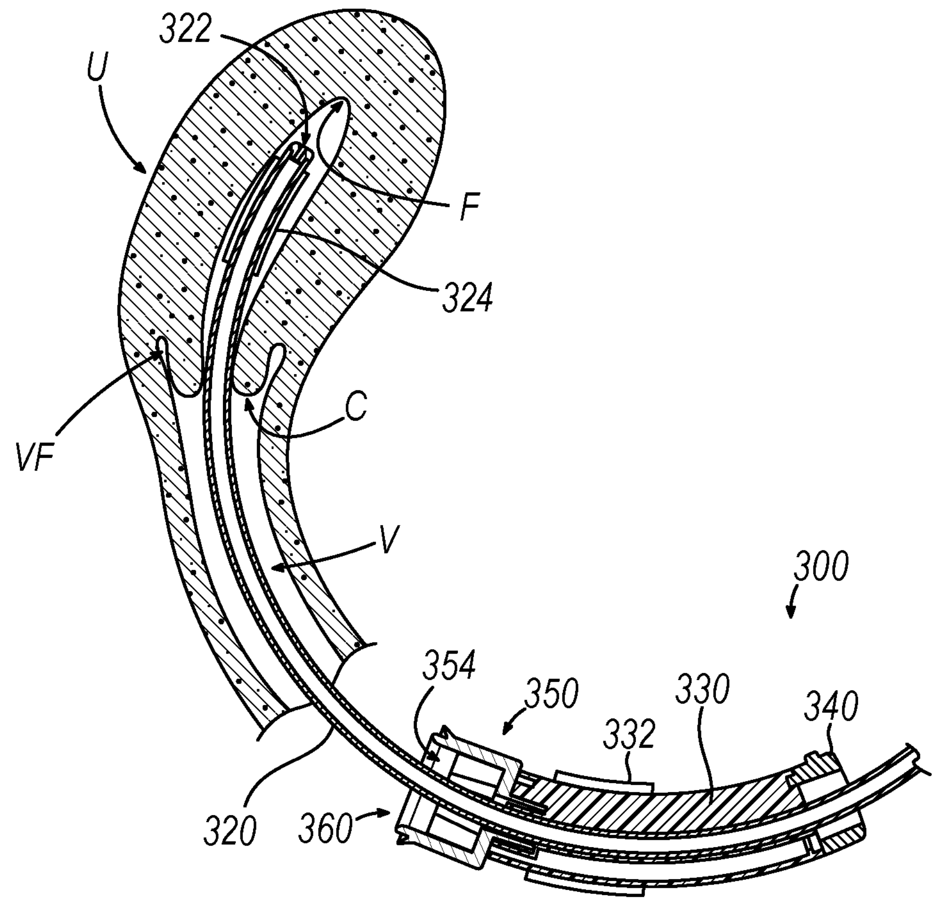
FIG. 25B depicts a mid-sagittal cross-sectional view of the vagina and uterus of FIG. 25A, with the shaft of the uterine manipulator instrument of FIG. 21 inserted through the vagina into the uterus, with a balloon of the uterine manipulator instrument of FIG. 21 in a deflated state, and with a sleeve of the uterine manipulator instrument in a proximal position.
Figure 25C:
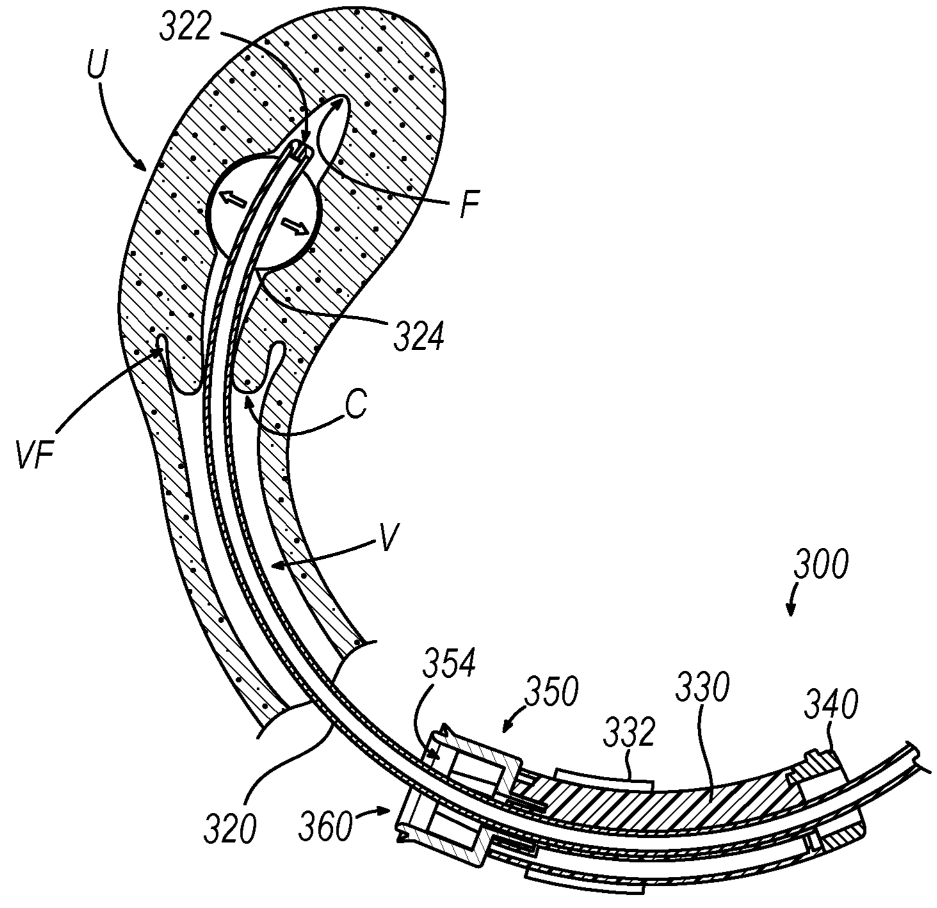
FIG. 25C depicts a mid-sagittal cross-sectional view of the vagina and uterus of FIG. 25A, with the shaft of the uterine manipulator instrument of FIG. 21 inserted through the vagina into the uterus, with the balloon of the uterine manipulator instrument of FIG. 21 in an inflated state, and with the sleeve of the uterine manipulator instrument in the proximal position.

FIGS. 25A-25E show an example of a procedure in which uterine manipulator (300) is used. As shown in FIG. 25A, the anatomical context in which uterine manipulator (300) is used includes a vagina (V) and uterus (U) of a patient. As shown in FIG. 25B, shaft (320) is inserted through the vagina (V) and into the uterus (U) via the cervix (C), while sleeve (330) is in a proximal position along shaft (320). Balloon (324) is in a deflated state during this stage of insertion. In some versions, uterine manipulator (300) is fully decoupled from robotic arm (200) during the process leading up to the stage shown in FIG. 25B, such that uterine manipulator (300) is advanced to this state manually by a human operator grasping a proximal portion of uterine manipulator (300) (e.g., grasping a proximal portion of shaft (320), grasping base (312), and/or grasping some other part of uterine manipulator (300)). In such scenarios, uterine manipulator (300) may be coupled with robotic arm (200) after reaching the stage shown in FIG. 25B.

In some other versions, uterine manipulator (300) is already coupled with robotic arm (200) before reaching the stage shown in FIG. 25B; and robotic arm (200) is used to guide and drive uterine manipulator (300) to the position shown in FIG. 25B. As yet another variation, some versions may allow a human operator to guide and drive uterine manipulator (300) to the position shown in FIG. 25B while uterine manipulator (300) is coupled with robotic arm (200), such that robotic arm (200) does not restrict manual movement of uterine manipulator (300) leading up to the stage shown in FIG. 25B.

Regardless of the stage at which uterine manipulator (300) is coupled with robotic arm (200), robotic arm (200) may be positioned in various suitable ways relative to the patient while uterine manipulator (300) is inserted in the patient. In some scenarios, robotic arm (200) crosses over the top of one of the patient's legs from the side, to assist in positioning uterine manipulator (300). In some other scenarios (e.g., when the patient's legs are supported by stirrups (58)), robotic arm (200) crosses under the bottom of one of the patient's legs from the side, to assist in positioning uterine manipulator (300). In still other scenarios, robotic arm (200) is positioned between the patient's legs from underneath, such that robotic arm (200) does not cross over or under either of the patient's legs. Alternatively, robotic arm (200) may have any other suitable spatial and positional relationship with respect to the patient.

In the present example, uterine manipulator (300) is advanced distally until distal end (322) of shaft (320) reaches the fundus (F) of the uterus (U). The operator may determine that distal end (322) has reached the fundus (F) via tactile feedback (e.g., such that the operator can feel sudden resistance to further advancement of shaft (320)). In addition, or in the alternative, in versions where distal end (322) includes an illuminating element, the illuminating element may provide transillumination through the wall of the uterus (U). Such transillumination may be observed via a laparoscope or other visualization device that is positioned external to the uterus (U). Such transillumination may indicate the extent to which shaft (320) has been inserted into the uterus (U). In some cases where distal end (322) contacts the fundus (F), distal end (322) may remain in contact with fundus (F) throughout the rest of the procedure shown in FIGS. 25B-25E. In some other versions, distal end (322) may be slightly backed out proximally, such that distal end (322) does not contact fundus (F) throughout the rest of the procedure shown in FIGS. 25B-25E.

After reaching the state shown in FIG. 25B, balloon (324) may be inflated as described above; and as shown in FIG. 25C. In some cases, balloon (324) is inflated to a point where balloon (324) bears outwardly against the sidewall of the uterus (U). In any case, the inflated balloon (324) may stabilize the distal portion of shaft (320) relative to the uterus (U). Specifically, the inflated balloon (324) may prevent shaft (320) from exiting proximally from the uterus (U) via the cervix (C). Balloon (324) may thus serve as a distally-positioned anchor structure for uterine manipulator (300). The inflated balloon (324) may also provide sufficient engagement between shaft (320) and the uterus (U) to allow use of shaft (320) to reposition and reorient the uterus (U) as described herein.

Figure 25D:
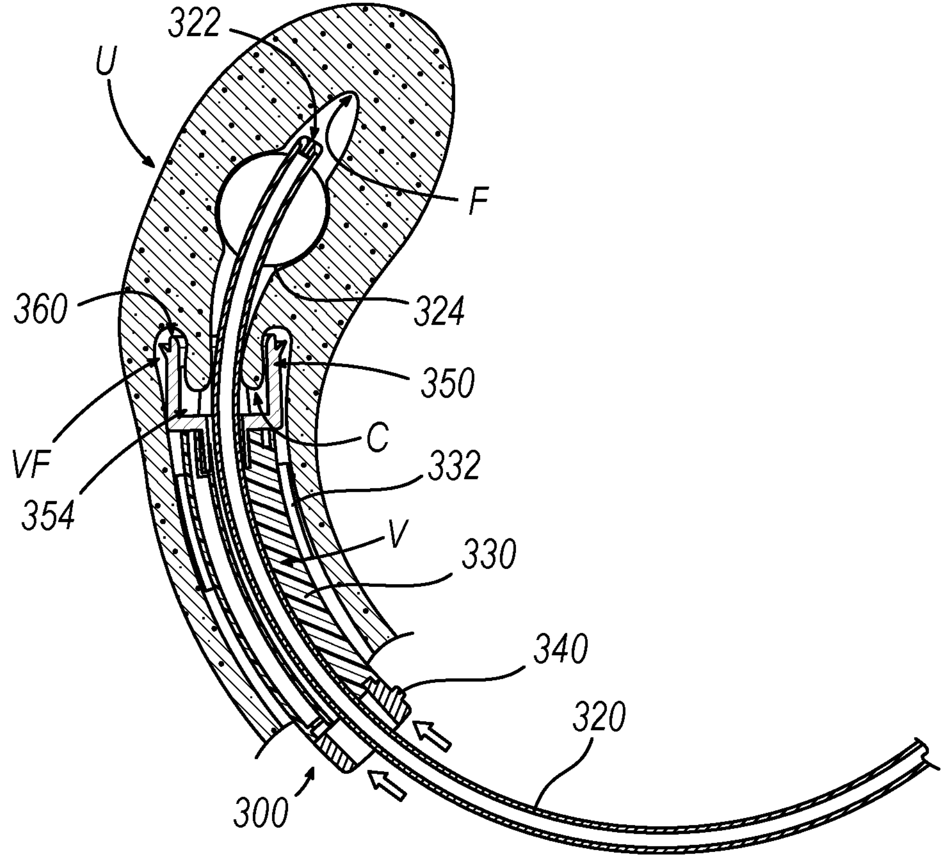
FIG. 25D depicts a mid-sagittal cross-sectional view of the vagina and uterus of FIG. 25A, with the shaft of the uterine manipulator instrument of FIG. 21 inserted through the vagina into the uterus, with the balloon of the uterine manipulator instrument of FIG. 21 in the inflated state, with the sleeve of the uterine manipulator instrument in a distal position such that the colpotomy cup of the sleeve is engaged with the cervix, and with a balloon of the sleeve in a deflated state.

With balloon (324) in the inflated state the operator may advance sleeve (330) distally along shaft (320) to the position shown in FIG. 25D. In the present example, this is performed by a human operator manually advancing sleeve (330) distally along shaft (320). In some other versions, this may be performed by a robotic operator robotically advancing sleeve (330) distally along shaft (320). As shown, sleeve (330) is advanced distally to a point where distal end (360) is firmly seated in the vaginal fornix (VF). The cervix (C) is received in interior space (354) of body (352). At this stage, the longitudinal position of sleeve (330) along shaft (320) is locked in place via locking ring (340). Specifically, the operator grasps locking ring (340) and rotates locking ring (340) about shaft (320) to firmly lock the position of sleeve (330) along shaft (320). In the present example, this is performed by a human operator, though it may be performed by a robotic operator in other versions. With the position of sleeve (330) locked in place against shaft (320), the position of uterine manipulator (300) is substantially fixed relative to the vagina (V), the cervix (C), and the uterus (U). While balloon (324) serves as a distally-positioned anchor structure for uterine manipulator (300), colpotomy cup (350) serves as a proximally-positioned anchor structure for uterine manipulator (300).

Figure 25E:
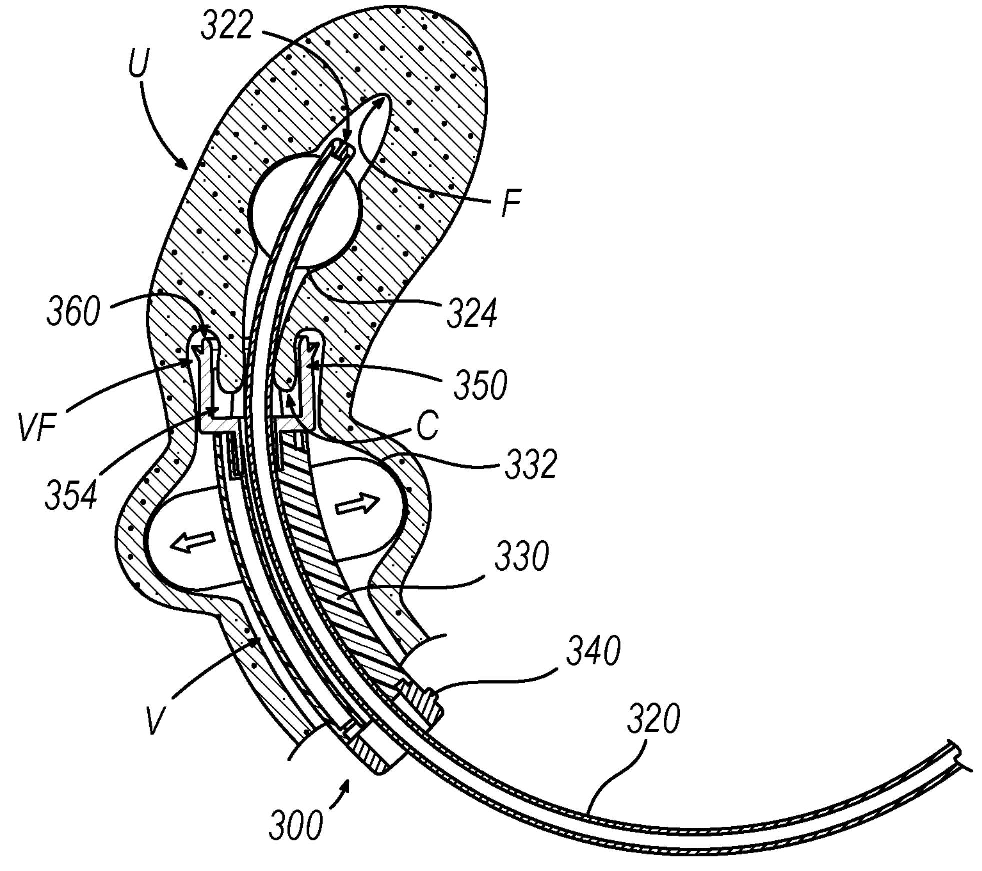
FIG. 25E depicts a mid-sagittal cross-sectional view of the vagina and uterus of FIG. 25A, with the shaft of the uterine manipulator instrument of FIG. 21 inserted through the vagina into the uterus, with the balloon of the uterine manipulator instrument of FIG. 21 in the inflated state, with the sleeve of the uterine manipulator instrument in the distal position such that the colpotomy cup of the sleeve is engaged with the cervix, and with the balloon of the sleeve in an inflated state

With the position of uterine manipulator (300) being fixed by the combination of balloon (324) and colpotomy cup (350), balloon (332) is inflated as shown in FIG. 25E. Balloon (332) bears outwardly against the sidewall of the vagina (V), thereby creating a fluid-tight seal against the sidewall of the vagina (V).

With uterine manipulator (300) being positioned and configured as shown in FIG. 25E, robotic arm (200) may be utilized to drive uterine manipulator (300) to various positions, to thereby re-orient and reposition the uterus (U) as desired by the clinician who is performing the rest of the medical procedure (e.g., hysterectomy). In some scenarios, the clinician who robotically controls robotic arm (200) to drive uterine manipulator (300) to position and orient the uterus (U) also uses the same robotic system to control instruments that are used to perform a surgical procedure associated with the uterus (U) (e.g., a hysterectomy). As noted above, by allowing a surgeon to directly control the manipulation of the uterus (U) via robotic arm (200) and uterine manipulator (300), the process avoids potential confusion and inconsistency that might otherwise result in procedures where a human assistant is controlling a uterine manipulator based on commands from another human clinician. Moreover, once the uterus (U) has been manipulated to achieve the desired position and orientation, robotic arm (200) and uterine manipulator (300) may cooperate to maintain this position and orientation of the uterus (U) indefinitely. This may avoid scenarios where a human operator of a uterine manipulator might inadvertently reposition or reorient the uterus (U) the middle of a medical procedure.

As noted above, one medical procedure that may be performed using robotic arm (200) and uterine manipulator (300) is a hysterectomy. In some versions of such a procedure, one or more cutting instruments are introduced laparoscopically via the patient's abdomen to approach the cervicovaginal junction from outside the uterus (U) and vagina (V). Such instrumentation may be controlled manually or robotically. In versions where the instrumentation is controlled robotically, the same robotic system may control the instrumentation and robotic arm (200). A cutting instrument may cut the uterus (U) away at the cervicovaginal junction, generally tracing around the circular perimeter defined by distal end (360) of colpotomy cup (350).

In some versions, the tissue at the cervicovaginal junction may be distended in response to pressure imposed by distal end (360) of colpotomy cup (350), thereby promoting visualization of the position of distal end (360) of colpotomy cup (350) from a laparoscope that is positioned external to the uterus (U) and vagina (V). Distal end (360) may also urge the ureters of the patient outwardly, thereby reducing the risk of the cutting instrument inadvertently cutting one of the ureters. Also in some versions, the cutting instrument may be received in space (366) defined between edges (362, 364) at distal end (360) of colpotomy cup (350) as the cutting instrument travels in a generally circular motion along the cervicovaginal junction. This cutting at the cervicovaginal junction will ultimately result in separation of the uterus (U) from the vagina (V); and the end of the vagina (V) may be appropriately closed at this point. During this process, the patient's abdomen may be insufflated with pressurized gas, and the pressurized insufflation gas may eventually reach the distal region of the vagina (V). In such scenarios, balloon (332) will provide sealed occlusion that is sufficient to prevent the pressurized insufflation gas from escaping out of the patient via the vagina (V).

While robotic arm (200) and uterine manipulator (300) are described in the foregoing example as being used in a hysterectomy, robotic arm (200) and uterine manipulator (300) may be used in any other suitable fashion and may be used in any other suitable procedures.

III. Example of System Architecture of Robotically Controlled Uterine Manipulator As described above, uterine manipulator (300) may be operated in some uses under full or partial control of robotic arm (200) or other similar structures. Although this may be desirable to provide more precise control of uterine manipulator (300), improve operational efficiencies, and/or improve ease of use, the use of robotic arm (200) may introduce certain challenges not encountered when uterine manipulator (300) is controlled manually. For instance, there may be challenges in positioning robotic arm (200) relative to patient anatomy associated with uterine manipulator (300). In addition, or in the alternative, there may be challenges with observing or obtaining feedback related to manipulation while also controlling robotic arm (200). Similarly, there may be challenges related to procedures that combine manual manipulation with robotic manipulation. Thus, certain features may be desirable to address challenges of integration of structures similar to uterine manipulator (300) with structures similar to robotic arm (200). Although various specific examples of structures and/or features are described below for integrating uterine manipulators into robotic platforms, it should be understood that in other versions, said structures and/or features may be combined as will be apparent to those skilled in the art in view of the teachings herein

A. Example of Robotic Platform for Uterine Manipulator

Implementations of uterine manipulator (300) or similar medical instruments or tools with robotic arm (200) or other robotic manipulators as described above may provide benefits in terms of increased instrument control, increased procedure efficiency, increased procedure room communication, and/or other benefits. However, such configurations described above may present some implementation challenges associated with patient anatomy. For instance, manipulation of uterine manipulator (300) or similar medical instruments or tools relative to patient anatomy such as the vagina (V) and associated anatomy may lead to challenges related to the position of robotic arm (200) or other robotic manipulators. As such, there may be a need for increased flexibility in robotic platforms with positioning and adjustment. Although various specific examples of structures and/or features are described below for increasing flexibility in robotic platforms, it should be understood that in other versions, said structures and/or features may be combined as will be apparent to those skilled in the art in view of the teachings herein.

Figure 26:
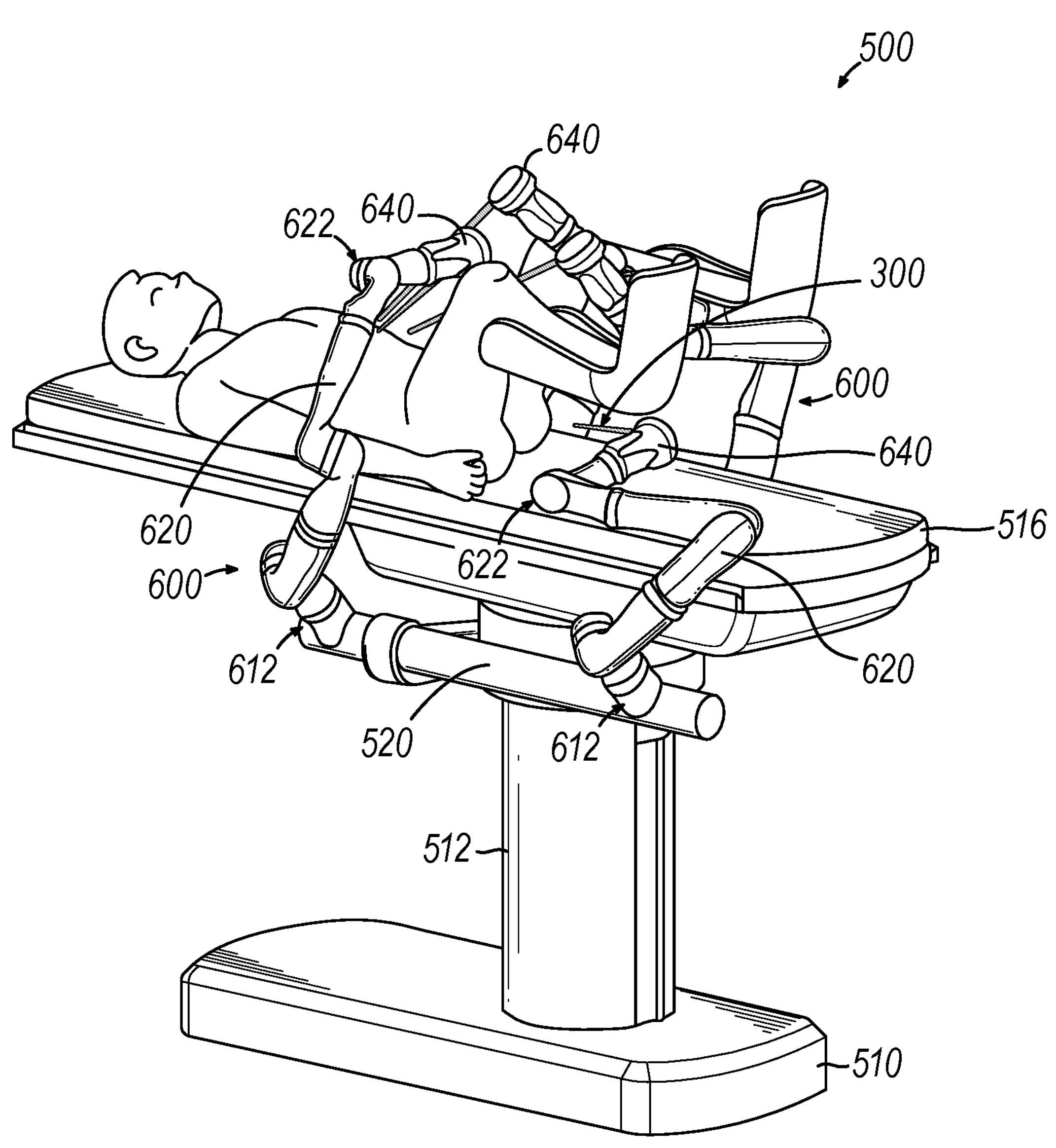
FIG. 26 depicts a perspective view of an alternative version of a table-based robotic system, with a robotic arm in an under-leg orientation.

FIG. 26 depicts an exemplary system architecture for use with uterine manipulator (300) described above. In the present example, uterine manipulator (300) may be used with a robotic system (500) to control movement of uterine manipulator (300) and/or other associated one or more robotic medical instruments or tools during a procedure. Robotic system (500) of the present example is substantially similar to robotic systems (10, 36, 47, 100, 140A) described above. For instance, robotic system (500) of the present example includes a base (510) supporting a column (512) and a patient table (516). Robotic system (500) further includes a grounding structure (520) attached or otherwise secured to column (512) and supported by base (510). In some versions, grounding structure (520) may be configured to move longitudinally along the length of column (512). Regardless, grounding structure (520) of the present example is configured as a rail or bar, which may be used to support one or more robotic arms (600).

Grounding structure (520) of the present example is movable into a plurality of positions relative to patient table (516). In one such position, grounding structure (520) extends along the side of patient table (516) to support flexible adjustability of one or more of robotic arms (600). In other words, grounding structure (520) may be proximate the side of patient table (516) (e.g., extending along the arms of a patient). Specifically, patient table (516) may define a longitudinal axis, while grounding structure (520) may likewise define a longitudinal axis. The longitudinal axis of patient table (516) may be approximately parallel with the longitudinal axis of grounding structure (520). Grounding structure (520) of the above-referenced configuration may be desirable to promote greater control over the location of robotic arms (600) relative to a patient for closer or more flexible positioning of robotic arms (600) relative to the patient. Additionally, grounding structure (520) of the above-referenced configuration may be desirable to provide an increased number of angles of attack relative to patient anatomy by one or more of robotic arms (600).

Robotic system (500) of the present example includes two substantially similar grounding structures (520) positioned on opposite sides of patient table (516). In other versions, only a single grounding structure (520) may be used. In yet other versions, multiple grounding structures (520) may be used such as three or more. Regardless of the particular number of grounding structures (520) used, suitable grounding structures (520) may all couple to column (512), and thereby to base (510), so that all grounding structures (520) are anchored or connected to a common point. Such a configuration may be desirable in some examples so that robotic arms (600) may have a common mechanical ground.

As will be appreciated, such a common mechanical ground may be desirable to provide a global coordinate system to simplify robotic control and coordination of robotic arms (600). In addition to, or alternative to, the foregoing, grounding structures may be configured and operable like carriage interface (19) described above, carriage (43) described above, rail (197) described above, or any other suitable structure.

As with robotic systems (10, 36, 47, 100, 140A) described above, robotic system (500) of the present example includes a plurality of robotic arms (600). Robotic arms (600) used in the present example may be configured similarly to any one or more of robotic arms (12, 39, 50, 76, 83, 141A, 142B, 200) described herein for the manipulation of one or more robotic medical instruments or tools during a procedure. For instance, at least one robotic arm (600) may be configured similarly to robotic arm (200) describe above for use with uterine manipulator (300). Meanwhile, other robotic arms (600) may be configured to support and/or manipulate other robotic medical instruments or tools during a procedure. Thus, any one or more of robotic arms (600) may include a mount (612), arm segments (620), a plurality of joints (622), and a head (640) as similarly described above with respect to mount (210), arm segments (220, 230), joints (212, 222, 232, 234), and head (240) of robotic arm (200).

Any one or more of robotic arms (600) may be configured to slide or otherwise move longitudinally along the longitudinal axis defined by grounding structure (520). Such sliding or longitudinal movement may be controlled robotically by robotic system (500), may be manual, or may a combination of robotic control and manual control may be used. In an implementation with uterine manipulator (300), this configuration may be desirable to promote access to specific patient anatomy such as vagina (V) and other associated anatomy. For instance, as shown in FIG. 26, this configuration may permit positioning of at least one robotic arm (600) towards an end of patient table (516) associated with a patient's hip or legs. In this position, the robotic arm (600) supporting uterine manipulator (300) may be positioned beneath a patient's legs while the legs are held upwardly in leg holders (e.g., similar to stirrups (58) referred to above) or other patient positioning structures. Positioning the robotic arm (600) supporting uterine manipulator (300) beneath the patient's legs may facilitate accessing the vagina (V) with uterine manipulator (300). Such an arrangement may also facilitate movement of the robotic arm (600) supporting uterine manipulator (300) during the process of manipulating the uterus (U).

Figure 27:
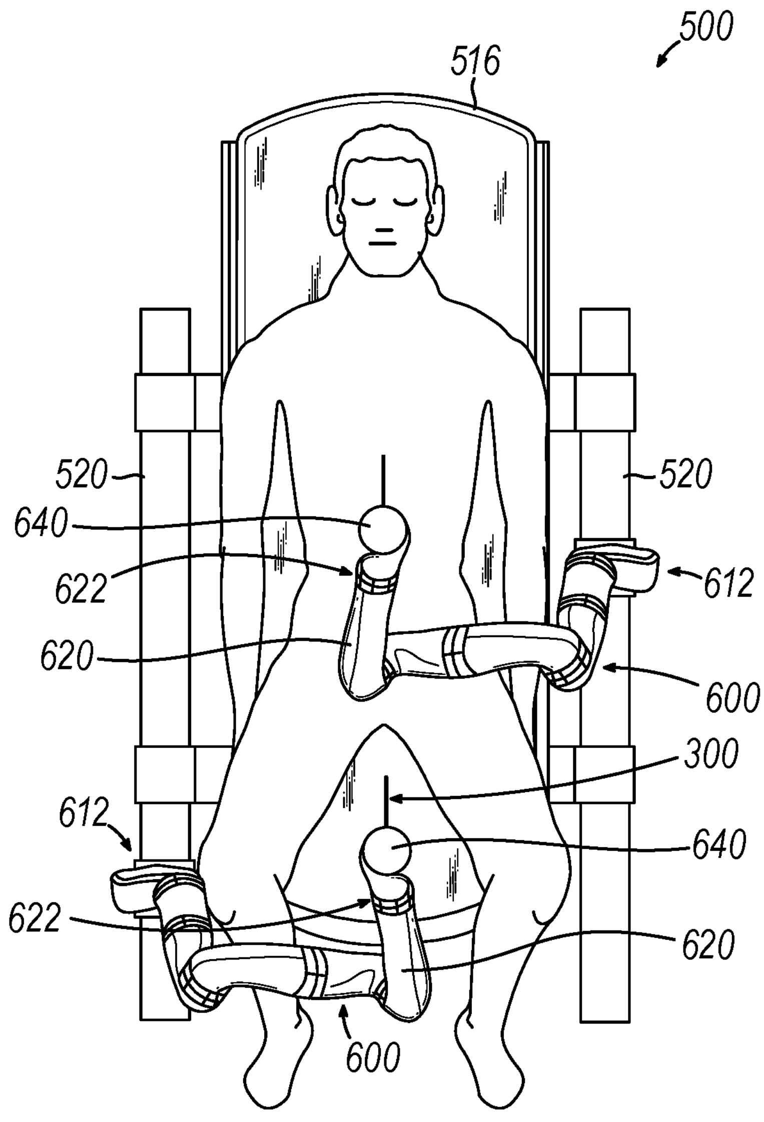
FIG. 27 depicts another perspective view of the table-based robotic system of FIG. 26, with the robotic arm in an over-leg orientation.

FIG. 27 shows another implementation of uterine manipulator (300) with at least one of robotic arms (600). As can be seen, in some implementations, the robotic arm (600) associated with uterine manipulator (300) may still be positioned on grounding structure (520) towards the end of patient table (516) associated with a patient's hips or legs. However, instead of the robotic arm (600) being positioned beneath a patient's legs, the robotic arm (600) may be positioned above one of the patient's legs. This implementation may be desirable in contexts where the patient's legs are permitted to hang from patient table (516) or are supported by a portion of patient table (516) in a flat or declined position. In such scenarios, positioning the robotic arm (600) supporting uterine manipulator (300) above the patient's leg may facilitate accessing the vagina (V) with uterine manipulator (300). Such an arrangement may also facilitate movement of the robotic arm (600) supporting uterine manipulator (300) during the process of manipulating the uterus (U).

In view of the foregoing, robotic arm (600) may be used to position uterine manipulator (300) either over or under the patient's leg, depending on whether the patient's leg is supported in an upper position as shown in FIG. 26 or in a lower position as shown in FIG. 27. In either arrangement, robotic arm (600) may have sufficient freedom of movement to readily permit positioning and usage of uterine manipulator (300) with respect to the patient. In other words, robotic arm (600) may provide versatility in use based on the position and configuration of the patient.

B. Exemplary Bedside Controls for Robotic Arm

As described above, in some versions a console or control unit may be used to provide an operator interface with robotic systems (10, 36, 47, 100, 140A, 600) for control of said robotic systems (10, 36, 47, 100, 140A, 600). In some versions, such consoles may be positioned spatially away from the patient and/or robotic systems (10, 36, 47, 100, 140A, 600). Such positioning may be either within the procedure room itself or at an entirely remote location. Although this configuration may be desirable to promote sterility, procedure efficiency, clinician convenience, etc., such a configuration may come at the expense of direct observation of the patient contemporaneously with operation of robotic systems (10, 36, 47, 100, 140A, 600). Moreover, such a configuration may introduce challenges with implementing procedures utilizing combined or hybrid manual and robotic modes of control. Thus, it may be desirable to incorporate certain features into robotic systems (10, 36, 47, 100, 140A, 600) described above to provide alternative operator interface features.

Figure 28:
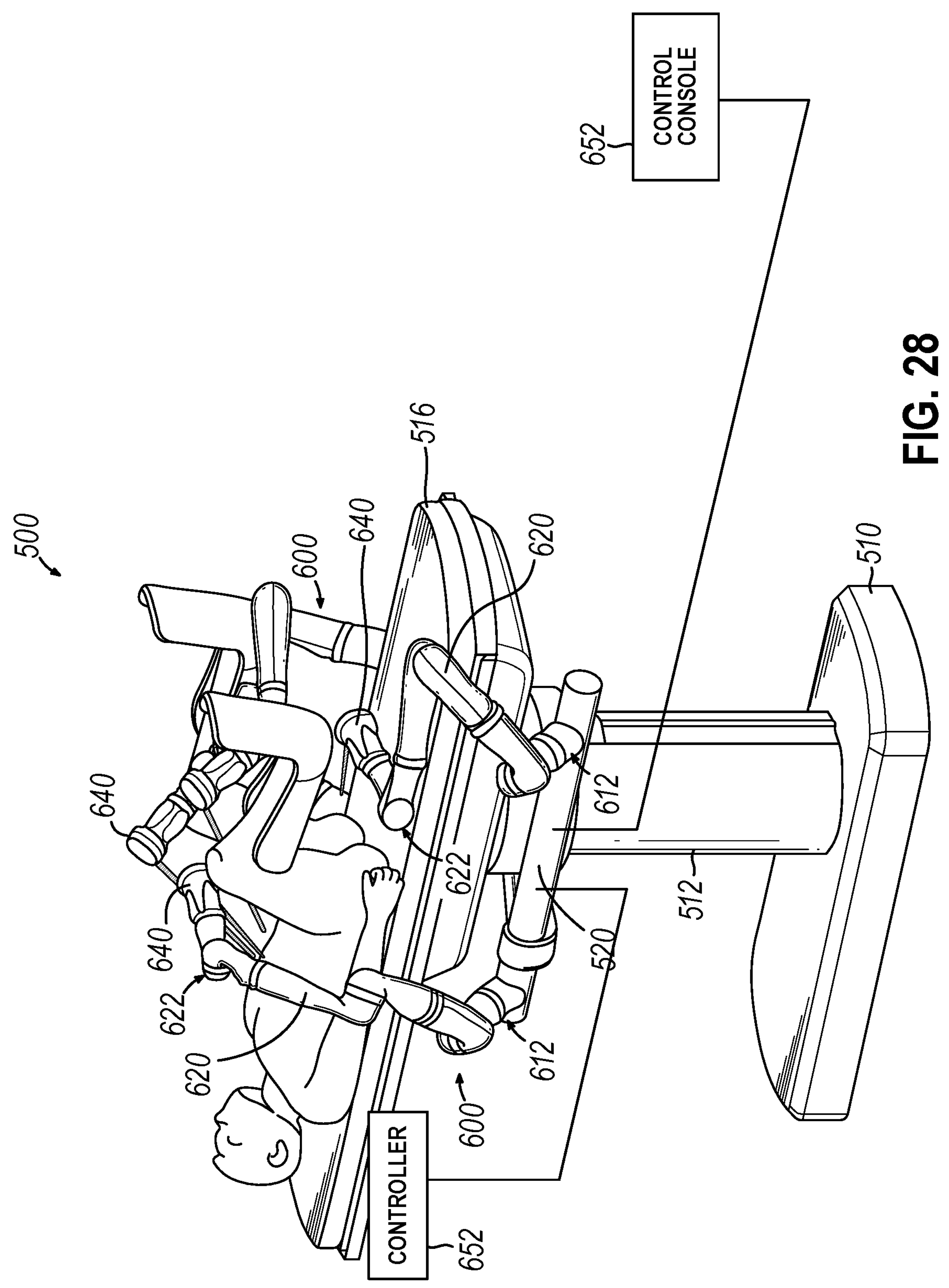
FIG. 28 depicts a perspective view of the table-based robotic system of FIG. 26 used with an exemplary bedside operator interface feature.

FIG. 28 shows a schematic representation of one example configuration of robotic system (500). Although the configuration shown in FIG. 28 and described herein is in connection with robotic system (500), it should be understood that the following teachings may be readily applied to any other suitable robotic system such as any one or more of robotic systems (10, 36, 47, 100, 140A) described above. As can be seen, robotic system (500) of the present example may be used in connection with a console (650) and a bedside operator interface feature (652). Both console (650) and bedside operator interface feature (652) are in communication with robotic system (500) to control one or more operations of one or more of robotic arms (600). Although not shown, it should be understood that one or both of console (650) and/or beside operator interface feature (652) may also be in communication with one or more associated structures similar to tower (30) described above. Additionally, such communication may be facilitated via wired connections, wireless connections, or various combinations thereof.

Console (650) in the present example is substantially similar to console (30) described above. For instance, as similarly described above, console (650) may include a user interface and a display screen for use by an operator. Console (650) may likewise be configured to provide both robotic controls as well as pre-operative and real-time information such as navigational and localization information.

Bedside operator interface feature (652) is similar to console (650) in that bedside operator interface feature (652) may include robotic controls in addition to providing procedure information. However, unlike console (650), bedside operator interface feature (652) is configured for portability, simplified use, and/or use targeted towards specific functions of robotic system (500). As such, bedside operator interface feature (652) may include a simplified interface with reduced control inputs and/or display components relative to console (650). Furthermore, bedside operator interface feature (652) may include a reduced size or footprint relative to console (650) for handheld use. Similarly, bedside operator interface feature (652) of some versions may be integrated into other components such as one or more robotic arms (600).

In some versions of bedside operator interface feature (652), bedside operator interface feature (652) may be configured as a handheld controller with a wired or wireless connection configured to drive one or more movements of a specific robotic arm (600). To facilitate such function, such a bedside operator interface feature (652) may include one or more movement control interface features such as joysticks, multi-axis control pads, capacitive touch sensors, etc. Such movement control interface features may be configured to drive one or more specific movements of a given robotic arm (600). Additionally, or in the alternative, such movement control interface features may be configured to drive a given robotic arm (600) through one or more predetermined movements along a specific axis or within a specific plane.

Figure 29:
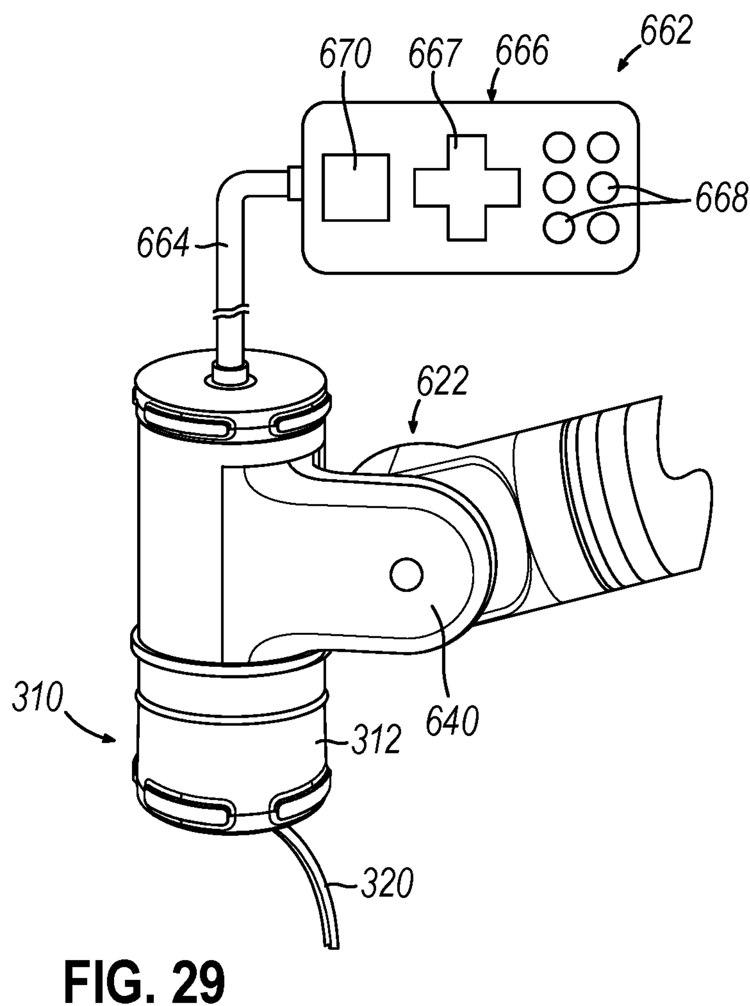
FIG. 29 depicts a perspective view of an alternative version of a bedside operator interface feature.

FIG. 29 shows another example of a suitable bedside operator interface feature (662) that may be used with robotic system (500). Beside operator interface feature (662) may be used either in combination with beside operator interface feature (652) described above or with bedside operator interface feature (652) omitted. Bedside operator interface feature (662) may also be viewed as an illustrative example of a form that may be taken by bedside operator interface feature (652). Bedside operator interface feature (662) of the present example includes a connection post (664) and a control portion (666) oriented on one side of connection post (664). Connection post (664) is generally configured to couple to a portion of robotic arm (600). For instance, in the present example, connection post (664) is coupled to a portion of head (640). However, it should be understood that in other examples, connection post (664) may be coupled to any other suitable component of robotic arm (600). In other versions, connection post (664) may couple to other components such as uterine manipulator (300). Additionally, connection post (664) may be fixedly secured to robotic arm (600) or removably secured to robotic arm (600). In versions where connection post (664) is removably secured to robotic arm (600), a retractable wire or other communication feature may be incorporated into control post (664) to promote free movement of beside operator interface feature (662) relative to robotic arm (600).

Control portion (666) includes a multi-axis control pad (667), a plurality of control buttons (668), and a haptic feedback device (670). Multi-axis control pad (667) is generally configured to control movement of robotic arm (600). Specifically, multi-axis control pad (667) may be configured to control robotic arm (600) within a predetermined plane or along predetermined axes. As will be described in greater detail below, in some examples, the association of multi-axis control pad (667) with certain movements of robotic arm (600) may be fixed or may be selectable. In some variations, multi-axis control pad (667) is replaced with a joystick and/or other kind(s) of user input feature(s).

Control buttons (668) are arranged in a rectangular array in the present example. Specifically, the present example includes six control buttons (668) arranged in a 2×3 array, although other suitable arrangements and numbers of control buttons (668) may be used. Control buttons (668) may be associated with various operations of robotic arm (600). For instance, in some versions, one or more control buttons (668) may be used to lock and/or unlock movement of robotic arm (668). In addition, or in the alternative, in some versions one or more control buttons (668) may be associated with one or more predetermined positions of robotic arm (600) such that robotic arm (600) may be moved to a predetermined position by pressing a single button. Also in some versions, one or more control buttons (668) may be programmable so that an operator may save specific positions of robotic arm (660) during a procedure to return to at a later point. In still other versions, one or more control buttons (668) may be associated with multi-axis control pad (667) to shift the association of multi-axis control pad (667) between different movements of robotic arm (600) such as between different axes or planes. In addition, or in the alternative, one or more control buttons (668) may be operable to control one or more features of uterine manipulator (300). By way of example only, one control button (668) may be operable to trigger inflation of balloon (324) while another control button (668) is operable to trigger inflation of balloon (332). Alternatively, control buttons (668) may provide any other suitable kind of operability as will be apparent to those skilled in the art in view of the teachings herein.

Haptic feedback device (670) may be positioned within control portion (660) or connection post (664) to provide haptic feedback to an operator during a procedure. Such haptic feedback may be implemented in a variety of ways to communicate information to an operator. For instance, in some versions haptic feedback device (670) may be configured to confirm to an operator that multi-axis control pad (667), one or more control buttons (668), or both have been pressed or actuated. In other versions, haptic feedback device (670) may be used to indicate movement of robotic arm (600). In still other versions, haptic feedback device (670) may be used to indicate movement of robotic arm (600) into certain predetermined zones. Such a use may be configured to provide a warning to an operator as to certain procedure conditions such as a perforation danger, as will be described in greater detail below. Haptic feedback device (670) may provide haptic feedback in the form of vibrations, jolts, and/or other kinds of haptic feedback (670). Different forms of haptic feedback may indicate different conditions, such as a single vibration pulse indicating a first condition (e.g., initiation of movement of robotic arm (600)); a pattern of two vibration pulses indicating a second condition (e.g., indicating that robotic arm (600) has reached a targeted position); a pattern of strong, rapid vibrations indicating a third condition (e.g., robotic arm (600) and/or uterine manipulator (300) applying force to tissue in excess of a threshold value). Alternatively, haptic feedback device (670) may provide haptic feedback in any other suitable fashion as will be apparent to those skilled in the art in view of the teachings herein.

Figure 30:
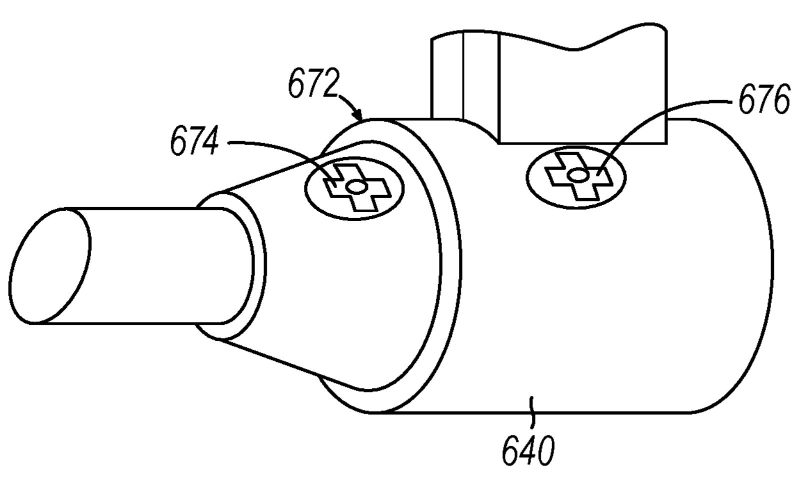
FIG. 30 depicts a perspective view of another alternative version of a bedside operator interface feature.

FIG. 30 shows another example of a suitable bedside operator interface feature (672) that may be used with robotic system (500). Beside operator interface feature (672) may be used either in combination with beside operator interface features (652, 662) described above or with any one or more of bedside operator interface features (652, 662) omitted. Bedside operator interface feature (672) may also be viewed as an illustrative example of a form that may be taken by bedside operator interface feature (652). Beside operator interface feature (672) of the present example is generally integrated into one or more components of robotic arm (600). Specifically, operator interface feature (672) of the present example is shown as being integrated into one or more portions of head (640). However, it should be understood that in other versions, operator interface feature (672) may be readily incorporated into other components of robotic arm (600) such as arm segments (620) or mount (612), etc.

Operator interface feature (672) of the present example includes a first multi-axis control pad (674) and a second multi-axis control pad (676). As with multi-axis control pad (667) described above, multi-axis control pads (674, 676) of the present example may be configured to be associated with specific movements of robotic arm (600). For instance, in some versions, first multi-axis control pad (674) may be associated with movement of robotic arm (600) through one plane or axis of movement. Meanwhile, second multi-axis control pad (676) may be associated with movement of robotic arm (600) through another plane or axis of movement.

First multi-axis control pad (674) and second multi-axis control pad (676) are shown as being positioned on different portions of robotic arm (600). In some versions, the particular positioning of multi-axis control pads (674, 676) on robotic arm (600) may be suggestive of the movement of robotic arm (600) each multi-axis control pad (674, 676) may be associated with. For instance, in the present example first multi-axis control pad (674) is positioned distally on head (640) and in line with a specific plane. This positioning may correspond to movement of head (640) about the specific plane associated with first multi-axis control pad (674) such as forward, reverse, left, and right. Meanwhile, second multi-axis control pad (676) is positioned proximate a side of head (640), which may be suggestive of control of distal, proximal, and roll movements of head (640). In addition, or in the alternative, multi-axis control pads (674, 676) may be positioned proximate a joint (612, 622, 632, 634) to be suggestive of control of movement about said joint (612, 622, 632, 634). While multi-axis control pads (674, 676) are shown in FIG. 30, any other suitable kind(s) of user interface features may be integrated into head (640) and/or other portions of a robotic arm (600).

Figure 31:
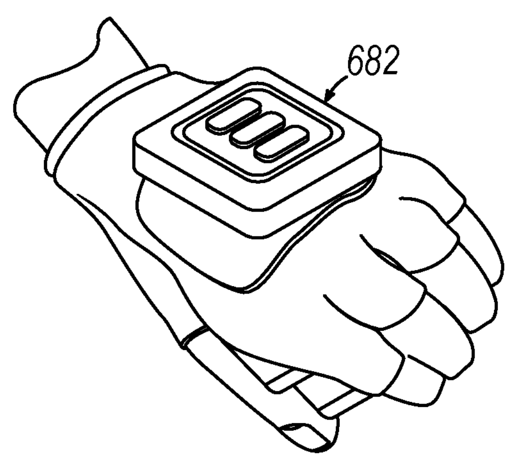
FIG. 31 depicts a perspective view of yet another alternative version of a bedside operator interface feature.

FIG. 31 shows another example of a suitable bedside operator interface feature (682) that may be used with robotic system (500). Beside operator interface feature (682) may be used either in combination with beside operator interface features (652, 662, 672) described above or with any one or more of bedside operator interface features (652, 662, 672) omitted. Bedside operator interface feature (682) may also be viewed as an illustrative example of a form that may be taken by bedside operator interface feature (652). Bedside operator interface feature (682) of the present example is generally configured as a wearable device (e.g., glove) that may be used to control movement of robotic arm (600) by use of an operator's hand or fingers. For instance, bedside operator interface feature (682) may include one or more finger sensors associated with the hand of an operator. Sensors of bedside operator interface feature (682) may include strain sensors and/or similar features that are configured to sense bending of the patient's fingers. In addition, or in the alternative, sensors of bedside operator interface feature (682) may include accelerometers, position sensors, and/or other kinds of sensors that sense one or more portions of the patient's hand changing position or orientation in three-dimensional space. In either case, movement of the operator's hand or fingers may be translated into movement of robotic arm (600) based on data from sensors in bedside operator interface feature (682). In addition, or in the alternative, bedside operator interface feature (682) may include one or more buttons on a surface of bedside operator interface (682) for controlling one or more movements or operations of robotic arm (600).

Figure 32:
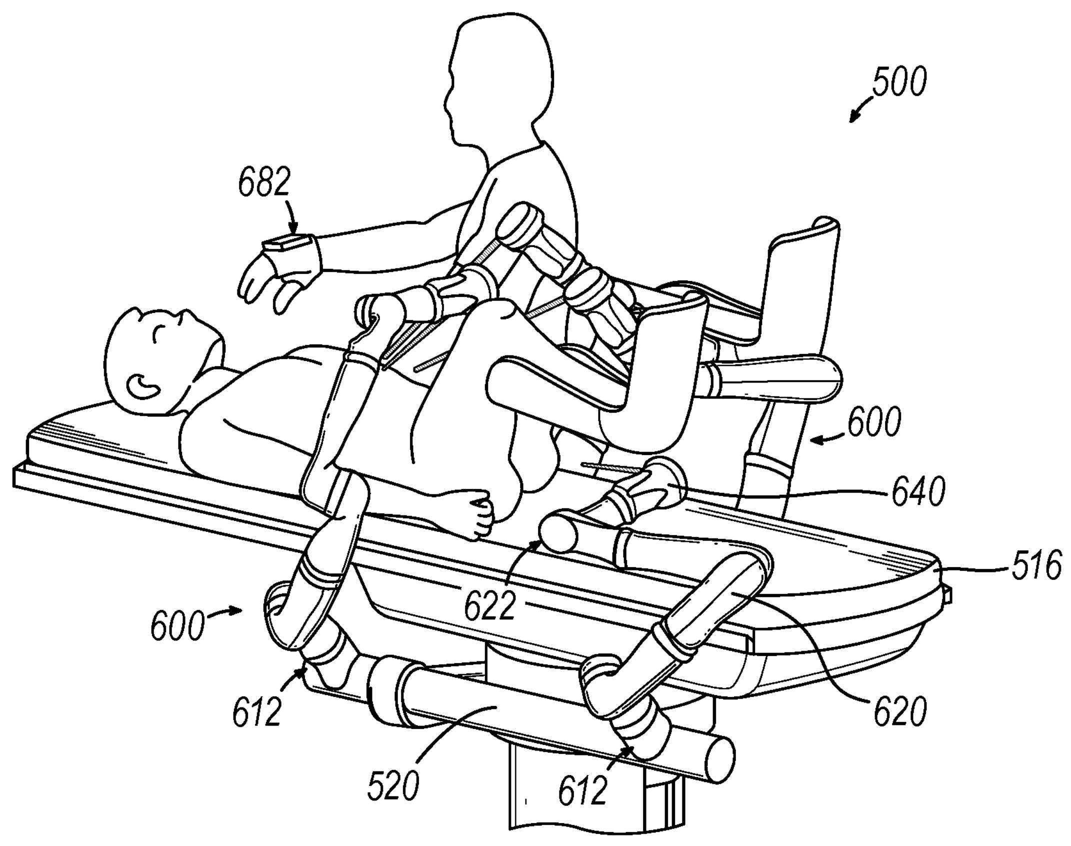
FIG. 32 depicts a perspective view of the bedside operator interface feature of FIG. 31 in use with the table-based robotic system of FIG. 26.

As can be seen in FIG. 32, beside operator interface feature (682) may be used during a procedure in a handsfree mode, which may be activated by one or more buttons. Such a use may be desirable to free the hands of an operator for use in other capacities. For instance, such a user may be desirable in the context of certain hybrid manual and robotic procedures. In such procedures, some procedural steps (e.g., insertion of uterine manipulator (300)) may be performed manually by an operator, while other procedural steps (e.g., manipulation of uterus (U) via uterine manipulator (300)) may be performed via robotic arm (600). Alternatively, beside operator interface feature (682) may be used in any other suitable fashion.

C. Example of Docking Features for Uterine Manipulator

During use of uterine manipulator (300) with robotic arm (600) or other robotic arms (12, 39, 50, 76, 83, 141A, 142B, 200) described herein, it may be desirable to dock or otherwise couple uterine manipulator (300) to robotic arm (600) or other robotic arms (12, 39, 50, 76, 83, 141A, 142B, 200) described herein. Such docking of uterine manipulator (300) to robotic arm (600) may include coupling head interface assembly (310) of uterine manipulator (300) with head (640). In some versions, such docking may occur at various stages during a procedure. Thus, certain structures, features and/or operational steps may be desirable to promote docking of uterine manipulator (300) with a robotic arm (600) automatically or semi-automatically at any stage during a procedure.

Figure 33:
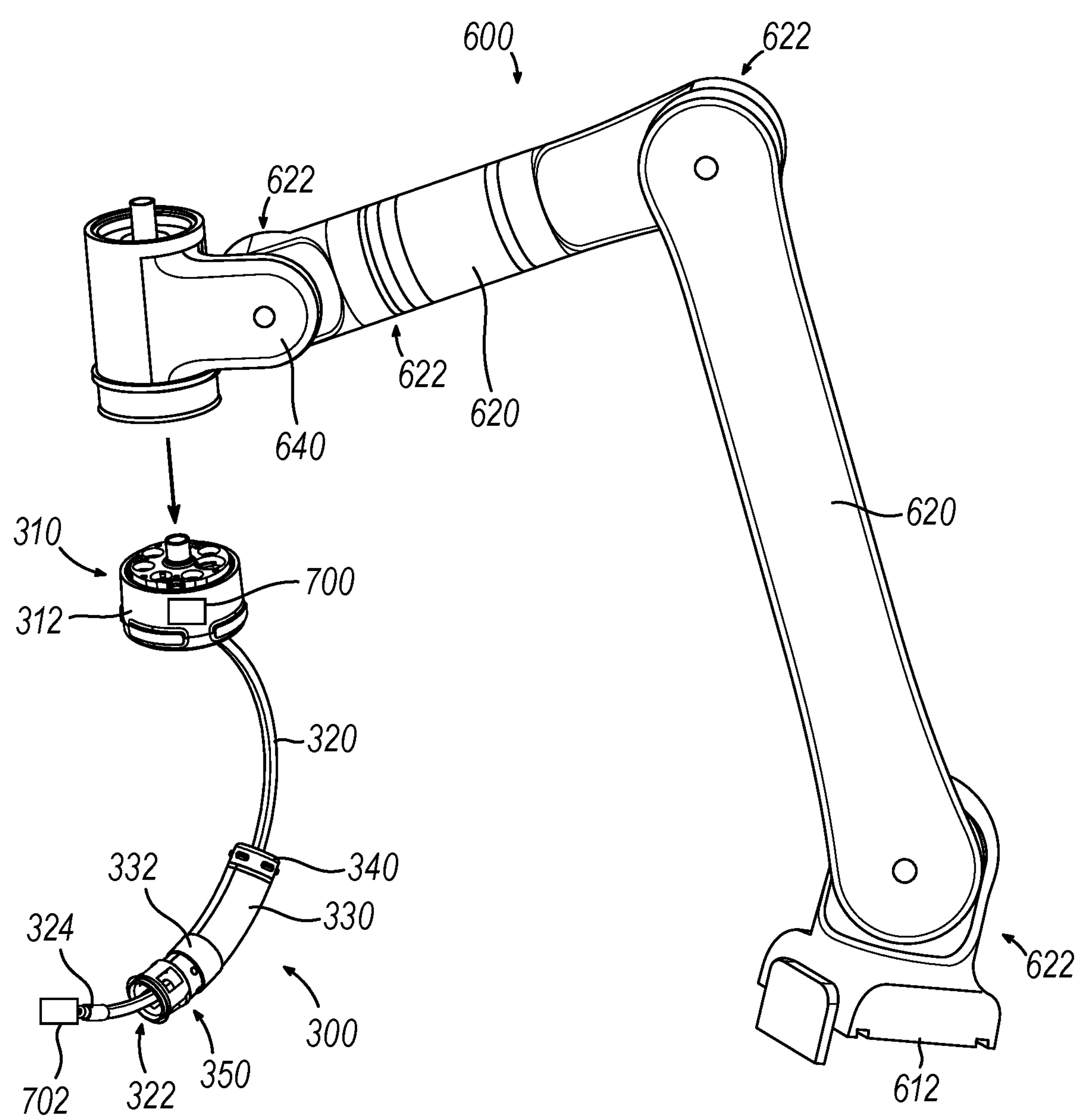
FIG. 33 depicts a perspective view of the robotic arm the uterine manipulator instrument of FIG. 21, the uterine manipulator instrument being docked to the robotic arm.

FIG. 33 shows an example of uterine manipulator (300) docking with robotic arm (600). Although uterine manipulator (300) is shown and described herein as docking with robotic arm (600), it should be understood that in other versions, the same docking described herein may be performed in connection with any other suitable robotic arm including robotic arms (12, 39, 50, 76, 83, 141A, 142B, 200) described herein.

In the present example, robotic arm (600) moves automatically to connect with uterine manipulator (300) as shown in FIG. 33. To assist with alignment between uterine manipulator (300) and robotic arm (600), the present example includes one or more position sensors (700, 702) associated with uterine manipulator (300) and or robotic arm (600). Position sensors (700, 702) may be configured to localize uterine manipulator (300) relative to robotic arm (600) to permit precise control movement of robotic arm (600) toward and into contact with uterine manipulator (300). By way of example only, suitable position sensors (700, 702) may include electromagnetic position markers, optical position markers, proximity sensors, and/or any other suitable kind(s) of sensors. Position sensors (700, 702) in the present example are located with one position sensor (700) on head interface assembly (310) of uterine manipulator (300), and another position sensor (702) on distal end (322) of shaft (320) of uterine manipulator (300). Together, position sensors (700, 702) may be used to localize uterine manipulator (300) relative to a known position of robotic arm (600).

In a fully automatic docking procedure, an operator may hold uterine manipulator (300) stationary. A control module (e.g., within console (652), etc.) may obtain and monitor position data from position sensors (700, 702) to track the real-time position and orientation of uterine manipulator (300) in three-dimensional space. Using this data from position sensors (700, 702), the control module may automatically drive robotic arm (600) to position head (640)

adjacent to head interface assembly (310). While the operator continues to hold uterine manipulator (300) stationary, the control module may continue to automatically drive robotic arm (600) to couple head (640) with head interface assembly (310). To the extent that the operator incidentally moves uterine manipulator (300) during this process, such movement may be detected through data from position sensors (700, 702), and the control module may adjust the movement of robotic arm (600) in real time to ensure that head (640) appropriately reaches and engages the repositioned head interface assembly (310).

In some scenarios, docking of uterine manipulator (300) and robotic arm (600) may be performed semi-automatically. In some such semi-automatic docking modes, an operator may manipulate robotic arm (600) manually toward and into contact with uterine manipulator (300). In some such scenarios, the operator may grasp head (640) with one hand; grasp head interface assembly (310) with the other hand; and then bring head (640) and head interface assembly (310) toward each other. Robotic arm (600) itself or other components associated with robotic arm (600) such as bedside operator interface features (652, 662, 672, 682) may provide haptic feedback to an operator during manipulation to provide feedback during such manipulation. Examples of feedback for an operator during manual manipulation may include warnings when robotic arm (600) approaches certain predetermined zones, feedback based on force sensors or spatial position sensors integrated into robotic arm (600) and/or uterine manipulator (300), etc. Other examples of feedback that may be provided will be apparent to those skilled in the art in view of the teachings herein.

In addition, or in the alternative, semi-automatic docking modes may include one or more geofenced spatial regions associated with movement of robotic arm (600). In use, such geofenced spatial regions may be used to prevent manual manipulation of robotic arm (600) outside of certain predetermined spatial zones. Such geofenced spatial regions may also be used to provide warnings to an operator via haptic feedback described above, audible warnings, and/or visual warnings.

Also in addition, or in the alternative, semi-automatic docking modes may include hybrid manual and robotically controlled movements of robotic arm (600). For instance, in some uses, gross movements of robotic arm (600) may be performed manually by an operator directly manipulating robotic arm (600). Fine and precise movements may then be performed using robotic arm (600) controlled via any one or more of bedside operator interface features (652, 662, 672, 682) described above. As yet another variation, the control module may automatically move robotic arm (600) to position head (640) close to head interface assembly (310) (e.g., based on data from position sensors (700, 702); and then the operator may manually complete the coupling of head interface assembly (310) with head (640).

Figure 34:
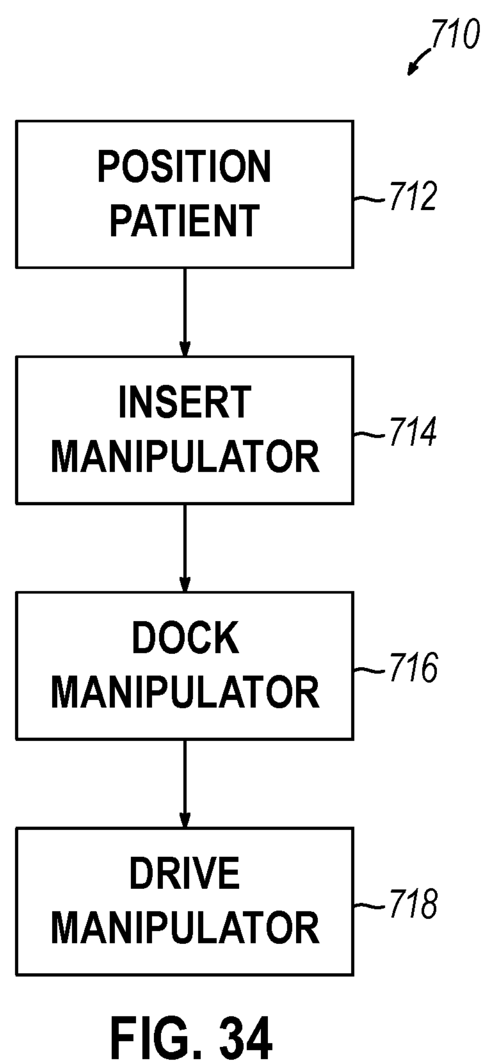
FIG. 34 depicts an exemplary method for docking a uterine manipulator instrument with a robotic arm.

As noted above, docking may occur at various stages during a procedure. For instance, FIG. 34 shows one example of a docking procedure (710) where docking may occur partway through a procedure. As can be seen, the patient may initially be positioned by an operator at block (712). Once the patient is positioned as desired by the operator, uterine manipulator (300) may be inserted into the patient as similarly described above with respect to FIGS. 25A through 25E as shown at block (714). In this example, uterine manipulator (300) is inserted into the patient before head interface assembly (310) is coupled with head (640).

After insertion of uterine manipulator (300) into the patient, docking may then be performed as shown at block (716). At this stage, docking between uterine manipulator (300) and robotic arm (600) may be performed as described above using automatic or semi-automatic operational modes. Once docking is complete, uterine manipulator (300) may be driven by robotic arm (600) as shown at block (718). Such driving of uterine manipulator (300) via robotic arm (600) may include both adjusting the insertion position of uterine manipulator (300) completed at block (714) and/or movement of uterine manipulator (300) to manipulate uterus (U).

Although docking procedure (710) described above contemplates manual insertion and robotic drive thereafter, it should be understood that robotic drive may be used throughout the procedure in some uses. For instance, in some uses docking between uterine manipulator (300) and robotic arm (600) may be completed prior to insertion of uterine manipulator (300) into the patient at block (714). In such uses, uterine manipulator (300) may be inserted into the patient under the control of robotic arm (600). Optionally, an operator may complete such insertion under robotic control using any one or more of bedside operator interface features (652, 662, 672, 682) described above.

In some examples, docking of uterine manipulator (300) to robotic arm (600) may be further facilitated by varying head interface assembly (310). For instance, varying head interface assembly (310) to include different geometric configurations and/or different coupling configurations may facilitate docking by reducing movement required by robotic arm (600) and/or decreasing the force required for docking. In addition, different configurations of head interface assembly (310) may be desirable to promote ease of use with patient anatomy.

Figure 35:
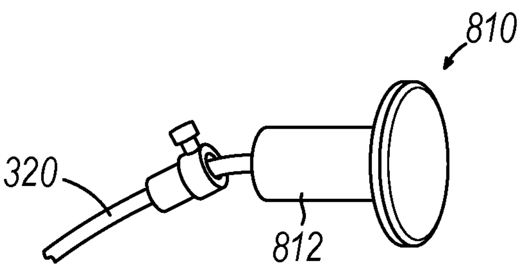
FIG. 35 depicts a perspective view of an alternative version of a head interface assembly that may be incorporated into the uterine manipulator instrument of FIG. 21.

FIG. 35 shows an example of an alternative head interface assembly (810) that may be readily incorporated into uterine manipulator (300). As with head interface assembly (310) described above, head interface assembly (810) of the present example includes a base (812). Base (812) is generally configured to couple to head (640) of robotic arm (600). However, unlike base (312) described above, base (812) of the present example is configured to couple to an opposite side of head (640), which may be configured to support communication of a cannula or a structure similar to shaft (314) of head interface assembly (310). In some versions, shaft (320) passes through head (640) to couple with base (812). Also in some versions, shaft (320) is slidable relative to base (812). In some such versions, base (812) is coupled with sleeve (330). In versions where base (812) is coupled with sleeve (330), sleeve (330) may pass through head (640) to couple with base (812). Alternatively, head (812) may be positioned at the distal side of head (640) with sleeve (330), such that sleeve (330) does not necessarily need to pass through head (640) to couple with base (812) in versions where sleeve (330) is coupled with base (812).

In the configuration described above, the connection between base (812) and head (640) may be simplified to promote ease of docking and/or require less force for docking. This configuration may be desirable in circumstances where fine movement of uterine manipulator (300) is desired or low force inputs are needed. However, due to the simplified coupling, robotic arm (600) may only provide physical manipulation of uterine manipulator (300) without motor-based manipulation for structures such as sleeve (330).

Figure 36:
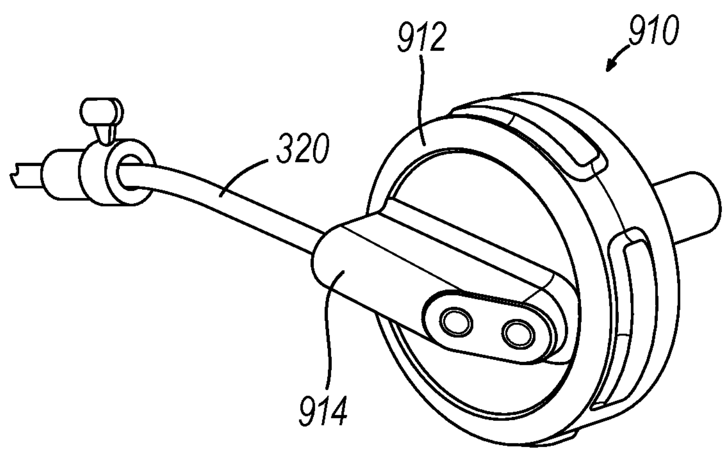
FIG. 36 depicts a perspective view of another alternative version of a head interface assembly that may be incorporated into the uterine manipulator instrument of FIG. 21.

FIG. 36 shows another example of a head interface assembly (910) that may be readily incorporated into uterine manipulator (300). Head interface assembly (910) of the present example is generally substantially similar to head interface assembly (310) described above. For instance, head interface assembly (910) of the present example includes a base (912) configured couple to head (640) of robotic arm (600) to support structures similar to shaft (320). However, unlike base (312) described above, base (912) of the present example includes a side mount (914) configured to permit structures similar to shaft (320) to extend laterally from base (912) rather than axially like base (312) described above.

In some examples, lateral extension of structures similar to shaft (320) from base (912) may be desirable to provide a different orientation of robotic arm (600) when in use during a procedure. In some versions, the availability of either head interface assembly (910) or head interface assembly (310) to an operator may be desirable to provide improved flexibility to support an operator's preferred angle of attack and/or patient position.

Figure 37:
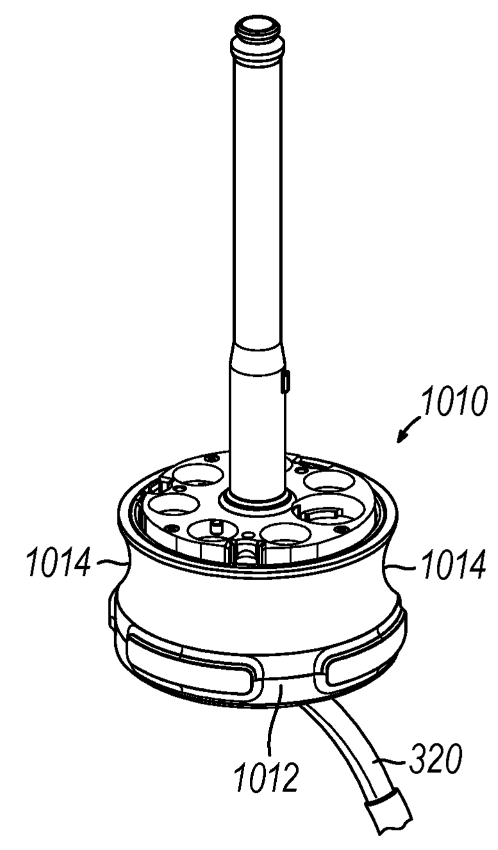
FIG. 37 depicts a perspective view of yet another alternative version of a head interface assembly that may be incorporated into the uterine manipulator instrument of FIG. 21.

FIG. 37 shows yet another example of a head interface assembly (1010) that may be readily incorporated into uterine manipulator (300). Head interface assembly (1010) of the present example is generally substantially similar to head interface assembly (310) described above. For instance, head interface assembly (1010) of the present example includes a base (1012) configured couple to head (640) of robotic arm (600) to support structures similar to shaft (320). However, unlike base (312) described above, base (1012) of the present example defines an indentation (1014) around the circumference of base (1012). Indentation (1014) is generally configured to provide a double-hilt configuration to base (1012). In other words, base (1012) defines two ridges on either side of indentation (1014), which may be used to provide improved grip on base (1012) by an operator's hand. Such an improved grip may be desirable in circumstances where uterine manipulator (300) is manually docked to robotic arm (600)—preventing axial slippage of an operator's fingers as force is applied to uterine manipulator (300). Alternatively, any other suitable features may be incorporated into base (1012) to promote grasping of base (1012).

IV. Example of Feedback Detection Features for Robotically Controlled Uterine Manipulator In versions where uterine manipulator (300) is manipulated robotically, challenges may be encountered if there is a lack of real-time feedback associated with manipulation. For instance, movement of uterine manipulator (300) within patient anatomy may limit the ability to visualize some or all of the uterine manipulator (300), which may lead to uncertainty as to the position of uterine manipulator (300) relative to patient anatomy. Movement of the patient during a procedure may further contribute to uncertainty as to the position of uterine manipulator (300) relative to patent anatomy. Similarly, movement of uterine manipulator (300) without a sense of the force being applied to (or by) uterine manipulator (300) may lead to the unnecessary application of force to sensitive patient anatomy. Accordingly, it may be desirable to incorporate certain features into uterine manipulator (300) or associated structures and/or components to provide real-time feedback as to the spatial position of uterine manipulator (300), the amount of force being applied to uterine manipulator (300), and/or the amount of force being applied by uterine manipulator (300) to adjacent tissue.

A. Example of Features to Automatically Define Remote Center of Motion

Remote center of motion is a concept that may be used in certain minimally invasive procedures where a robotically controlled instrument or tool is inserted through a trocar or other kind of access port. In such procedures, it may be desirable for the trocar or other access port to remain at a fixed insertion position, and impart only minimal force at the trocar-tissue interface, because the trocar or other kind of access port may interface with sensitive patient anatomy. The concept of the remote center of motion may be used in software architecture to facilitate fixation of the trocar or other kind of access port while the instrument or tool extends through the trocar or other kind of access port and is moved relative to the trocar or other kind of access port. In this context, the remote center of motion may be established at or near the a point where the instrument or tool interfaces with the trocar or other kind of access port. The software architecture is then set to move the instrument or tool relative to the remote center of motion to minimize forces imparted at the corresponding trocar-tissue interface.

In some procedures, an instrument is inserted into a patient via a naturally occurring orifice instead of being inserted via a trocar. An example of such a procedure is one in which a uterine manipulator like uterine manipulator (300) is used. In such procedures, the remote center of motion may be defined at or near the point at which the instrument enters the naturally occurring orifice. In the context of a procedure where uterine manipulator (300) is used, the remote center of motion may be defined at or near the opening of the vagina (V). Because of this, establishing a remote center of motion in this context may vary by patient anatomy (e.g., based on the depth of the vagina (V), which may vary from patient to patient). The combination of various patient anatomy factors to arrive at a specific remote center of motion may be referred to herein as a patient specific remote center of motion.

The patient specific remote center of motion in the context of use of structures similar to uterine manipulator (300) may generally correspond to the opening of the vagina (V). More specifically, this may be at a depth of about 5 cm inside the vagina (V) from the opening thereof. Thus, in some instances, the patient specific remote center of motion may be identified relative to a tissue-air interface corresponding to the opening of the vagina (V). Other factors that may be used to determine the patient specific remote center of motion may include, for example, the position of the urethra, ureter anatomy, bone structures, and/or other anatomical features.

In examples where a patient specific remote center of motion is used, certain algorithms may be used to assist with control of robotic arms such as robotic arms (600) described above. In some instances, such algorithms may be used to control the position of structures of a uterine manipulator (300), such as distal end (322) of shaft (320), using the patient specific remote center of motion. For instance, one example of an algorithm may utilize the Jacobian pseudo-inverse to compute the robotic arm (600) joint angles needed to achieve a desired distal end (322) position while maintaining the patient specific remote center of motion.

The Jacobian algorithm may be used to compute which direction and how quickly to move robotic arm (600) joints (622) corresponding to a desired change at distal end (322) or patient specific remote center of motion. In some versions, the algorithm may be used iteratively to converge toward a desired position. For instance, the Jacobian may first be computed and one or more small step in the desired direction may be taken. The Jacobian may then be recomputed fur further subsequent one or more small steps.

Figure 38:
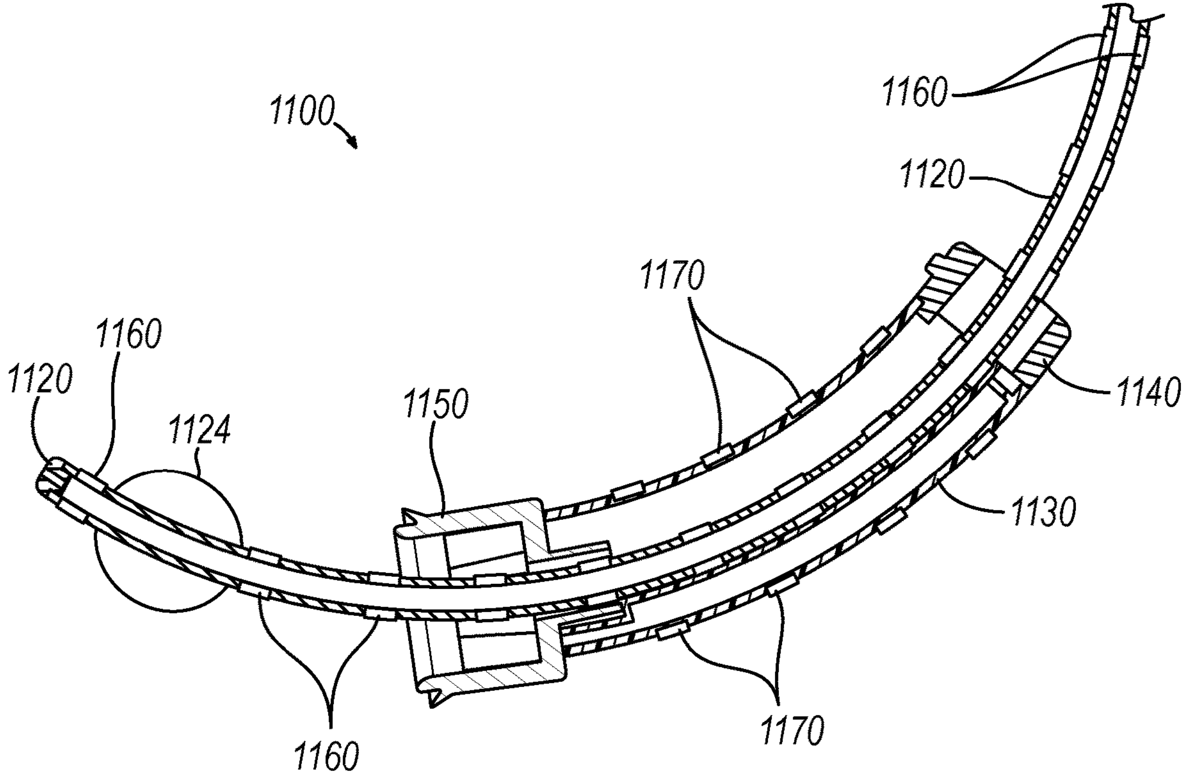
FIG. 38 depicts a side elevational view of an alternative version of a uterine manipulator instrument.

FIG. 38 shows an example of a uterine manipulator (1100) that includes features to automatically set a patient specific remote center of motion based the particular anatomy of the patient at hand. Although certain features for automatically setting a patient specific remote center of motion are described herein in the context of uterine manipulator (1100), it should be understood that the same features may be applied in other contexts such as where a robotic instrument or tool is used with a trocar.

Uterine manipulator (1100) is substantially similar to uterine manipulator (300) described above. For instance, although not shown, uterine manipulator (1100) may include a head interface assembly, substantially similar to head interface assembly (310), configured to couple uterine manipulator (300) to robotic arm (600) or other suitable structures. Similarly, uterine manipulator (1100) includes a shaft (1120), a sleeve (1130), a sleeve locking ring (1140), and a colpotomy cup (1150). Shaft (1120) of the present example is substantially similar to shaft (320) described above. For instance, shaft (1120) extends distally from a base (not shown) of the head interface assembly (not shown) along a curve. Similarly, an inflatable balloon (1124) is positioned near distal end (1122) of shaft (1120). Balloon (1124) is likewise substantially similar to balloon (324) described above and may be formed of an extensible material or a non-extensible material. The interior of shaft (1120) includes one or more lumen(s) that are configured to communicate pressurized fluid to balloon (1124).

Sleeve (1130) is substantially similar to sleeve (330) described above with sleeve (1130) of the present example being slidably coupled to shaft (1120). As such, sleeve (1130) may slide along shaft (1120) through a plurality of positions such as those described above with respect to FIGS. 21, 22, and 25B-25E. As with sleeve (330) described above, sleeve (1130) of the present example is generally cylindraceous and rigid; and extends along a curved axis such that the curved lateral profile complements the curved lateral profile of shaft (1120).

Locking ring (1140) is substantially similar to locking ring (340) described above. For instance, locking ring (1140) of the present example is rotatably secured to the proximal end of sleeve (1130), while colpotomy cup (1150) is fixedly secured to the distal end of sleeve (1130). As with locking ring (340) described above, locking ring (1140) is operable to selectively secure the position of sleeve (1130) along the length of shaft (1120).

Although not shown, it should be understood that sleeve (1130) may include structures similar to inflatable balloon (332) described above. As with inflatable balloon (332), such an inflatable balloon may be positioned along sleeve (1130), between locking ring (1140) and colpotomy cup (1150).

Colpotomy cup (1150) is substantially similar to colpotomy cup (350) described above. For instance, colpotomy cup (1150) of the present example may include structures similar to body (352), interior space (354), floor (358), open distal end (360), lateral openings (356), annular edges (364, 362), etc.

Unlike uterine manipulator (300) described above, uterine manipulator (1100) of the present example includes one or more sensor arrays (1160, 1170) disposed on one or more surfaces of uterine manipulator (1100). As will be described in greater detail below, sensor arrays (1160, 1170) may be configured to detect the position of uterine manipulator (1100) itself relative to patient anatomy and/or various components of uterine manipulator (1100) relative to other components of uterine manipulator (1100). Although sensor arrays (1160, 1170) are characterized herein as arrays of sensors, it should be understood that in other versions, each array of sensors (1160, 1170) may be configured as a single sensor or several sensors grouped in varying patterns. In addition, or in the alternative, in some versions, each array of sensors (1160, 1170) may be omitted and functionality described herein may be replicated via other structures such as optical scales to detect the position of uterine manipulator (1100) relative to a patient; or encoders to detect the position of one component of uterine manipulator (1100) relative to another component of uterine manipulator (1100).

Uterine manipulator (1100) of the present example includes an array of shaft sensors (1160) associated with shaft (1120) and an array of sleeve sensors (1170) associated with sleeve (1130). Shaft sensors (1160) are longitudinally spaced apart from each other along the length of shaft (1120). While a plurality of shaft sensors (1160) are used in the present example, other variations may provide just one single elongate sensor (1160) extending longitudinally along the length of shaft (1120). Shaft sensors (1160) are generally configured to detect the position of sleeve (1130) relative to shaft (1120). As will be described in greater detail below, this detection information may be combined with information from sleeve sensors (1170) to locate the position of uterine manipulator (1100) relative to anatomy of a patient. In addition to, or as an alternative to, detecting the position of sleeve (1130) relative to shaft (1120), shaft sensors (1160) may be configured to detect the position of shaft (1160) within the patient (e.g., the depth to which shaft (1120) is inserted into the uterus (U).

In some versions, each shaft sensor (1160) includes a capacitive sensor, though shaft sensors (1160) may take any other suitable form (e.g., optical sensors, hall effect sensors, etc.). In yet other versions, shaft sensors (1160) may instead include a scale of optical or electromagnetic markers. In such versions, a single sensor may instead be incorporated into sleeve (1130) to detect the position of sleeve (1130) on shaft (1120). In still other versions, shaft sensors (1160) may be omitted entirely and an encoder associated with positioning of sleeve (1130) may be used to detect the position of sleeve (1130) relative to shaft (1120).

Sleeve sensors (1170) are longitudinally spaced apart from each other along the length of sleeve (1130). While a plurality of sleeve sensors (1170) are used in the present example, other variations may provide just one single elongate sensor (1170) extending longitudinally along the length of sleeve (1130). Sleeve sensors (1170) are generally configured to detect the position of sleeve (1130) relative to patient anatomy. For instance, in the present example, each sleeve sensor (1170) includes an impedance sensor (e.g., an electrode pair). In versions where sleeve sensors (1170) includes several impedance sensors, sleeve sensors (1170) that are in contact with the wall of the vagina (V) may detect impedance values associated with tissue; while sleeve sensors (1170) that are outside of the vagina (V) may detect impedance values associated with air. The insertion depth of sleeve (1130) in the vagina (V) may thus be detected based on how many of sleeve sensors (1170) are detecting impedance values associated with tissue. Put another way, sleeve sensors (1170) may be used to detect the tissue-air interface described above, to in turn detect the position of sleeve (1130) relative to the opening of the vagina (V). In addition, or in the alternative, sleeve sensors (1170) may be used to detect the interface between different tissue types corresponding to anatomical features of the patient, as the impedance may vary based on the tissue type.

Although sleeve sensors (1170) of the present example are described above as including impedance sensors, it should be understood that in other versions various alternative sensors may be used in addition to or as an alternative to impedance sensors. For instance, in some versions, sleeve sensors (1170) may include force sensors that are operable to detect the differences in force applied to sleeve (1130) along the longitudinal length thereof. In other versions, sleeve sensors (1170) may include optical sensors or moisture sensors to detect the tissue-air interface. Alternatively, any other suitable kind(s) of sensors may be used for sleeve sensors (1170) as will be apparent to those skilled in the art in view of the teachings herein.

Figure 39:
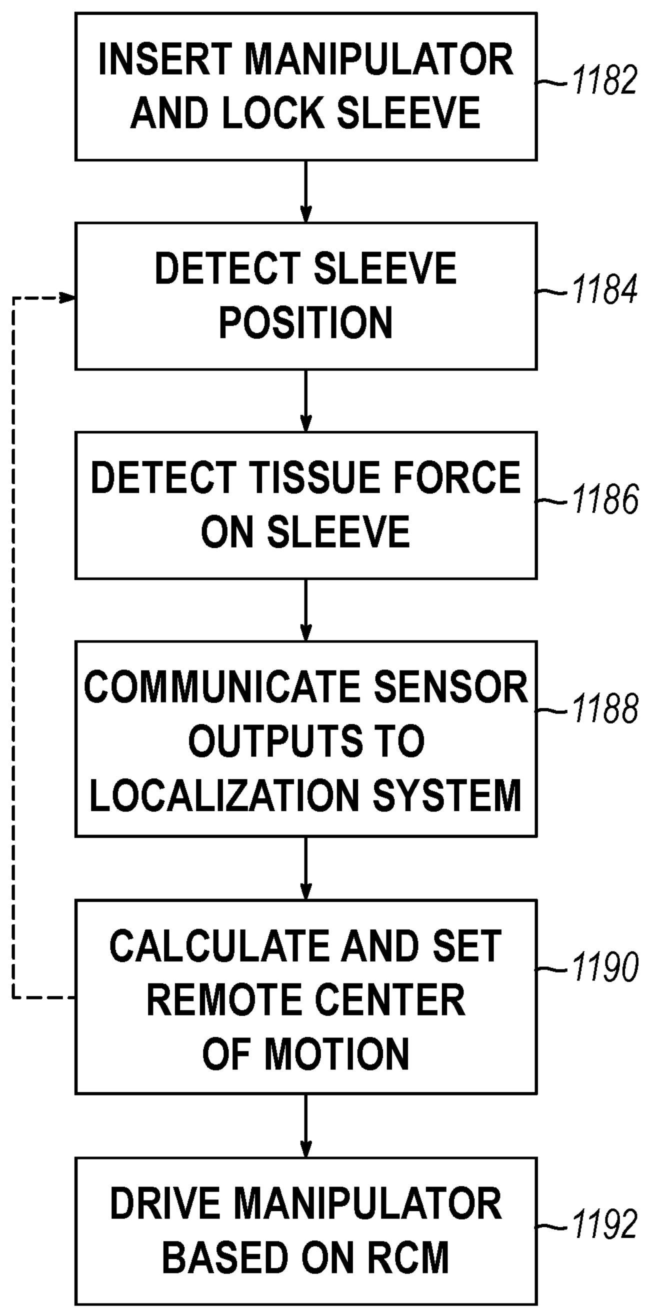
FIG. 39 depicts an exemplary method for use with the uterine manipulator instrument of FIG. 38.

FIG. 39 shows an exemplary use of uterine manipulator (1100) of the present example in the context of establishing a remote center of motion. In use, uterine manipulator (1100) may initially be inserted into a patient as shown at block (1182). Insertion of uterine manipulator (1100) may be substantially similar to insertion procedures described above with respect to uterine manipulator (300). For instance, some versions of insertion may be performed manually. Similarly, other versions of insertion may be performed robotically, either automatically or semi-automatically.

Regardless of the particular insertion procedure, once uterine manipulator (1100) is inserted into a patient, the position of sleeve (1130) may be detected using sensors (1160, 1170) as shown at block (1184). At this stage, the position of sleeve (1130) may be detected relative to patient anatomy using sleeve sensors (1170). As described above, this may be performed by, for example, detecting the tissue-air interface to approximate the position of sleeve (1130) relative to an opening of a patient's vagina (V). Similarly, the position of sleeve (1130) relative to shaft (1120) may also be detected using shaft sensors (1160). As described above, this may be performed by, for example, tracking movement of sleeve (1130) relative to shaft (1120) using capacitive sensors, optical sensors, hall effect sensors, etc.

Once the position of sleeve (1130) relative to both patient anatomy and relative to shaft (1120) is detected, one or more sensors (1160, 1170) may next be optionally used to detect tissue force applied to sleeve (1130) as shown at block (1186). For instance, as described above, some versions of sleeve sensors (1170) may include force sensors configured to detect force applied to sleeve (1130). Such force sensors may additionally be in an array to permit force vectoring that may be used to detect both the force applied generally and the direction of such force.

After detection of the position of sleeve (1130), and optionally the force applied to sleeve (1130), such detection may be communicated to a localization system or other computational components as shown at block (1188). Such computational components may be provided in a console or in any of the other various hardware components described herein. Once the detection information is communicated, such information may be used to calculate a patient specific remote center of motion for uterine manipulator (1100) as shown at block (1190). This patient specific remote center of motion may be calculated by a combination of the position of sleeve (1130) relative to patient anatomy and the position of sleeve (1130) relative to shaft (1120). Optionally, if force on sleeve (1130) is detected, such force may also be used to calculate the patient specific remote center of motion.

In some scenarios, the remote center of motion that is calculated at block (1190) may be established at the tissue-air interface opening of the vagina (V). In some other scenarios, the remote center of motion may be established at a predetermined distance from the tissue-air interface opening of the vagina (V). For instance, the remote center of motion may be established at a depth of about 5 cm inside the vagina (V) from the tissue-air interface opening of the vagina (V). As yet another variation, the remote center of motion may be established at a calculated distance from the tissue-air interface opening of the vagina (V) (e.g., a calculated depth inside the vagina (V) from the tissue-air interface opening of the vagina (V)), where the distance is calculated based on the patient anatomy parameters sensed by sensors (1160, 1170) and/or other parameters sensed by sensors (1160, 1170).

Once the patient specific remote center of motion is calculated, uterine manipulator (1100) may be driven robotically by a robotic system such as robotic system (500) as shown at block (1192). Such robotic driving of uterine manipulator (1100) may include using uterine manipulator (1100) to reposition and/or reorient the uterus (U) as described above. During driving of uterine manipulator (1100), motion at the patient specific remote center of motion may be limited to avoid excessive trauma near the patient specific remote center of motion.

Optionally, during driving of uterine manipulator (1100), the integrity of the patient specific remote center of motion may be maintained by continuously monitoring the position of sleeve (1130). Specifically, at any point after calculation of the patient specific remote center of motion shown at block (1190), the process may return to detecting the position of sleeve (1130) as shown at block (1184). The process of detecting the position of sleeve (1130) relative to both patient anatomy and shaft (1120) may then be repeated to continuously update or recalculate the patient specific remote center of motion. This may be desirable in some versions to account for movement of uterine manipulator (1100) relative to anatomy of a patient during the course of a procedure.

B. Example of Features to Detect Patient Movement

In some instances, tracking the position of uterine manipulator (1100) as described above may be sufficient to maintain the appropriate position of uterine manipulator (1100) and thereby avoid unnecessary trauma to sensitive patient anatomy. However, in other instances, tracking of the position of sleeve (1130) relative to patent anatomy and relative to shaft (1120) alone may be insufficient. For instance, in some circumstances, a patient may move during a procedure. Some instances of patent movement may be detectable via detection of the position of sleeve (1130) relative to patient anatomy. However, other instances of patent movement may be only partially detectable via detection of the position of sleeve (1130) relative to patient anatomy. Thus, it may be desirable to detect patient movement separately from the detection methods and structures described above. Moreover, even if all instance of patient movement may be detectable via detection of the position of sleeve (1130) relative to patient anatomy, it may still be desirable to separately detect patient movement to improve operational efficiencies or to provide secondary mechanisms for ensuring integrity of a patient specific center of motion throughout a procedure.

Figure 40:
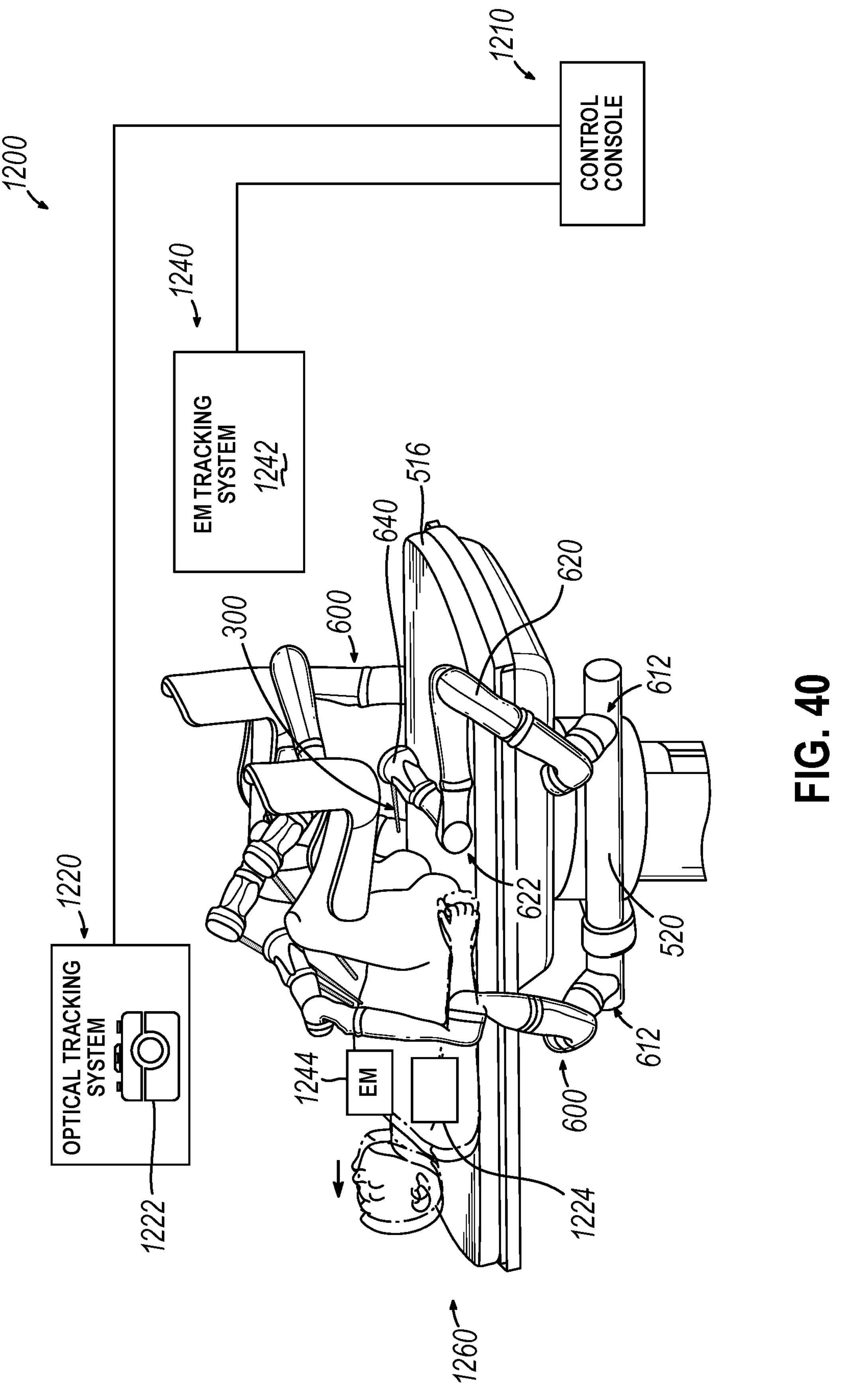
FIG. 40 depicts a schematic view of an exemplary patient tracking system.

FIG. 40 shows an example of a patient tracking system (1200). As can be seen, patient tracking system (1200) includes a console (1210) in communication with an optical tracking assembly (1220) and an electromagnetic tracking assembly (1240). Console (1210) in the present example is substantially similar to console (30) described above. For instance, as similarly described above, console (1210) may include a user interface and a display screen for use by an operator. Console (1210) may likewise be configured to provide both robotic controls as well as pre-operative and real-time information such as navigational and localization information.

Optical tracking assembly (1220) is generally configured to communicate patient tracking information to console (1210) so that such information may be used to calculate and/or update a patient specific remote center of motion for a uterine manipulator such as uterine manipulators (300, 1100) described above. Optical tracking assembly (1220) includes an optical sensor (1222) and one or more optical position markers (1224). Optical sensor (1222) is generally configured to detect the position of one or more optical position markers (1224) in space. In some versions, optical sensor (1222) comprises a camera. Some versions of optical sensor (1222) may also include a source of light. It should therefore be understood that optical sensor (1222) may be configured to both emit and detect various wavelengths of light. In some versions, optical sensor (1222) is also used for other purposes (e.g., providing overhead visualization of the surgical procedure), such that optical sensor (1222) need not necessarily be dedicated solely to use as a component of optical tracking assembly (1220).

In the present example, optical position marker (1224) of optical tracking assembly (1220) is fixedly secured to the patient, such that optical position marker (1224) will move with the patient if the patient moves. Optical position marker (1224) may have any suitable form that enables optical position marker (1224) to be readily optically detected and tracked by optical sensor (1222). Although only a single optical position marker (1224) is shown, it should be understood that multiple optical position markers (1224) may be used. Additionally, although optical position marker (1224) of the present example is shown as being positioned proximate a patient's chest, it should be understood that in other examples, optical position marker (1224) may be positioned in various other suitable positions on the patient. In operation, optical tracking assembly (1220) and control console (1210) cooperate to provide optical tracking of optical position marker (1224) via optical sensor (1222). By tracking any movement of optical position marker (1224), optical tracking assembly (1220) and control console (1210) cooperate to provide optical tracking of patient movement.

Electromagnetic tracking assembly (1240) is generally configured to communicate patient tracking information to console (1210) so that such information may be used to calculate and/or update a patient specific remote center of motion for a uterine manipulator such as uterine manipulators (300, 1100) described above. As will be described in greater detail below, electromagnetic tracking assembly (1240) may be used either alone as an alternative to optical tracking assembly (1220); or in combination with optical tracking assembly (1220). Thus, some versions may provide patient movement tracking through a combination of optical tracking and electromagnetic tracking.

Electromagnetic tracking assembly (1240) of the present example includes an electromagnetic field generator (1242) and one or more electromagnetic sensors (1244). Electromagnetic field generator (1242) is configured to maintain a fixed position in relation to the patient. Electromagnetic field generator (1242) is also configured generate an electromagnetic field around the patient, with the electromagnetic field being positioned to reach electromagnetic sensors (1244). In response to the electromagnetic field generated by electromagnetic field generator (1242), each electromagnetic sensor (1244) generates electrical signals that are indicative of the position of electromagnetic sensor (1244) in three-dimensional space. In some variations, each electromagnetic sensor (1244) comprises a coil. In some such variations, each electromagnetic sensor (1244) comprises a multi-axis coil assembly.

Each electromagnetic sensor (1244) is fixedly secured to the patient, such that electromagnetic sensor (1244) will move with the patient if the patient moves. Although only a single electromagnetic sensor (1244) is shown, it should be understood that multiple electromagnetic sensors (1244) may be used. Additionally, although electromagnetic sensor (1244) of the present example is shown as being positioned proximate a patient's chest, it should be understood that in other examples, electromagnetic sensor (1244) may be positioned in various other suitable positions on the patient. In any case, position-indicative signals generated via each electromagnetic sensor (1244) may be communicated back to control console (1210) via wire or wirelessly. Control console (1210) may process these signals to track movement of each electromagnetic sensor (1244); and thereby track movement of the patient.

In some other variations of electromagnetic tracking assembly (1240), each electromagnetic sensor (1244) is replaced with a field generator that is operable to generate an electromagnetic field. In such versions, electromagnetic field generator (1242) may be replaced with a fixed-position electromagnetic sensor that is operable to detect the electromagnetic field generated by each electromagnetic sensor (1244), such that the fixed-position electromagnetic sensor may sense movement of the patient by sensing movement of the electromagnetic field generated by the electromagnetic field generator that is fixedly secured to the patient. Alternatively, electromagnetic tracking assembly (1240) may take any other suitable form.

In use, a patient may be positioned on a patient table (1260). In the present example, patient table (1260) is shown in the Trendelenburg position. In this position, a patient is oriented at an angle with the head being lower than the legs. Use of patient tracking system (1200) may be desirable in the Trendelenburg position because a patient may be more prone to movement when oriented at an angle. However, use of patent tracking system (1200) may also be desirable in contexts where other patient positions are used.

As shown, the patient may spontaneously or continuously slide downwardly during a procedure. Such sliding may be detected by optical tracking assembly (1220), electromagnetic tracking assembly (1240), or a combination of both optical tracking assembly (1220) and electromagnetic tracking assembly (1240). When such sliding is detected by one or more of optical tracking assembly (1220) or electromagnetic tracking assembly (1240), console (1210) may be configured to automatically pause manipulation of a uterine manipulator, such as uterine manipulators (300, 1100) described above, via a robotic system such as robotic system (500) described above. Console (1210) may then provide an alert to an operator, which the operator may either ignore or use to initiate an automatic recalculation to a patient specific remote center of motion. In addition, the position, orientation, and/or configuration of one or more robotic arms (600) may be adjusted in response to patient movement being detected by one or both of optical tracking assembly (1220) or electromagnetic tracking assembly (1240).

An automatic recalculation of the patient specific remote center of motion may be at least partially based on information from one or more of optical tracking assembly (1220) or electromagnetic tracking assembly (1240). Additionally, such automatic recalculation may also be based on information from other sensors such as sensor arrays (1160, 1170) in uterine manipulator (1100) described above. Various combinations of information from one or more of optical tracking assembly (1220), electromagnetic tracking assembly (1240), or sensor arrays (1160, 1170) may be desirable to promote more a more precisely recalculated patient specific remote center of motion.

C. Example of Features to Detect Force Applied to Robotically Controlled Uterine Manipulator As discussed above, certain sensors may be beneficial to detect the position of a uterine manipulator such as uterine manipulator (1100) described above relative to patient anatomy. While such sensors may be beneficial to set and maintain a patient specific remote center of motion to avoid trauma to sensitive patient anatomy, some application of force to patient anatomy may be unavoidable or even necessary during a procedure. Thus, it may be desirable to incorporate features into structures similar to uterine manipulator (1100) or robotic arms (600) to detect force application. Such force detection features may be beneficial to permit some application of force to patient anatomy, while maintaining such application of force below levels that may lead to undesirable trauma to patient anatomy.

Figure 41:
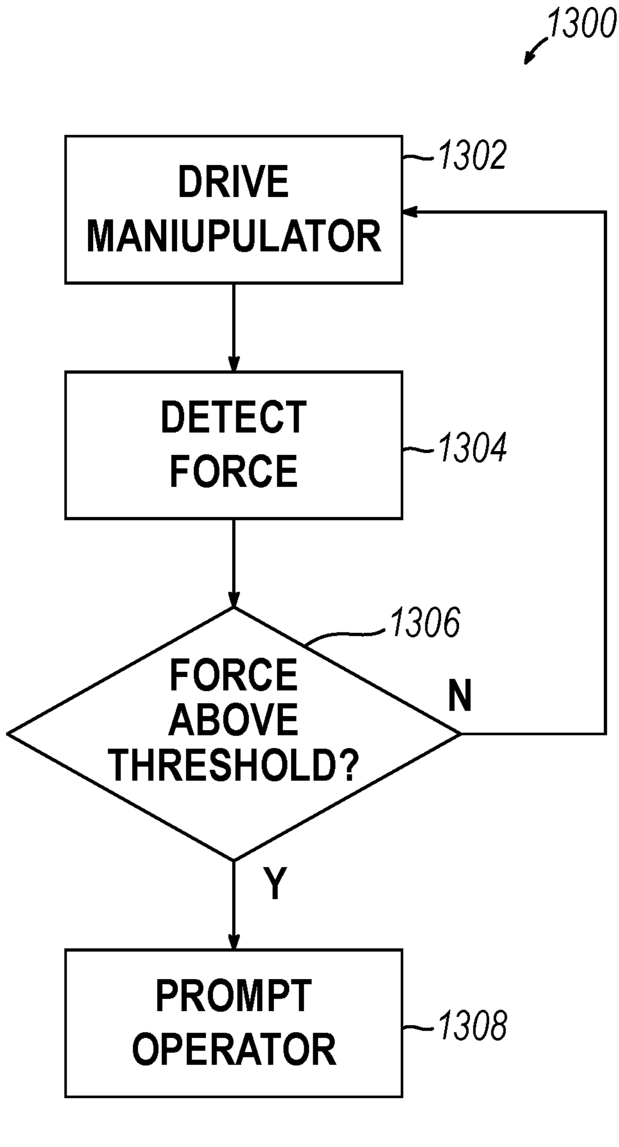
FIG. 41 depicts an exemplary force detection method.

FIG. 41 shows an example of a force detection method (1300) for use with a robotically controlled uterine manipulator similar to uterine manipulator (1100) described above. Force detection method (1300) begins with driving of a uterine manipulator similar to uterine manipulator (1100) described above at block (1302). Although force detection method (1300) begins with driving the uterine manipulator, it should be understood that other steps may be performed prior to driving the uterine manipulator. For instance, prior to driving uterine manipulator, insertion may be performed as similarly described above with respect to uterine manipulators (300, 1100). Similarly, setting and maintaining of a patient specific remote center of motion may also be performed as described above with respect to uterine manipulator (1100).

Regardless, when driving the uterine manipulator, a level of force applied to the uterine manipulator and/or to patient tissue may be detected as shown at block (1304). As will be described in greater detail below, detection of the level of force may be performed using features associated with the uterine manipulator itself and/or features associated with a robotic arm used to drive the uterine manipulator.

Once the level of force is detected, the detected level of force may be compared to one or more predetermined threshold levels as shown at block (1306). If the detected level of force is at or below the one or more predetermined threshold levels, the method may continue driving the uterine manipulator as described above with respect to block (1302). Detection of force (block (1304) and comparison of the detected force (block (1306)) may continue in a loop until a detected level of force above the one or more predetermined threshold levels is identified.

Once a detected force above the one or more predetermined threshold levels is detected, an operator may be prompted as shown at block (1308). As will be described in greater detail below, the specific operator prompt may take a variety of forms. For instance, an operator may receive a visual, haptic, and/or auditory warning. In addition, or in the alternative, a system stop may be initiated with an operator being required to override the system stop to proceed. Such a system stop may include ceasing movement of whichever robotic arm (600) is associated with the force exceeding the threshold. In addition, or in the alternative, the detected level of force may be presented to an operator in graphical or numeric form. In some scenarios, the force exceeding the threshold may indicate that the operator is not using the uterine manipulator properly. In some other scenarios, the force exceeding the threshold may indicate that the operator failed to remove enough connective tissue from the uterus (U) before manipulating the uterus (U) with the uterine manipulator. Alternatively, the force exceeding the threshold may indicate other conditions.

Figure 42:
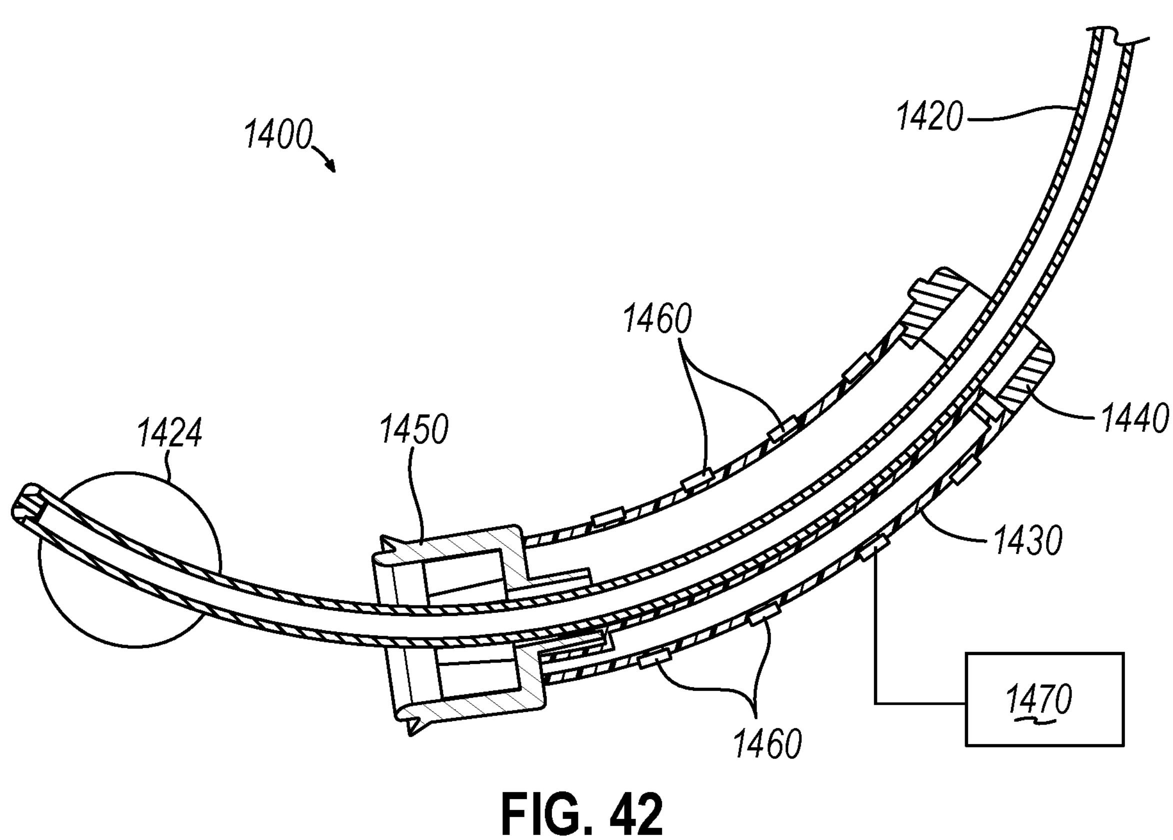
FIG. 42 depicts a perspective view of an alternative version of a uterine manipulator instrument for use with the force detection method of FIG. 41.

FIG. 42 shows an example of a uterine manipulator (1400) that may be used in connection with force detection method (1300) described above. Uterine manipulator (1400) is substantially similar to uterine manipulators (1100, 300) described above. For instance, uterine manipulator (1400) of the present example includes a shaft (1420) having an inflatable balloon (1424), a sleeve (1430) configured to move along the length of shaft (1420), a sleeve locking ring (1440) configured to lock sleeve (1430) in a selected longitudinal position relative to shaft (1420), and a colpotomy cup (1450). Such structures are substantially similar to corresponding structures described above such that further details are omitted herein.

Unlike uterine manipulators (300, 1100) described above, uterine manipulator (1400) of the present example includes an array of force sensors (1460) associated with sleeve (1430). The array of force sensors (1460) in this example includes one or more force sensors or load cells arranged about the outer surface of sleeve (1430) to detect a force applied to sleeve (1430). In the present example, force sensors (1460) include a plurality of load cells arranged to cover the length and circumference of the outer surface of sleeve (1430). Force sensors (1460) are therefore configured to detect force applied to sleeve (1430) at multiple positions along the length of sleeve (1430) or around the circumference of sleeve (1430).

As can be seen, force sensors (1460) may be in communication with a console (1470) similar to consoles (16, 31, 650, 1210) described above. Thus, console (1470) may be configured to receive force information from force sensors (1460) to process, interpret, and communicate force information to an operator. For instance, in some versions, console (1470) may be configured to combine force information from multiple force sensors (1460) to identify the force applied to sleeve (1430) generally, the approximate location(s) on sleeve (1430) where force is applied, and/or the direction(s) of the applied force.

Figure 43:
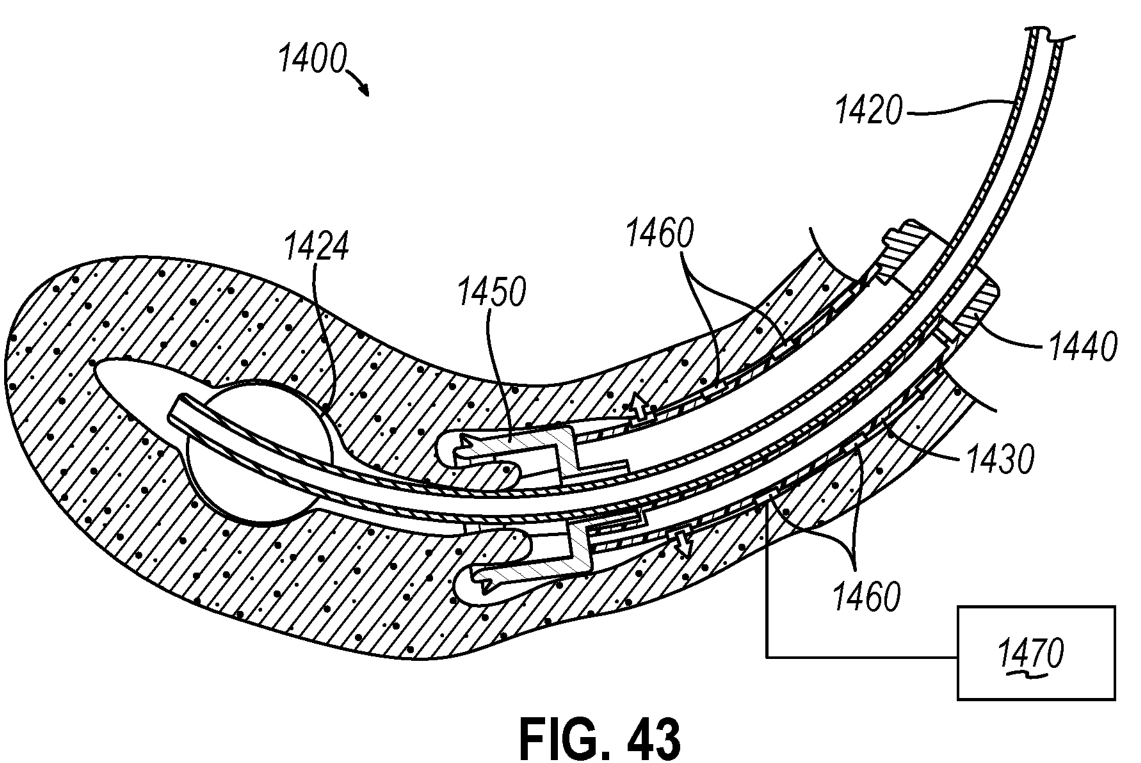
FIG. 43 depicts another perspective view of the uterine manipulator instrument of FIG. 41, with the uterine manipulator instrument being used to detect force applied to patient anatomy.

FIG. 43 shows use of uterine manipulator (1400) in connection with force detection method (1300) described above (see FIG. 41). In use, force sensors (1460) may be used to detect the force applied by tissue (e.g., vagina (V)) to sleeve (1430) as shown at block (1304). In the present example, force values may be detected along the entire length of sleeve (1430). Moreover, the locations of force values at different longitudinal regions along sleeve (1430) may be determined. Being able to determine force values at different longitudinal regions along sleeve (1430) may facilitate determination of force values at or near a patient specific remote center of motion. In some cases, it may be particularly beneficial to determine force values at or near a patient specific remote center of motion. For instance, it may be desirable to minimize forces at or near a patient specific remote center of motion.

Once the force is detected, console (1470) may be used to compare the detected force to one or more predetermined threshold levels. In some versions, different predetermined threshold levels may be assigned based on the anatomical location, such that different force sensors (1460) may be associated with different threshold levels (i.e., based on the position of each force sensor (1460) along the length of sleeve (1430)). For instance, force sensors (1460) at positions corresponding to the patient specific remote center of motion may have a lower associated force threshold than force sensors (1460) at positions corresponding to the distal region of sleeve (1430). If one or more threshold levels is exceeded by the detected force, console (1470) may provide one or more warnings to an operator. Such warnings may be in the form of audible warnings, haptic warnings, visual warnings, and/or in other forms. Additionally, if multiple predetermined thresholds are used, different warnings may be used depending on which predetermined thresholds are exceeded. In some versions, if one or more threshold levels are exceeded, console (1470) may initiate a system stop that may require operator confirmation prior to proceeding with driving of uterine manipulator (1400).

Although uterine manipulator (1400) is shown as only including the array of force sensors (1460) on sleeve (1430), some other versions of uterine manipulator (1400) may include other sensor arrays in addition to the array of force sensors (1460). For instance, in some versions, force sensors (1460) may be combined with other sensor arrays such as sleeve sensors (1170) described above. In such examples, force information may be combined with position information to set and maintain a patient specific remote center of motion and/or provide real-time feedback to an operator related to the operational status of uterine manipulator (1400). Similarly, while only sleeve (1430) has force sensors (1460) in this example, some other variations may also include force sensors along at least a portion of shaft (1420) and/or elsewhere on uterine manipulator (1400).

Figure 44:
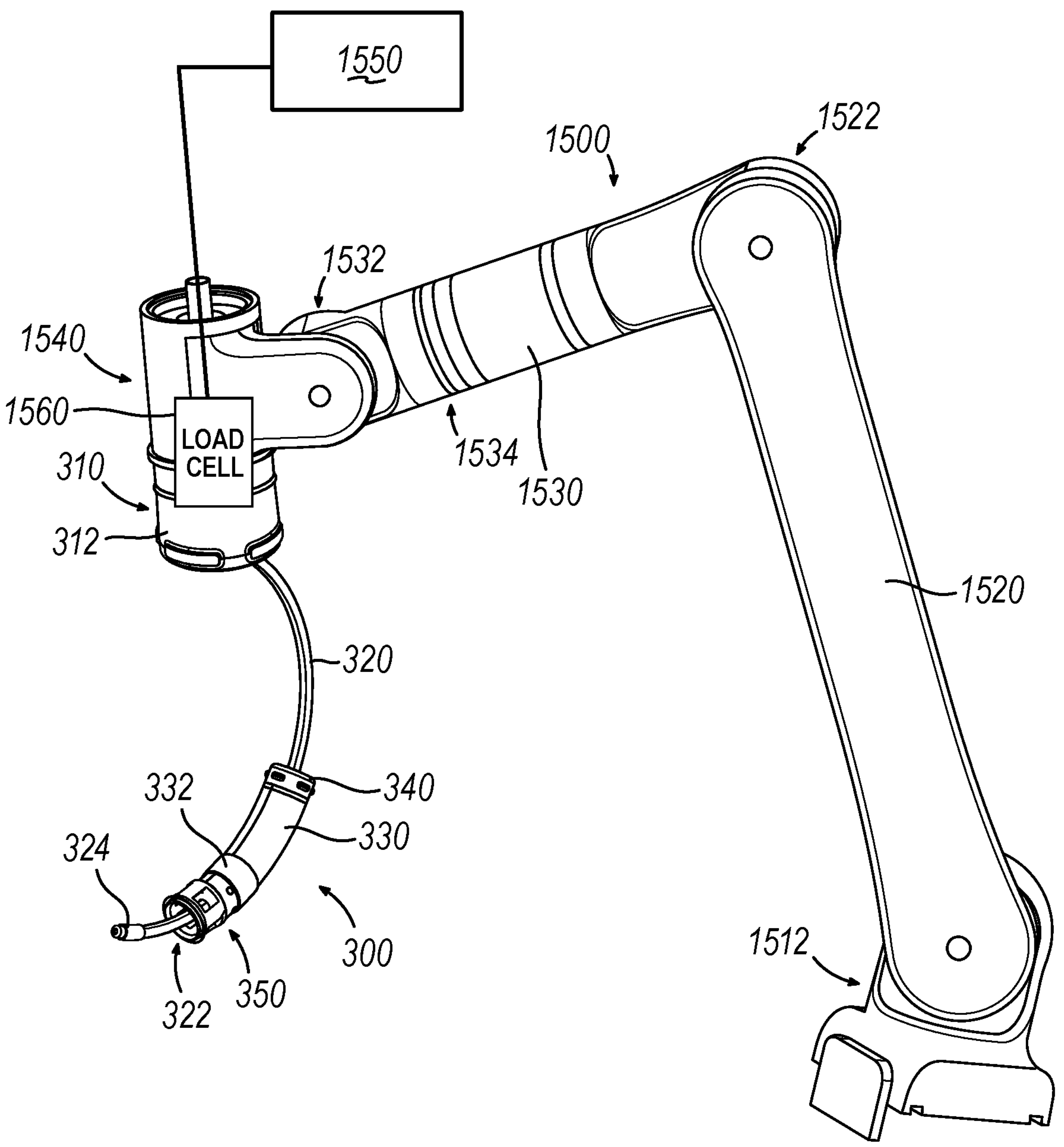
FIG. 44 depicts a perspective view of an alternative version of a robotic arm for use with the uterine manipulator instrument of FIG. 21.

FIG. 44 shows an example of a robotic arm (1500) that may be used in connection with force detection method (1300) described above to detect force applied to a robotically controlled uterine manipulator such as uterine manipulators (300, 1100, 1400) described above. Although robotic arm (1500) of the present example is shown as being used in connection with uterine manipulator (300), it should be understood that in other versions, robotic arm (1500) may be readily used with uterine manipulators (1100, 1400) described above.

Robotic arm (1400) of the present example is substantially similar to robotic arms (200, 600) described above. For instance, robotic arm (1400) includes joints (1512, 1522, 1532, 1534), arm segments (1520, 1530), which may be configured to manipulate a head (1540). Such structures are substantially similar to corresponding structures described above, such that further details are omitted herein.

Unlike robotic arms (600) described above, robotic arm (1400) of the present example includes a load cell (1560) within head (1540). Lead cell (1560) is generally configured to sense force applied to an instrument such as uterine manipulators (300, 1100, 1400). For instance, in the present example load cell (1560) is configured to sense a force applied to uterine manipulator (300) by detecting the force between head (1540) and head interface assembly (310). This force detected by load cell (1560) may be indicative of the force being applied by uterine manipulator (300) to tissue. While only one load cell (1560) is shown, some variations may provide two or more load cells (1560) to provide further information regarding the forces applied at the interface between head (1540) and head interface assembly (310), etc.

As can be seen, load cell (1560) may be in communication with a console (1550) similar to consoles (16, 31, 650, 1210, 1470) described above. Thus, console (1550) may be configured to receive force information from load cell (1560) to process, interpret, and communicate force information to an operator. For instance, in some versions, console (1550) may be configured to receive force information from load cell (1560) and translate such force information into a format suitable for interpretation by an operator. In addition, or in the alternative, load cell (1560) may be configured in some versions to provide multi-variable force information with force vectoring. In such versions, console (1550) may be configured to combine such force information with related positional information to identify the force applied to uterine manipulator (300) generally, the approximate location(s) on uterine manipulator (300) where force is applied, and/or the direction(s) of the applied force.

In some versions, load cell (1560) may be used with uterine manipulator (300) to perform force detection method (1300) described above with respect to FIG. 41. In use, load cell (1560) may be used to detect the force applied to uterine manipulator (300) by robotic arm (1500), which may approximate the force being applied to tissue (e.g., vagina (V)) via sleeve (1530) as shown at block (1304). While load cell (1560) is shown as being positioned in head (1540) in the present example, one or more load cells (1560) may be positioned elsewhere within robotic arm (1500). Moreover, one or more load cells (1560) may be positioned within uterine manipulator (300). By way of example only, one or more load cells (1560) may be positioned in head interface assembly (310) of uterine manipulator (300).

Once the force is detected via load cell (1560), console (1550) may be used to compare the detected force to one or more predetermined threshold levels. If one or more threshold levels is exceeded by the detected force, console (1550) may provide one or more warnings to an operator. Such warnings may be in the form of audible warnings, haptic warnings, visual warnings, and/or etc. Additionally, if multiple predetermined thresholds are used, different warnings may be used depending on which predetermined thresholds are exceeded. In some versions, if one or more threshold levels are exceeded, console (1550) may initiate a system stop that may require operator confirmation prior to proceeding with driving of uterine manipulator (300).

Figure 45:
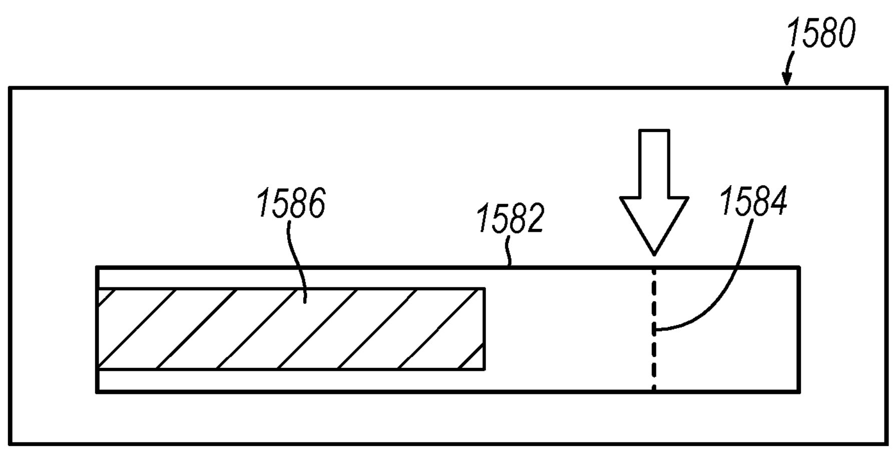
FIG. 45 depicts a schematic view of a graphical force indicator for use with the force detection method of FIG. 41.

FIG. 45 shows an exemplary graphical force indicator (1580) that may be used in connection with console (1550) (or console (1470)) to display a detected force to an operator. Graphical force indicator (1580) in the present example is generally configured as a bar graph or bar chart. In other versions, graphical force indicator (1580) may that on a variety of forms such as an instrument meter (e.g., round display having a needle). Additionally, or in the alternative, some versions of graphical force indicator (1580) may include digital numerical readout of both a detected force and various threshold force levels.

Graphical force indicator (1580) of the present example includes a force scale (1582), a threshold indicator (1584), and a force indicator (1586). Force scale (1582) is a passive feature that provides a continuum from zero force to a predetermined maximum force. Force indicator (1586) may graphically move relative to the continuum provided by force scale (1582) to indicate relative force provided to an operator. Threshold indicator (1584) is disposed at a predetermined point along force scale (1582). Thus, threshold level (1584) is configured to indicate to an operator when a detected force is approaching or exceeds a predetermined threshold level. In some versions, threshold level (1584) may be operator selectable such that an operator may set one or more preferred threshold levels. Although the present example includes only a single threshold indicator (1584), it should be understood that in other versions multiple threshold indicators (1584) may be used.

Although robotic arm (1500) is described herein as being used with uterine manipulator (300), it should be understood that in other versions, robotic arm (1500) may be used with any other suitable uterine manipulators (1100, 1400). For instance, although load cell (1560) may be beneficial in some examples to provide some detectable force, it may be beneficial to also have force information as detected by force sensors (1460) of uterine manipulator (1400). Thus, in some versions load cell (1560) and force sensors (1460) may be used together to provide more detailed force information. In other versions, other sensor arrays may be used, such as shaft sensors (1160) and sleeve sensors (1170), in combination with load cell (1560) and/or force sensors (1460). Such versions may be desirable to provide detailed force information combined with detailed position information. In such versions, force information may be combined with position information to set and maintain a patient specific remote center of motion and/or provide real-time feedback to an operator related to the operational status of any one of uterine manipulators (300, 1100, 1400).

D. Example of Features to Localize Robotically Controlled Uterine Manipulator

As described above, in some examples it may be desirable to locate features of structures similar to uterine manipulators (300, 1100, 1400) described above relative to patient anatomy. In the examples described above, such localization features described above may be beneficial to locate a patient specific remote center of motion relative to patient anatomy. However, it may also be beneficial to locate other features of a uterine manipulator similar to uterine manipulators (300, 1100, 1400) relative to patient anatomy or relative to other instruments or tools.

Figure 46:
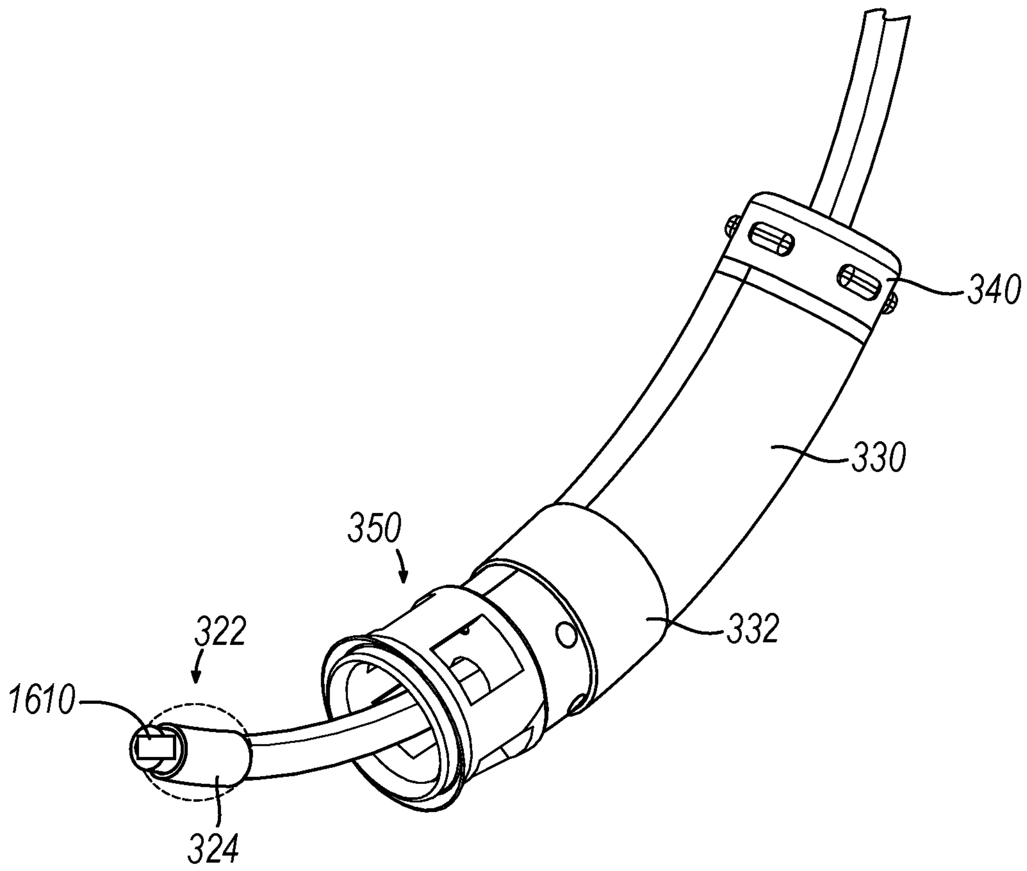
FIG. 46 depicts a perspective view of the uterine manipulator instrument of FIG. 21 having a manipulator position marker of an instrument localization system.
Figure 47:
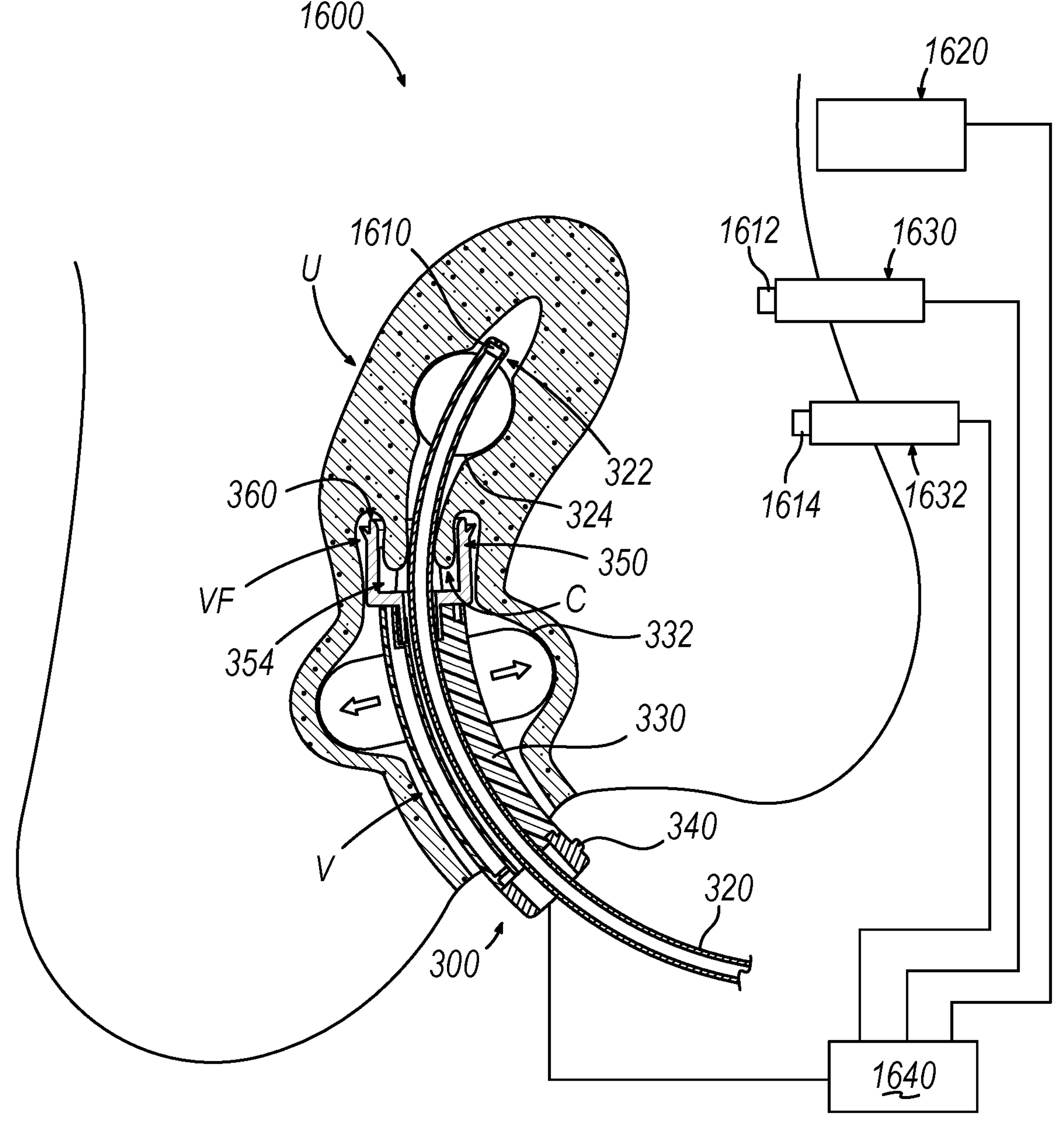
FIG. 47 depicts a schematic view of the uterine manipulator instrument of FIG. 21 in use with the instrument localization system of FIG. 46.

FIGS. 46 and 47 show use of uterine manipulator (300) described above in connection with an example of an instrument localization system (1600). Although instrument localization system (1600) is shown and described herein as being used in connection with uterine manipulator (300), it should be understood that in other versions, instrument localization system (1600) may be readily used with other uterine manipulators (1100, 1400). For instance, in some examples it may be desirable to use instrument localization system (1600) in combination with features of either uterine manipulator (1100) or uterine manipulator (1400) to obtain localization information in combination with position information and/or force information described above.

As best seen in FIG. 46, instrument localization system (1600) includes a manipulator position marker (1610). In the present example, manipulator position marker (1610) is configured as an electromagnetic position sensor (e.g., similar to electromagnetic position sensor (1244) described above), although it should be understood that alternative position markers may be used in other versions. Manipulator position marker (1610) is positioned at or near distal end (322) of shaft (320). As will be described in greater detail below, this positioning of manipulator position marker (1610) may be configured to localize distal end (322) of shaft (320) in space. Although manipulator position marker (1610) is described herein in association with distal end (322), it should be understood that in other versions manipulator position marker (1610) may be positioned on other portions of uterine manipulator (300).

In some other versions, multiple manipulator position markers (1610) may be positioned at different positions along uterine manipulator, such that multiple manipulator position markers (1610) may be used to generally locate uterine manipulator (300) and to locate specific portions of uterine manipulator (300) relative to other portions of uterine manipulator (300). Thus, multiple manipulator position markers (1610) may providing detection of the orientation of one or more portions of uterine manipulator (300) in addition to providing detection of the position of one or more portions of uterine manipulator (300).

As best seen in FIG. 47, instrument localization system (1600) further includes a procedure room emitter (1620) and a plurality of instrument position markers (1612, 1614). Procedure room emitter (1620) is operable to generate an electromagnetic field (e.g., similar to electromagnetic field generator (1242) described above). Procedure room emitter (1620) may be positioned within a procedure room but outside of a patient, while instrument position markers (1612, 1614) may be positioned within a patient. Instrument position markers (1612, 1614) may be positioned on a distal end of each laparoscopic instrument or tool used in a procedure in addition to uterine manipulator (300). For instance, in the present example a first instrument (1630) and a second instrument (1632) are shown as being inserted into a patient's abdomen. Thus, a first instrument position marker (1612) corresponds to first instrument (1630) and a second instrument position marker (1614) corresponds to second instrument (1632). By way of example only, instruments (1630, 1632) may include trocars, laparoscopes, cutting instruments, tissue graspers, RF instruments, and/or any other suitable kind of instrument that may be inserted into an abdomen of a patient. In some versions, additional instruments or tools may be used. In such versions, additional corresponding emitters may likewise be used.

Like electromagnetic field generator (1242) described above, procedure room emitter (1620) may be positioned at a fixed location external to the patient. Procedure room emitter (1620) may nevertheless be positioned and configured to generate an electromagnetic field that may reach manipulator position marker (1610) and instrument position markers (1612, 1614) within the patient.

In use, instrument localization system (1600) is generally configured to precisely track and localize uterine manipulator (300) during various stages of use such as docking, insertion, and/or manipulation. Similarly, instrument localization system (1600) is generally configured to track and localize instruments (1630, 1632) during all stages of operation. Tracking and localization may be provided in a variety of ways. For instance, the position of procedure room emitter (1620) may be known and may be used to identify the location of manipulator position marker (1610) and/or instrument position markers (1612, 1614) in relation to procedure room emitter (1620). Position markers (1610, 1612, 1614) may thus be used to determine the real-time positions of uterine manipulator (300) and instruments (1630, 1632) in relation to a global frame of reference (e.g., the frame of reference provided by procedure room emitter (1620); and in relation to each other.

Once the location of manipulator position marker (1610) is known, this information may be used in a variety of ways. For instance, in some versions, the location of manipulator position marker (1610) may be used to provide overlays on an operator display to thereby provide feedback related to the position of uterine manipulator (300) both relative to patient anatomy and relative to other instruments or tools such as instruments (1630, 1632). In addition, or in the alternative, such tracking may be used during either manual operation of uterine manipulator (300) or during robotically driven operation of uterine manipulator (300). In other versions, the location of manipulator position marker (1610) may be used to warn an operator of certain operational conditions such as the possibility of perforation through the tissue of the vagina (V) or uterus (U). In yet other versions, the location of manipulator position marker (1610) may be used in connection with automatic robotic procedures such as automatic docking described above. The locations of instruments (1630, 1632) as indicated by instrument position markers (1612, 1614) may also be used to inform the operator via a display, etc. Alternatively, the position data obtained through instrument localization system (1600) may be used in any other suitable fashion.

In some versions, each position marker (1610, 1612, 1614) is configured to generate electrical signals that are indicative of the position of electromagnetic sensor (1244) in three-dimensional space, in response to an electromagnetic field generated by procedure room emitter (1620). In some variations, each position marker (1610, 1612, 1614) comprises a coil. In some such variations, each position marker (1610, 1612, 1614) comprises a multi-axis coil assembly. Although instrument localization system (1600) of the present example is described as using electromagnetic tracking, it should be understood that other kinds of tracking systems may be used. For instance, in some versions, instrument localization system (1600) may use optical tracking in addition to, or in lieu of, electromagnetic tracking. In such examples, optical position markers may be secured to portions of uterine manipulator (300), first instrument (1630), and/or second instrument (1632) that will be exposed relative to the patient during operation. In addition, or in the alternative, position tracking may be achieved using robotic kinematics and/or any other suitable techniques.

V. Examples of Combinations

The following examples relate to various non-exhaustive ways in which the teachings herein may be combined or applied. The following examples are not intended to restrict the coverage of any claims that may be presented at any time in this application or in subsequent filings of this application. No disclaimer is intended. The following examples are being provided for nothing more than merely illustrative purposes. It is contemplated that the various teachings herein may be arranged and applied in numerous other ways. It is also contemplated that some variations may omit certain features referred to in the below examples. Therefore, none of the aspects or features referred to below should be deemed critical unless otherwise explicitly indicated as such at a later date by the inventors or by a successor in interest to the inventors. If any claims are presented in this application or in subsequent filings related to this application that include additional features beyond those referred to below, those additional features shall not be presumed to have been added for any reason relating to patentability.

Example 1

A system, comprising: (a) a robotic platform, including: (i) a base, (ii) a plurality of robotic arms, and (iii) a grounding structure configured to couple one or more of the robotic arms to the base; and (b) a uterine manipulator, including: (i) an interface configured to couple with a first robotic arm of the robotic platform, (ii) a shaft assembly extending from the interface, and (iii) a colpotomy cup slidably attached along a length of the shaft assembly, wherein the first robotic arm is configured to move the uterine manipulator relative to a patient.

Example 2

The system of Example 1, the robotic platform further including a patient table, wherein the grounding structure is positioned proximate a side of the patient table.

Example 3

The system of any of Examples 1 through 2, wherein the grounding structure includes an elongate rail, wherein the first robotic arm is slidably disposed on the elongate rail.

Example 4

The system of Example 3, wherein the grounding structure is configured to robotically move the first robotic arm along a length defined by the grounding structure.

Example 5

The system of any of Examples 3 through 4, wherein the grounding structure is configured to permit the first robotic arm to be moved manually along a length defined by the grounding structure.

Example 6

The system of any of Examples 1 through 5, wherein the grounding structure is configured to move relative to the patient table.

Example 7

The system of any of Examples 1 through 6, wherein the grounding structure is configured to support the robotic arm relative to a patient with the robotic arm being positioned over a leg of the patient with the robotic arm approaching the patient from a lateral side of the patient.

Example 8

The system of any of Examples 1 through 7, wherein the grounding structure is configured to support the robotic arm relative to a patient with the robotic arm being positioned under a leg of the patient with the robotic arm approaching the patient from a lateral side of the patient.

Example 9

The system of any of Examples 1 through 8, wherein the robotic platform further includes a console and an operator interface feature, wherein the operator interface feature is separate from the console.

Example 10

The system of Example 9, wherein the operator interface feature includes one or more robotic control buttons configured to initiate movement of the first robotic arm.

Example 11

The system of any of Examples 9 through 10, wherein the operator interface feature is incorporated into at least a portion of the first robotic arm.

Example 12

The system of any of Examples 9 through 11, wherein the operator interface feature includes a wearable robotic user interface.

Example 13

The system of any of Examples 9 through 12, wherein the operator interface feature includes one or more multi-axis control pads.

Example 14

The system of any of Examples 9 through 13, wherein the operator interface feature includes a haptic feedback device.

Example 15

The system of any of Examples 1 through 14, wherein the robotic platform further includes a second robotic arm, wherein the second robotic arm is configured to support one or more endoscopic or laparoscopic instruments.

Example 16

A system, comprising: (a) a robotic platform, including: (i) a plurality of robotic arms, (ii) a console having a first user interface, the console being configured for remote positioning relative to the plurality of robotic arms, and (iii) a bedside control interface in communication with, and separate from, the console; and (b) a uterine manipulator configured to couple with at least one robotic arm of the plurality of robotic arms, wherein the beside control interface is operable to drive movement of the uterine manipulator via the at least one robotic arm.

Example 17

The system of Example 16, wherein the bedside control interface is coupled to a first robotic arm of the plurality of robotic arms.

Example 18

The system of any of Examples 16 through 17, wherein the bedside control interface is coupled to a portion of the uterine manipulator.

Example 19

The system of any of Examples 16 through 18, wherein the bedside control interface is configured as a handheld interface for movement relative to the plurality of robotic arms.

Example 20

The system of any of Examples 16 through 19, wherein the beside control interface includes a wearable component, wherein the wearable component is configured to respond to one or more movements of an operator.

Example 21

The system of any of Examples 16 through 20, wherein the bedside control interface is configured to control precise movements of the uterine manipulator.

Example 22

The system of any of Examples 16 through 21, wherein the bedside control interface is in communication with another portion of the robotic platform via one or more wires.

Example 23

The system of any of Examples 16 through 22, wherein the bedside control interface is in communication with another portion of the robotic platform via a wireless connection.

Example 24

A method for control of a uterine manipulator, comprising: (a) inserting the uterine manipulator into a patient to a first position, wherein the insertion of the uterine manipulator is performed manually; (b) moving the uterine manipulator within the patient to a second insertion position, wherein the step of moving the uterine manipulator is performed using a bedside control feature; and (c) manipulating a uterus of the patient via the uterine manipulator, wherein the step of manipulating the uterus is performed using a console separate from the bedside control feature to drive movement of the uterine manipulator.

Example 25

The method of Example 24, wherein the step of moving the uterine manipulator includes driving movement of a robotic arm using the bedside control feature.

Example 26

The method of any of Examples 24 through 25, wherein the second insertion position corresponds to a final insertion position of the uterine manipulator prior to manipulating the uterus of the patient.

Example 27

The method of any of Examples 24 through 26, further comprising further manipulating the uterus of the patient using the uterine manipulator, wherein the step of further manipulating the uterus is performed using the bedside control feature.

Example 28

The method of any of Examples 24 through 27, wherein the step of moving the uterine manipulator within the patient is performed in combination with the bedside control feature and manual movement of the uterine manipulator.

Example 29

An apparatus, comprising: (a) a base portion configured to selectively couple with a robotic arm; (b) a shaft extending distally form the base portion and terminating into a distal end; (c) a sleeve slidably coupled to the shaft; (d) a colpotomy cup fixedly secured to a portion of the sleeve; and (e) a plurality of sensors, wherein the sensors are configured to locate the position of the sleeve relative to one or more anatomical features of a patient, wherein the sensors are further configured to locate the position of the sleeve relative to the shaft.

Example 30

The apparatus of Example 29, wherein the plurality of sensors define a first sensor array associated with the shaft and a second sensor array associated with the sleeve.

Example 31

The apparatus of Example 30, wherein the first sensor array includes a plurality of shaft sensors longitudinally spaced apart from each other along a length of the shaft.

Example 32

The apparatus of any of Examples 30 through 31, wherein the second sensor array includes a plurality of sleeve sensors longitudinally spaced apart from each other along an outer surface of the sleeve.

Example 33

The apparatus of any of Examples 30 through 32, wherein the first sensor array comprises a capacitive sensor array configured to detect the position of the sleeve relative to the shaft.

Example 34

The apparatus of any of Examples 30 through 33, wherein the second sensor array comprises a plurality of impedance sensors configured to sense a presence of tissue.

Example 35

The apparatus of Example 34, wherein the impedance sensors are configured to identify a tissue-air interface.

Example 36

The apparatus of any of Examples 29 through 35, wherein the plurality of sensors includes an encoder, wherein the encoder is associated with a motor for moving the sleeve relative to the shaft.

Example 37

The apparatus of any of Examples 29 through 36, wherein the shaft includes visual indicia, wherein the plurality of sensors includes an optical sensor configured to sense the visual indicia.

Example 38

The apparatus of any of Examples 29 through 37, wherein the shaft includes visual indicia, wherein the plurality of sensors includes an optical sensor secured to the sleeve, wherein the optical sensor is configured to track movement of the visual indicia of the shaft relative to the sleeve.

Example 39

The apparatus of any of Examples 29 through 38, wherein at least one sensor of the plurality of sensors is configured to detect the presence of tissue.

Example 40

A system, comprising: (a) the apparatus of any of Examples 29 through 39; and (b) a controller, wherein the controller is in communication with the plurality of sensors, wherein the controller is configured to compute a remote center of motion based on information from the plurality of sensors.

Example 41

The system of Example 40, wherein the plurality of sensors includes a first sensor array associated with the shaft and a second sensor array associated with the sleeve, wherein the controller is configured to combine information from the first sensor array and the second sensor array to compute the remote center of motion.

Example 42

The system of any of Examples 40 through 41, wherein the controller is configured to recompute the remote center of motion based on information from the plurality of sensors during a procedure.

Example 43

The system of any of Examples 40 through 42, further comprising at least one position marker, wherein the at least one position marker is configured to be associated with the patient to detect movement of the patient, wherein the controller is configured to recompute the remote center of motion upon detection of movement of the patient as indicated by the at least one position marker.

Example 44

An apparatus, comprising: (a) a base portion configured to selectively couple with a robotic arm; (b) a shaft extending distally form the base portion and terminating into a distal end; (c) a sleeve slidably coupled to the shaft; (d) a colpotomy cup fixedly secured to a portion of the sleeve; and (e) a one or more sensors configured to detect the position of the shaft and the sleeve relative to one or more anatomical features of a patient.

Example 45

The apparatus of Example 44, wherein the one or more sensors includes an optical sensor configured to detect a position of a position marker associated with the patient.

Example 46

The apparatus of any of Examples 44 through 45, wherein the one or more sensors includes a capacitive sensor and an impedance sensor, wherein the capacitive sensor and the impedance sensor are both in communication with a console for detection of the position of the shaft and the sleeve relative to the patient.

Example 47

The apparatus of any of Examples 44 through 46, wherein the one or more sensors includes an electromagnetic sensor configured to detect a position of the patient.

Example 48

A method for repositioning a remote center of motion during a robotic manipulation of an instrument, comprising: (a) calculating a remote center of motion associated with the instrument inserted into a patient; (b) identifying a first position of the patient using at least one position marker positioned on the patient; (c) detecting movement of the patient from the first position to a second position by detecting movement of the at least one position marker, the movement of the patient occurring after calculating the remote center of motion; and (c) recalculating the remote center of motion based on the detected movement of the patient from the first position to the second position.

Example 49

The method of Example 48, further comprising initially positioning the remote center of motion using one or more sensors disposed on the instrument.

Example 50

The method of any of Examples 48 through 49, further comprising pausing the robotic manipulation of the instrument after detecting movement of the patient from the first position to the second position.

Example 51

The method of any of Examples 48 through 50, wherein the position marker includes an optical position marker.

Example 52

The method of any of Examples 48 through 51, wherein the position marker includes an electromagnetic position sensor.

Example 53

The method of any of Examples 48 through 52, further comprising positioning the patient in a Trendelenburg position prior to the step of identifying the first position.

Example 54

An apparatus, comprising: (a) a base portion configured to selectively couple with a robotic arm; (b) a shaft extending distally form the base portion and terminating into a distal end; (c) a sleeve slidably coupled to the shaft; (d) a colpotomy cup fixedly secured to a portion of the sleeve; and (e) one or more sensors configured to detect a force applied to: (i) the sleeve, (ii) the shaft, or (iii) both the sleeve and the shaft.

Example 55

The apparatus of Example 54, wherein the one or more sensors includes a sensor array disposed on an outer surface of the sleeve.

Example 56

The apparatus of Example 55, wherein the sensor array extends along an axial length of the sleeve.

Example 57

The apparatus of any of Examples 55 through 56, wherein the sensor array extends around a circumference of the sleeve.

Example 58

The apparatus of any of Examples 54 through 57, wherein the one or more sensors includes a load cell associated with the shaft.

Example 59

A system, comprising: (a) the apparatus of any of Examples 54 through 58; and (b) a console having a display and one or more user inputs configured to initiate movement of the robotic arm, wherein the one or more sensors are in communication with the counsel.

Example 60

The system of Example 59, wherein the display of the console includes a graphical force indicator configured to graphically depict a level of force detected by the one or more sensors.

Example 61

The system of Example 60, wherein the graphical force indicator includes a force scale and a force indicator, wherein the console is configured to drive the force indicator relative to the force scale to depict the level of force detected by the one or more sensors.

Example 62

The system of Example 61, wherein the graphical force indicator further includes one or more threshold indicators positioned at a predetermined location relative to the force scale.

Example 63

The system of any of Examples 61 through 62, wherein at least one of the one or more threshold indicators are operator selectable.

Example 64

The system of any of Examples 59 through 63, wherein the console is configured to compare a detected level of force to a predetermined threshold level of force.

Example 65

The apparatus of Example 64, wherein the console is configured to provide a warning to an operator when the detected level of force is greater than the predetermined threshold level of force.

Example 66

The system of Example 65, wherein the warning includes any one or more of a visual warning, a haptic warning, or an auditory warning.

Example 67

The system of any of Examples 65 through 66, wherein the console is configured to disable the one or more user inputs when the detected level of force is greater than the predetermined threshold level.

Example 68

The system of any of Examples 59 through 67, wherein the console is configured to detect a directional component associated with the force.

Example 69

A system, comprising: (a) a robotic platform including a plurality of robotic arms; (b) a uterine manipulator, including: (i) a shaft extending along a curved path, (ii) a sleeve slidably coupled to the shaft, and (iii) a colpotomy cup fixedly secured to a portion of the sleeve; (c) a console configured to control each robotic arm of the plurality of robotic arms; and (d) a force sensing feature in communication with the console, wherein the force sensing feature is configured to detect a force applied to at least a portion of the uterine manipulator.

Example 70

The system of Example 69, wherein the force sensing feature includes a load cell incorporated into at least one robotic arm of the plurality of robotic arms.

Example 71

The system of any of Examples 69 through 70, wherein the force sensing feature includes a plurality of sensors arranged in a circumferential and longitudinal array about an outer surface of the sleeve of the uterine manipulator.

Example 72

The system of any of Examples 69 through 71, wherein the force sensing feature is in communication with the console to communicate a detected level of force to the console, wherein the console is configured to prevent movement of one or more robotic arms of the plurality of robotic arms in response to the detected level of force exceeding a predetermined threshold value.

Example 73

A method for detecting force applied to a robotically controlled uterine manipulator, comprising: (a) manipulating an anatomical feature of a patient using the uterine manipulator; (b) detecting a level of force applied to at least a portion of the uterine manipulator; (c) comparing the detected level of force to a predetermined level of force; and (d) prompting an operator when the detected level of force exceeds the predetermined level of force.

Example 74

The method of Example 73, wherein the step of prompting the operator includes providing any one or more of a visual, auditory, or haptic alert to the operator.

Example 75

The method of any of Examples 73 through 74, further comprising displaying the detected level of force to the operator.

Example 76

The method of any of Examples 73 through 75, wherein the step of detecting the level of force includes detecting a level of force applied to a sleeve of the uterine manipulator.

Example 77

The method of any of Examples 73 through 76, wherein the step of detecting the level of force includes detecting a level of force applied to a robotic arm via the uterine manipulator.

Example 78

The method of any of Examples 73 through 77, further comprising preventing movement of the uterine manipulator when the detected level of force exceeds the predetermined level of force.

VI. Miscellaneous

For clarity of disclosure, the terms "proximal" and "distal" are defined herein relative to a surgeon or other operator grasping a surgical instrument having a distal surgical end effector. The term "proximal" refers the position of an element closer to the surgeon or other operator and the term "distal" refers to the position of an element closer to the surgical end effector of the surgical instrument and further away from the surgeon or other operator.

It should be noted that the terms "couple," "coupling," "coupled" or other variations of the word couple as used herein may indicate either an indirect connection or a direct connection. For example, if a first component is "coupled" to a second component, the first component may be either indirectly connected to the second component via another component or directly connected to the second component.

The methods disclosed herein comprise one or more steps or actions for achieving the described method. The method steps and/or actions may be interchanged with one another without departing from the scope of the claims. In other words, unless a specific order of steps or actions is required for proper operation of the method that is being described, the order and/or use of specific steps and/or actions may be modified without departing from the scope of the claims.

As used herein, the term "plurality" denotes two or more. For example, a plurality of components indicates two or more components. The term "determining" encompasses a wide variety of actions and, therefore, "determining" can include calculating, computing, processing, deriving, investigating, looking up (e.g., looking up in a table, a database or another data structure), ascertaining and the like. Also, "determining" can include receiving (e.g., receiving information), accessing (e.g., accessing data in a memory) and the like. Also, “determining” can include resolving, selecting, choosing, establishing and the like.

The phrase “based on” does not mean “based only on,” unless expressly specified otherwise. In other words, the phrase “based on” describes both “based only on” and “based at least on.”

It should be understood that any of the versions of the instruments described herein may include various other features in addition to or in lieu of those described above. By way of example only, any of the devices herein may also include one or more of the various features disclosed in any of the various references that are incorporated by reference herein. Various suitable ways in which such teachings may be combined will be apparent to those skilled in the art.

While the examples herein are described mainly in the context of electrosurgical instruments, it should be understood that various teachings herein may be readily applied to a variety of other types of devices. By way of example only, the various teachings herein may be readily applied to other types of electrosurgical instruments, tissue graspers, tissue retrieval pouch deploying instruments, surgical staplers, surgical clip appliers, ultrasonic surgical instruments, etc. It should also be understood that the teachings herein may be readily applied to any of the instruments described in any of the references cited herein, such that the teachings herein may be readily combined with the teachings of any of the references cited herein in numerous ways. Other types of instruments into which the teachings herein may be incorporated will be apparent to those skilled in the art.

It should be understood that any one or more of the teachings, expressions, embodiments, examples, etc. described herein may be combined with any one or more of the other teachings, expressions, embodiments, examples, etc. that are described herein. The above-described teachings, expressions, embodiments, examples, etc. should therefore not be viewed in isolation relative to each other. Various suitable ways in which the teachings herein may be combined will be readily apparent to those skilled in the art in view of the teachings herein. Such modifications and variations are intended to be included within the scope of the claims.

It should be appreciated that any patent, publication, or other disclosure material, in whole or in part, that is said to be incorporated by reference herein is incorporated herein only to the extent that the incorporated material does not conflict with existing definitions or other disclosure material set forth in this disclosure. As such, and to the extent necessary, the disclosure as explicitly set forth herein supersedes any conflicting material incorporated herein by reference. Any material, or portion thereof, that is said to be incorporated by reference herein, but which conflicts with existing definitions or other disclosure material set forth herein will only be incorporated to the extent that no conflict arises between that incorporated material and the existing disclosure material.

Versions described above may be designed to be disposed of after a single use, or they can be designed to be used multiple times. Versions may, in either or both cases, be reconditioned for reuse after at least one use. Reconditioning may include any combination of the steps of disassembly of the device, followed by cleaning or replacement of particular pieces, and subsequent reassembly. In particular, some versions of the device may be disassembled, and any number of the particular pieces or parts of the device may be selectively replaced or removed in any combination. Upon cleaning and/or replacement of particular parts, some versions of the device may be reassembled for subsequent use either at a reconditioning facility, or by an operator immediately prior to a procedure. Those skilled in the art will appreciate that reconditioning of a device may utilize a variety of techniques for disassembly, cleaning/replacement, and reassembly. Use of such techniques, and the resulting reconditioned device, are all within the scope of the present application.

By way of example only, versions described herein may be sterilized before and/or after a procedure. In one sterilization technique, the device is placed in a closed and sealed container, such as a plastic or TYVEK bag. The container and device may then be placed in a field of radiation that can penetrate the container, such as gamma radiation, x-rays, or high-energy electrons. The radiation may kill bacteria on the device and in the container. The sterilized device may then be stored in the sterile container for later use. A device may also be sterilized using any other technique known in the art, including but not limited to beta or gamma radiation, ethylene oxide, or steam.

Having shown and described various embodiments of the present invention, further adaptations of the methods and systems described herein may be accomplished by appropriate modifications by one of ordinary skill in the art without departing from the scope of the present invention. Several of such potential modifications have been mentioned, and others will be apparent to those skilled in the art. For instance, the examples, embodiments, geometrics, materials, dimensions, ratios, steps, and the like discussed above are illustrative and are not required. Accordingly, the scope of the present invention should be considered in terms of the following claims and is understood not to be limited to the details of structure and operation shown and described in the specification and drawings.

We claim:

1. A system, comprising:

(a) a robotic platform, including:

(i) a base, (ii) a plurality of robotic arms, and (iii) a grounding structure configured to couple one or more of the robotic arms to the base; and (b) a uterine manipulator, including:

(i) an interface configured to couple with a first robotic arm of the robotic platform, (ii) a shaft assembly extending from the interface, (iii) a colpotomy cup slidably attached along a length of the shaft assembly, and (iv) a lock ring concentric with the shaft and axially fixed with the colpotomy cup, in both a locked and unlocked state, wherein rotation of the lock ring about an axis concentric with the shaft to a first angular position provides the unlocked state and rotation of the lock ring about an axis concentric with the shaft to a second angular position provides the locked state.

2. The system of claim 1, the robotic platform further including a patient table, wherein the grounding structure is positioned proximate a side of the patient table.

3. The system of claim 1, wherein the grounding structure includes an elongate rail, wherein the first robotic arm is slidably disposed on the elongate rail.

4. The system of claim 3, wherein the grounding structure is configured to robotically move the first robotic arm along a length defined by the grounding structure.

5. The system of claim 3, wherein the grounding structure is configured to permit the first robotic arm to be moved manually along a length defined by the grounding structure.

6. The system of claim 1, wherein the grounding structure is configured to move relative to the patient table.

7. The system of claim 1, wherein the grounding structure is configured to support the plurality of robotic arms relative to a patient with the robotic arm being positioned over a leg of the patient with the robotic arm approaching the patient from a lateral side of the patient.

8. The system of claim 1, wherein the grounding structure is configured to support the plurality of robotic arms relative to a patient with the robotic arm being positioned under a leg of the patient with the robotic arm approaching the patient from a lateral side of the patient.

9. The system of claim 1, wherein the robotic platform further includes a console and an operator interface feature, wherein the operator interface feature is separate from the console.

10. The system of claim 9, wherein the operator interface feature includes one or more robotic control buttons configured to initiate movement of the first robotic arm.

11. The system of claim 9, wherein the operator interface feature is incorporated into at least a portion of the first robotic arm.

12. The system of claim 9, wherein the operator interface feature includes a wearable robotic user interface.

13. The system of claim 9, wherein the operator interface feature includes one or more multi-axis control pads.

14. The system of claim 9, wherein the operator interface feature includes a haptic feedback device.

15. The system of claim 1, wherein the robotic platform further includes a second robotic arm, wherein the second robotic arm is configured to support one or more endoscopic or laparoscopic instruments.

16. The system of claim 1, wherein the colpotomy cup has first state the first state permitting movement along the shaft and a second state, the second state preventing movement along the shaft.

17. The system of claim 16, wherein the lock ring has a first rotational position that corresponds to the first state, and a second rotational position that corresponds to the second state.

18. The system of claim 17, wherein the lock ring is concentric with the shaft in both the first and second rotational positions.

* * * * *